US009382245B2

(12) United States Patent
Jorgensen et al.

(10) Patent No.: US 9,382,245 B2
(45) Date of Patent: Jul. 5, 2016

(54) COMPOUNDS AND METHODS FOR TREATING HIV INFECTIONS

(71) Applicant: YALE UNIVERSITY, New Haven, CT (US)

(72) Inventors: William L. Jorgensen, Deep River, CT (US); Karen S. Anderson, Guilford, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 14/509,301

(22) Filed: Oct. 8, 2014

(65) Prior Publication Data

US 2015/0105351 A1    Apr. 16, 2015

Related U.S. Application Data

(60) Provisional application No. 61/889,751, filed on Oct. 11, 2013.

(51) Int. Cl.
*C07D 471/04* (2006.01)
*C07D 239/54* (2006.01)
*A61K 31/513* (2006.01)
*A61K 45/06* (2006.01)
*C07D 403/12* (2006.01)
*C07D 407/12* (2006.01)

(52) U.S. Cl.
CPC ............ *C07D 471/04* (2013.01); *A61K 31/513* (2013.01); *A61K 45/06* (2013.01); *C07D 239/54* (2013.01); *C07D 403/12* (2013.01); *C07D 407/12* (2013.01)

(58) Field of Classification Search
None
See application file for complete search history.

(56) References Cited

U.S. PATENT DOCUMENTS

| 8,492,415 B2 | 7/2013 | Jorgensen |
| 2012/0040974 A1 | 2/2012 | Jorgensen et al. |
| 2014/0288017 A1 | 9/2014 | Jorgensen et al. |

FOREIGN PATENT DOCUMENTS

| WO | 2004071389 A2 | 8/2004 | | |
| WO | 2008055808 A1 | 5/2008 | | |
| WO | WO2013/056003 | * | 4/2013 | ........... C07D 239/10 |

OTHER PUBLICATIONS

Ma D, Cai Q. N,N-Dimethyl Glycine-Promoted Ullmann Coupling Reaction of Phenols and Aryl Halides. Organic Letters, 2003;5(21):3799-3802.
Jacquemard U, et al. Mild and selective deprotection of carbamates with Bu4NF. Tetrahedron, 2004;60:10039-10047.
Bollini M, et al. Computationally-Guided Optimization of a Docking Hit to Yield Catechol Diethers as Potent Anti-HIV Agents. J Med Chem, 2011;54:8582-8591.
Zheng C, et al. The Enantioselective, Organocatalyzed Diels-Alder Reaction of 2-Vinylindoles with alpha,beta-Unsaturated Aldehydes: An Efficient Route to Functionalized Tetrahydrocarbazoles. Chem Eur J, 2010;16:5853-5857.
Ryabova Sy, et al. Synthesis of 4-aminopyrido[3,2-b]indole derivatives. Russian Chemical Bulletin, International Edition, 2006;55(7):1248-1254.
Attanasi O, et al. Effect of Metal Ions in Organic Synthesis; XVII. Mild, Easy, and High-Yield Conversion of Alsoximes into Nitriles under Copper(II) Acetate-Catalysis. Synthesis, 1983;9:741-742.
Bode ML, Kaye PT. Indolizine Studies. Part 2. Synthesis and NMR Spectroscopic Analysis of 2-Substituted Indolizines. J Chem Soc Perkin Trans, 1993;1:1809-1813.
Newman Sg, et al. Intramolecular cross-coupling of gem-dibromoolefins: a mild approach to 2-bromo benzofused heterocycles. Chem Commun, 2009;;5236-5238.
Zhou W, et al. A highly efficient one-pot reaction of 2-(gem-dibromovinyl)Phenols-(thiophenols) with K4Fe(CN)6 to 2-cyanobenzofurans(thiophenes). Org Biomol Chem, 2012;10:4172-4178.
Lee WG, et al. Picomolar Inhibitors of HIV Reverse Transcriptase Featuring Bicyclic Replacement of a Cyanovinylphenyl Group. J Am Chem Soc, 2013;135:16705-16713.
Liu X, Zhang S. Efficient Iron/Copper-Cocatalyzed O-Arylation of Phenols with Bromoarenes. Synlett, 2011;2:268-272.
Niculescu-Duvaz D, et al. Potent BRAF Kinase inhibitors based on 2,4,5-trisubstituted imidazole with naphthyl and benzothiophene 4-substituents. Bioorganic & Medicinal Chemistry, 2013;21:1284-1304.
Uraguchi D, et al. Flexible synthesis, structural determination, and synthetic application of a New C1-symmetric chiral ammonium betaine. Chem Commun, 2010;46:300-302.
Linghu X, et al. Synthesis of functionalized 3-chloro-1-napthols via Friedel-Crafts acylation of vinyl chlorides. Tetrahedron Letters, 2012;53:1550-1552.
Hartmann RW, et al. CYP 17 and CYP 19 Inhibitors. Evaluation of Fluorine Effects on the Inhibiting Activity of Regioselectively Fluorinated 1-(Naphthalen-2-ylmethyl)imidazoles. Journal of Enzyme Inhibition and Medicinal Chemistry, 2004;19(2):145-155.
Gourves JP, et al. Oxidative Coupling of O-Silyl and O-Alkyl Enethers: Application of the Novel Annulation Sequence to the Synthesis of Fluorinated Naphthaldehydes and Naphthyl Ketones. J Org Chem, 2001;66:617-619.
Frey KM, et al. Crystal Structures of HIV-1 Reverse Transcriptase with Picomolar Inhibitors Reveal Key Interactions for Drug Design. J Am Chem Soc, 2012;134:19501-19503.
Das K, et al. High-resolution structures of HIV-1 reverse transcriptase/TMC278 complexes: Strategic flexibility explains potency against resistance mutations. PNAS, 2008;105(5):1466-1471.
Otwinowski Z, Minor W. Processing of X-Ray Diffraction Data Collected in Oscillation Mode. Methods in Enzymology, 1997;276:307-326.
Mccoy AJ, et al. Phaser crystallographic software. J Appl Cryst, 2007;40:658-674.
Emsley P, et al. Features and development of Coot. Acta Cryst, 2010;D66:486-501.

(Continued)

*Primary Examiner* — Dennis Heyer
(74) *Attorney, Agent, or Firm* — Henry D. Coleman; R. Neil Sudol

(57) ABSTRACT

The present invention is directed to novel nanomolar and picomolar inhibitors of HIV reverse transcriptase, pharmaceutical compositions therefrom and methods for inhibiting reverse transcriptase and treating HIV infections, especially included drug resistant strains of HIV-1 and HIV-2 and/or secondary disease states and/or conditions which occur as a consequence of HIV infection.

19 Claims, 5 Drawing Sheets

(56) References Cited

OTHER PUBLICATIONS

Adams Pd, et al. Phenix: a comprehensive Python-based system for macromolecular structure solution. Acta Cryst, 2010:D66:213-221.
Terwilliger TC, et al. Iterative-build OMIT maps: map improvement by iterative model building and refinement without model bias. Acta Cryst, 2008;D64:515-524.
Asahchop El, et al. Antiviral Drug Resistance and the Need for Development of New HIV-1 Reverse Transcriptase Inhibitors. Antimicrobial Agents and Chemotherapy, 2012;56(10):5000-5008.
Zhan P, et al. HIV-1 NNRTIs: Structural Diversity, Pharmacophore Similarity, and Implications for Drug Design. Med Res Rev, 2013;33:E1-E72.
Permpalung N, et al. Treatment of HIV infection with once-daily regimens. Expert Opin Pharmacother, 2012;13 (16):2301-2317.
James C, et al. Rilpivarine: A second-generation nonnucleoside reverse transcriptase inhibitor. Am J Health-Syst PHarm, 2012;69:857-861.
Janssen Paj, et al. In Search of a Novel Anti-HIV Drug: Multidisciplinary Coordination in the Discovery of 4-[[4-[[4[(1E)-2-Cyanoethenyl]-2,6-dimethylphenyliamino]-2-pyrimidinyl-lamino]benzonitrile (R278474, Rilpivirine). J Med Chem, 2005;48:1901-1909.
Bollini M, et al. Optimization of diarylazines as anti-HIV agents with dramatically enhanced solubility. Bioorganic & Medicinal Chemistry Letters, 2013;23:5213-5216.
Jorgensen WL. Efficient Drug Lead Discovery and Optimization. Accounts of Chemical Research, 2009;42 (6):724-733.
Stepan AF, et al. Structural Alert/Reactive Metabolite Concept as Applied in Medicinal Chemistry to Mitigate the Risk of Idiosyncratic Drug Toxicity: A Perspective Based on the Critical Examination of Trends in the Top 200 Drugs Marketed in the United States. Chem Res Toxicol, 2011;24:1345-1410.
Fleming FF, Wang Q. Unsaturated Nitriles: Conjugate Additions of Carbon Nucleophiles to a Recalcitrant Class of Acceptors. Chem Rev, 2003;103:2035-2077.
Dahlgren MK, et al. Characterization of Biaryl Torsional Energetics and its Treatment in OPLS All-Atom Force Fields. J Chem Inf Model, 2013;53:1191-1199.
Fleming FF, et al. Nitrile-Containing Pharmaceuticals: Efficacious Roles of the Nitrile Pharmacophore. J Med Chem, 2010;53:7902-7917.
Jorgensen WL, et al. Efficient Discovery of Potent Anti-Hiv Agents Targeting the Tyr181Cys Variant of HIV Reverse Transcriptase. J Am Chem Soc, 2011;133:15686-15696.
Jorgensen WL, Tirado-Rives J. Molecular Modeling of Organic and Biomolecular Systems Using Boss and Mcpro. J Comput Chem, 2005;26:1689-1700.
Jorgensen WL, et al. Development and Testing of the OPLS All-Atom Force Field on Conformational Energetics and Properties of Organic Liquids. J Am Chem Soc, 1996;118:11225-11236.
Jorgensen WL, Tirado-Rives J. Potential energy functions for atomic-level simulations of water and organic and biomolecular systems. PNAS, 2005;102(19):6665-6670.
Jorgensen WL, et al. Comparison of simple potential functions for simulating liquid water. The Journal of Chemical Physics, 1983;79:926-935.
Jorgensen WL, Thomas LL. Perspective on Free-Energy Perturbation Calculations for Chemical Equilibria. J Chem Theory COmput, 2008;4:869-876.
Heugebaert TSA, et al. Synthesis of isoindoles and related iso-condensed heteroaromatic pyrroles. Chem Soc Rev, 2012;41:5626-5640.
Kim JT, et al. FEP-Guided Selection of Bicyclic Heterocycles in Lead Optimization for Non-Nucleoside Inhibitors of Hiv-1 Reverse Transcriptase. J Am Chem Soc, 2006;128:15372-15373.
Whitlock GA, et al. 1-(2-Phenoxyphenyl)methanamines: SAR for dual serotonin/noradrenaline reuptake inhibition, metabolic stability and hERG affinity. Bioorganic & Medicinal Chemistry Letters, 2008;18:596-599.
Lin TS, et al. Antiviral Activity of 2',3'-Dideoxy-beta-L-5-Fluorocytidine (beta-L-FddC) and 2',3'-Dideoxy-beta-L-Cytidine (Beta-L-ddC) Against Hepatitis B Virus and Human Immunodeficiency Virus Type 1 In Vitro. Biochemical Pharmacology, 1994;47(2):171-174.
Ray AS, et al. Novel Use of a Guanosine Prodrug Approach to Convert 2' 3'-Didehyrdro-2',3'-Dideoxyguanosine into a Viable Antiviral Agent. Antimicrobial Agents and Chemotherapy, 2002;46(3):887-891.
Bethune MP. Non-nucleoside reverse transcriptase inhibitors (NNRTIs), their discovery, development, and use in the treatment of HIV-1 infection: A review of the last 20 years (1989-2009). Antiviral Research, 2010;85:75-90.
Lipinski CA, et al. Experimental and computational approaches to estimate solubility and permeability in drug discovery and development settings. Advanced Drug Delivery Reviews, 2001;46:3-26.
Jorgensen WL, Duffy EM. Prediction of drug solubility from structure. Advanced Drug Delivery Reviews, 2002;54:355-366.
Morelock MM, et al. Estimation and Correlation of Drug Water Solubility with Pharmacological Parameters Required for Biological Activity. Journal of Pharmaceutical Sciences, 1994;83(7):948-952.
Weuts I, et al. Physicochemical Properites of the Amorphous Drug, Cast Films, and Spray Dried Powders to Predict Formulation Probability of Success for Solid Dispersions: Etravirine. Journal of Pharmaceutical Sciences, 2011;100 (1):260-274.
1 Sun LQ, et al. Optmzatons of 2,4-diarylanilines as non-nucleosdeHIV-1 reverse transcriptase inhibitors Bioorganic & Medicinal Chemistry Letters, 2012;22:2376-2379.
De Clercq E. The Nucleoside Reverse Transcriptase Inhibitors Non-nucleoside Reverse Transcriptase Inhibitors, and Protease Inhibitors in the Treatment of HIV Infections (AIDS). Advance in Pharmacology, 2013;7:317-358.
Reynolds C, et al. In search of a treatment for HIV-current therapies and the role of non-nucleoside reverse transcriptase inhibitors (NNRTIs). Chem Soc Rev, 2012;41:4657-4670.
Frey KM et al. Structure-Based Evaluation of C5 Derivatives in the Catechol Diether Series Targeting HIV-1 Reverse, Transcriptease. Chem Biol Drug Des, 2014;83:541-549.
Baka E, et al. Study of equilibrium solubility measurement by saturation shake-flask method using hydrochlorothiazide as model compound. Journal of Pharmaceutical and Biomedical Analysis, 2008;46:335-341.
Jorgensen WL, et al. Efficient Drug Lead Discovery and Optimization. Accounts of Chemical Research, 2009;42 (6):724-733.

* cited by examiner

COMPOUNDS AND METHODS FOR TREATING HIV INFECTIONS

RELATED APPLICATIONS

This application claims the benefit of priority of U.S. provisional application Ser. No. U.S. 61/889,751, filed Oct. 11, 2013, entitled "Compounds and Methods for Treating HIV Infections", the entire contents of which are incorporated by reference herein.

GOVERNMENT SUPPORT

This invention was made with government support under AI044616, GM032136, GM049551 and AI104334 awarded by National Institutes of Health. The government has certain rights in the invention.

FIELD OF THE INVENTION

The present invention is directed to novel compounds as nanomolar and picomolar inhibitors of HIV reverse transcriptase, pharmaceutical compositions comprising such inhibitors and methods for inhibiting reverse transcriptase and treating HIV infections (particularly infections caused by drug resistant strains of HIV-1 and HIV-2 and/or secondary disease states and/or conditions which occur as a consequence of HIV infection).

BACKGROUND OF THE INVENTION

Inhibitors of HIV-1 reverse transcriptase are central to anti-HIV therapy.[1] Though there are five FDA-approved drugs in the non-nucleoside class,[2] efavirenz (1) and rilpivirine (2) are particularly important as they are components of the one-a-day combination therapies Atripla and Complera.[3] The other two components of the pills are the same, emtricitabine and tenofovir, which are in the nucleoside class of HIV-RT inhibitors. The goal of our research has been to discover new non-nucleoside inhibitors (NNRTIs) that may incorporate advantages for administration, formulation, diminished side effects, and activity towards variant strains of the virus.

For example, issues with efavirenz include its daily dosage of 600 mg, poor activity towards HIV-1 variants containing the commonly occurring Lys103Asn (K103N) mutation in RT, and neurological side effects. The situation with rilpivirine is curious. Although it has much superior performance in cell-based assays that efavirenz, more virological failure is observed for patients using Complera than Atripla.[3,4] Another unusual feature of rilpivirine is its extremely low aqueous solubility (0.02 µg/ml)[5] in comparison to the typical range of 4-4000 µg/ml for oral drugs.[6]

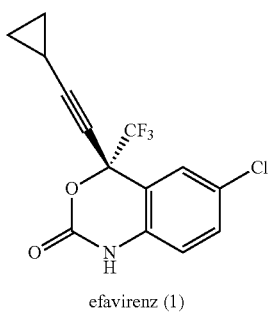

efavirenz (1)

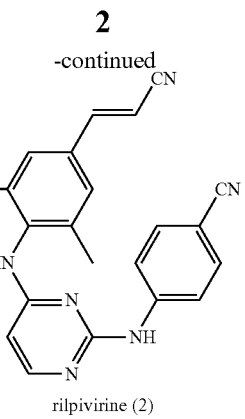

rilpivirine (2)

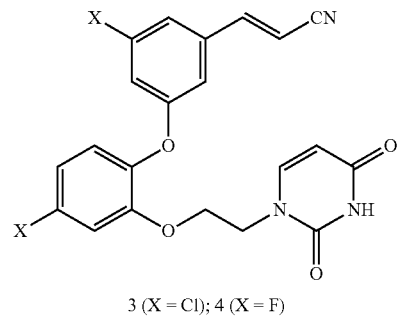

3 (X = Cl); 4 (X = F)

The challenges in developing new NNRTIs that represent an advance over existing compounds are great. One seeks simultaneously compounds that embody high potency towards the wild-type (WT) virus and numerous clinically observed variants, good pharmacological properties including solubility, an absence of structural features that may lead to rapid metabolism, and avoidance of toxicities stemming from reactive functional groups or metabolic products.[7,8]

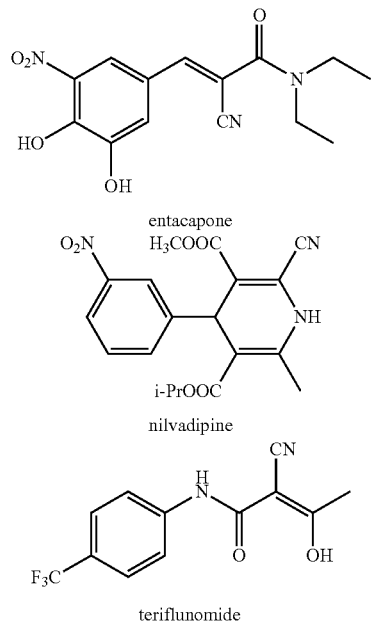

entacapone nilvadipine teriflunomide

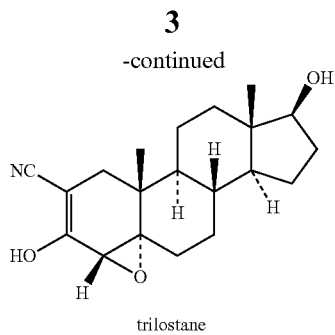

trilostane

A particularly promising class of NNRTIs that we have developed is catechol diethers including 3 and 4.[9] 3 appears to be the most potent anti-HIV agent ever reported with an EC$_{50}$ of 0.055 nM in the standard MT-2 cell assay using wild-type HIV-1. The difluoro analog 4 is also extremely potent at 0.32 nM, has good potency towards variant strains containing the Y181C (16 nM) and K103N/Y181C (85 nM) mutations, and shows low cytotoxicity towards the T-cells (CC$_{50}$=45 µM). It was also possible to obtain X-ray crystal structures of 3 and 4 in complex with WT HIV-RT.[10] Thus, further structure-based design activities in the catechol diether series have a firm foundation.

A structural feature in 3 and 4 as well as in rilpivirine that is addressed here is the cyanovinyl (CV) group. For most medicinal chemists viewing these structures, concern arises that the CV group may be sufficiently electrophilic to act as a "Michael acceptor" leading to potential covalent modification of proteins, nucleic acids, or other biological entities. Though in reality unsaturated nitriles are poor Michael acceptors that require reactive organometallic nucleophiles to undergo conjugate additions,[11] the fact is almost no approved drugs contain a cyanovinyl group, and lack of precedent is often taken as a warning sign in drug discovery. When a search is done for a C=C—C≡N substructure in a comprehensive file containing the structures of ca. 1900 approved oral drugs,[12] there are just five hits: rilpivirine, entacapone, nilvadipine, teriflunomide, and trilostane. For the latter two examples, the substructure only arises as a tautomer of an α-cyanoketone. Rilpivirine is unique in incorporating a simple CV group. By contrast, non-vinyl cyano groups are generally considered to be acceptable in drugs;[13] there are 36 examples in the database.

Thus, we set out to find a replacement for the cyanovinyl group in the catechol diethers.

SUMMARY OF THE INVENTION

In the present work, computer simulations were used to design bicyclic replacements for the CVP group. The predicted viability of a 2-cyanoindolizinyl alternative was confirmed experimentally and provided compounds with 0.4-nM activity against the wild-type virus. The compounds also performed well with EC$_{50}$ values of 10 nM against the challenging HIV-1 variant that contains the Lys103Asn/Tyr181Cys double mutation in the RT enzyme. Indolyl and benzofuranyl analogs were also investigated; the most potent compounds in these cases have EC$_{50}$ values towards wild-type HIV-1 near 10 nM and high-nM activities towards the double-variant. The structural expectations from the modeling were much enhanced by obtaining an X-ray crystal structure at 2.88-Å resolution for the complex of the parent 2-cyanoindolizine 10b and HIV-1 RT. The aqueous solubilities of the most potent indolizine analogs were also measured to be ca. 40 µg/ml, which is similar to that for the approved drug efavirenz and ca. 1000-fold greater than for rilpivirine.

In one embodiment, the invention provides a compound of the formula (I):

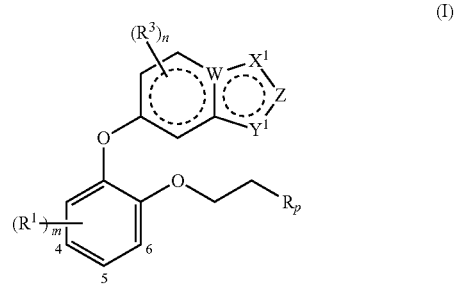

wherein:

R$^1$ is H, a halogen (F, Cl, Br, I, especially F, Cl, or Br), CN, NO$_2$, an optionally substituted alkyl group, preferably a C$_1$-C$_6$ alkyl group (preferably CH$_3$ and including CF$_3$);

R$^3$ is H, OH, a C$_1$-C$_3$ alkyl group which is optionally substituted with up to 3 halogens (preferably F), a halogen (preferably F, Cl or Br), NO$_2$ or CN;

R$_p$ is an optionally substituted five- or six-membered heterocycle, including pyrimidine derivatives linked at the 1-position of the pyrimidine, or is a uracil moiety linked at the 1-position and optionally substituted at the 5- or 6-position (preferably the 5-position) with a substituent R$^{2a}$;

R$^{2a}$ is H, halogen (preferably F, Cl or Br), optionally substituted C$_1$-C$_3$ alkyl (preferably methyl, ethyl or trifluoromethyl), optionally substituted —O—(C$_1$-C$_3$) alkyl (methyl, ethyl, propyl, isopropyl), including O—CF$_3$, CN;

W is N or C;

X$^1$ is

O or N—R$^X$ when W is C, and

when W is N;

Z is

(the double bond can be on either side of the carbon depending on X$^1$ and Y$^1$);

$Y^1$ is $$-\overset{R^2}{\underset{\parallel}{C}}\diagup$$

O or N—$R^Y$ when W is C, and $$-\overset{R^2}{\underset{\parallel}{C}}\diagup$$

when W is N;

$R^2$ is H, a $C_1$-$C_6$ alkyl (preferably $C_1$-$C_3$ alkyl, including cyclopropyl) or a $C_2$-$C_6$ alkenyl optionally substituted with up to three fluorines (e.g. $CF_3$), CN, halogen (F, Br, Cl, I), $C_1$-$C_6$ alkoxy; $C_1$-$C_6$ hydroxyalkyl, $C_1$-$C_6$ alkoxyalkyl, $C_1$-$C_6$ polyoxyalkyl (e.g., methoxyethoxy) or a vinyl-$R^2$ (substituted on the first or second carbon of the vinyl group, preferably on the second carbon cis or trans, more preferably trans); $R^X$ and $R^Y$ are each independently H or a $C_1$-$C_6$ alkyl (or a $C_1$-$C_3$ alkyl) group, optionally substituted with one or two hydroxyl groups; and m is 0, 1, 2, 3 or 4 and n is 0, 1, 2 or 3;

and the pharmaceutically acceptable salts, solvates and polymorphs thereof; provided that the following compounds are excluded:

(1) the compound of formula I where $R_p$ is uracil, W is C, $X^1$ is N—$R^X$, $R^X$ is H, $Y^1$ is $$-\overset{}{\underset{R^2}{C}}\diagup$$

where $R^2$ is H, $R^1$ is 4-H, $R^3$ is 6-H, Z is $$-\overset{R^2}{\underset{\parallel}{C}}\diagup$$

where $R^2$ is H and m and n are 1
(the compound

[structure: indole connected via O to phenyl ring, with OCH2CH2 linker to uracil N]

(2) the compound of formula I where $R_p$ is uracil, W is N, $X^1$ is $$-\overset{R^2}{\underset{\parallel}{C}}\diagup$$

where $R^2$ is H, $Y^1$ is $$-\overset{\parallel}{\underset{R^2}{C}}\diagup$$

where $R^2$ is H, $R^1$ is 4-H, $R^3$ is 6-H, m and n are 1, Z is $$-\overset{R^2}{\underset{\parallel}{C}}\diagup$$

and $R^2$ bound to the Z carbon is either $CH_3$ or CN
(the compound

[structure: indolizine with CH3 or CN substituent, connected via O to phenyl, OCH2CH2 to uracil]

(3) the compound of formula I where $R_p$ is uracil, W is C, $X^1$ is O, $Y^1$ is $$-\overset{\parallel}{\underset{R^2}{C}}\diagup,$$

$R^2$ is H, Z is $$-\overset{R^2}{\underset{\parallel}{C}}\diagup,$$

m and n are 1, $R^1$ is 4-Cl, $R^3$ is 6-H and $R^2$ bound to the Z carbon is H or $CH_3$;

(the compound

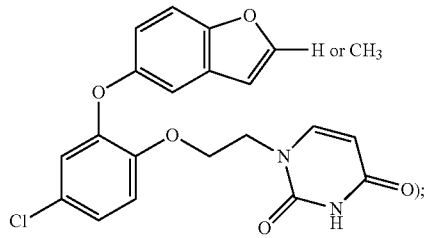

and (4) the compound of formula I where $R_p$ is uracil, W is C, $X^1$ is

where $R^2$ is H, Z is

where $R^2$ is H, $Y^1$ is O, $R^1$ is 4-Cl, $R^3$ is 6-H and m and n are 1
(the compound

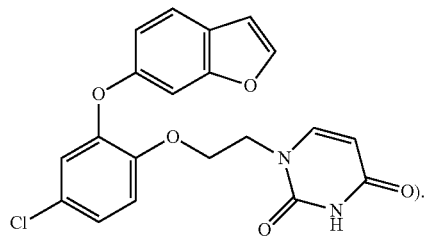

In a preferred embodiment, the compounds of formula (I), and their pharmaceutically acceptable salts, enantiomers, stereoisomers, solvates and polymorphs, have the formula IA, IB, IC, ID, IE or IF:

IA

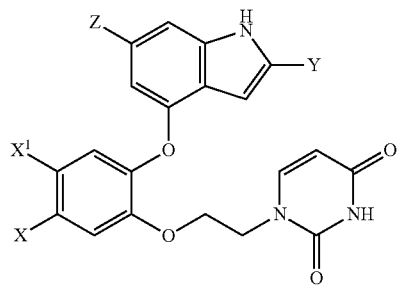

IB

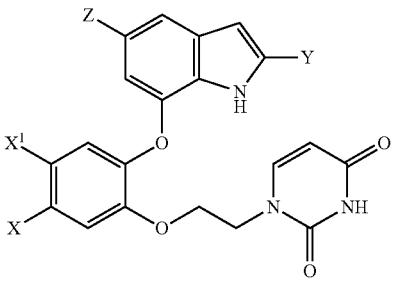

IC

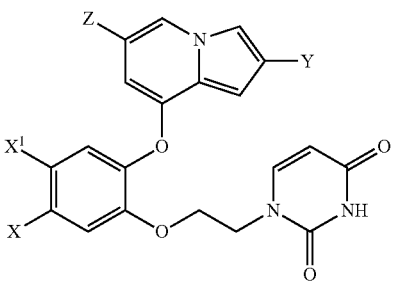

ID

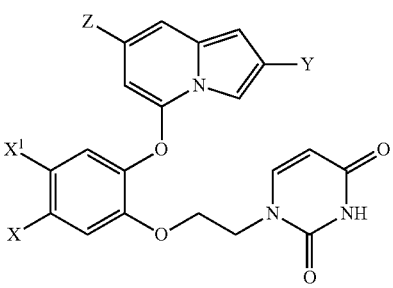

IE

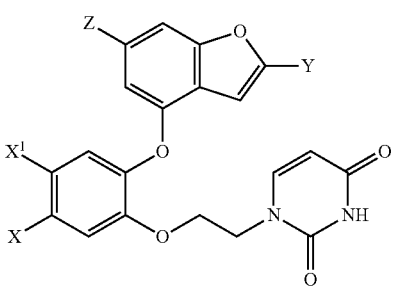

IF

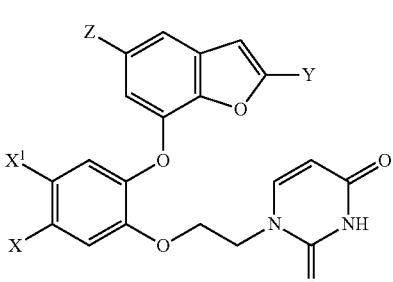

wherein:

X and $X^1$ are independently H, a halogen (F, Cl, Br, I, especially F, Cl, or Br), CN, $NO_2$, an optionally substituted alkyl group, preferably a $C_1$-$C_6$ alkyl group (preferably $CH_3$ and including $CF_3$);

Y is H, a $C_1$-$C_6$ alkyl optionally substituted with up to three fluorines (e.g. $CF_3$), CN or halogen (F, Br, Cl, I), $C_1$-$C_6$ alkoxy; $C_1$-$C_6$ hydroxyalkyl, $C_1$-$C_6$ alkoxyalkyl, $C_1$-$C_6$ polyoxyalkyl (e.g., methoxyethoxy);

Z is H, OH, a $C_1$-$C_3$ alkyl group which is optionally substituted with up to 3 halogens (preferably F), a halogen (preferably F, Cl or Br), $NO_2$ or CN;

provided that the following compounds are excluded:
(1) the compound of formula IA where X, $X^1$, Y and Z are H;
(2) the compound of formula IC where X, $X^1$ and Z are H and Y is $CH_3$ or CN;
(3) the compound of formula IE where X is Cl and $X^1$ and Z are H and Y is H or $CH_3$; and
(4) the compound of formula IF where X is Cl and $X^1$, Y and Z are H.

In another preferred embodiment, in compounds of formula IA, $X^1$ is H and:
(1) X, Y and Z are H; or
(2) X is Cl and Y and Z are H; or
(3) X and Z are H and Y is CN; or
(4) X is H, Y is CN and Z is $CH_3$; or
(5) X is H, Y is CN and Z is Cl.

In another preferred embodiment, in compounds of formula IB, $X^1$ is H and:
(1) X and Y are H and Z is $CH_3$; or
(2) X and Z are H and Y is $CH_3$.

In another preferred embodiment, in compounds of formula IC, $X^1$ is H and:
(1) X is H, Y is CN and Z is H, $CH_3$, F or Cl; or
(2) X is F, Y is CN and Z is H, $CH_3$, F or Cl; or
(3) X is Cl, Y is CN and Z is H or Cl.

In another preferred embodiment of the compounds of formula IC, X and $X^1$ are F, Y is CN and Z is H or F.

In another preferred embodiment, in compounds of formula ID, $X^1$ is H and X is F, Y is CN and Z is H.

In another preferred embodiment, in compounds of formula IE, $X^1$ is H and:
(1) X is H, Y is CN and Z is H, $CH_3$ or Cl; or
(2) X is F, Y is CN and Z is H or $CH_3$; or
(3) X is Cl, Y is CN and Z is H.

In still another embodiment, the invention provides compounds of the formula (II):

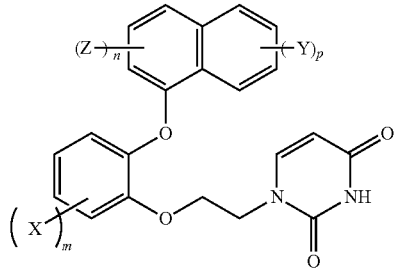

(II)

wherein:
X is H, a halogen (F, Cl, Br, I, especially F, Cl, or Br), CN, $NO_2$, an optionally substituted alkyl group, preferably a $C_1$-$C_6$ alkyl group (preferably $CH_3$ and including $CF_3$);
Y is H, a $C_1$-$C_6$ alkyl optionally substituted with up to three fluorines (e.g. $CF_3$), CN or halogen (preferably F, Br or Cl), $C_1$-$C_6$ alkoxy; $C_1$-$C_6$ hydroxyalkyl, $C_1$-$C_6$ alkoxyalkyl, $C_1$-$C_6$ polyoxyalkyl (e.g., methoxyethoxy);
Z is H, OH, a $C_1$-$C_3$ alkyl group which is optionally substituted with up to 3 halogens (preferably F), a halogen (preferably F, Cl or Br), $NO_2$ or CN; and
m and p are independently 0, 1, 2, 3 or 4 and n is 0, 1, 2 or 3;
and the pharmaceutically acceptable salts, solvates and polymorphs thereof.

In still another embodiment, the invention provides compound of the formula (IIA):

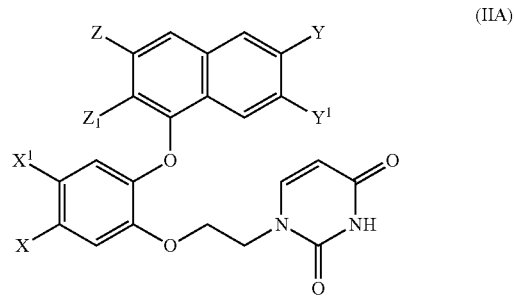

(IIA)

wherein:
X and $X^1$ are independently H, a halogen (F, Cl, Br, I, especially F, Cl, or Br), CN, $NO_2$, an optionally substituted alkyl group, preferably a $C_1$-$C_6$ alkyl group (preferably $CH_3$ and including $CF_3$);
Y and $Y^1$ are independently H, a $C_1$-$C_3$ alkyl optionally substituted with up to three fluorines (e.g. $CF_3$), CN or halogen (preferably F, Br or Cl), $C_1$-$C_6$ alkoxy; $C_1$-$C_6$ hydroxyalkyl, $C_1$-$C_6$ alkoxyalkyl, $C_1$-$C_6$ polyoxyalkyl (e.g., methoxyethoxy); and
Z and $Z^1$ are independently H, OH, a $C_1$-$C_3$ alkyl group which is optionally substituted with up to 3 halogens (preferably F), a halogen (preferably F, Cl or Br), $NO_2$ or CN; and the pharmaceutically acceptable salts, solvates and polymorphs thereof.

In a preferred embodiment of compounds of formula IIA, $X^1$, $Y^1$ and $Z^1$ are H and X and Z are H, F, Cl or Br and Y is CN.

In another preferred embodiment of compounds of formula IIA, $X^1$, $Y^1$ and $Z^1$ are H and X is H or F, Y is CN and Z is H.

In still another embodiment, the present invention is directed to compounds according to the chemical structure:

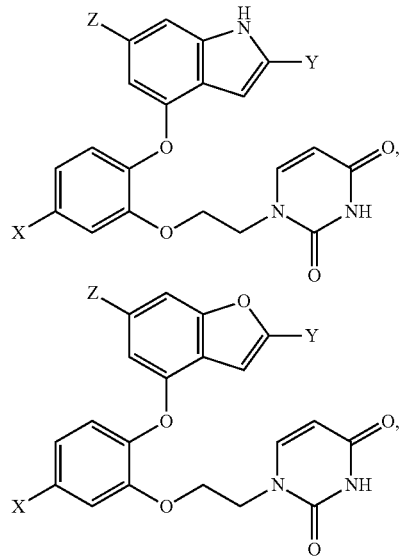

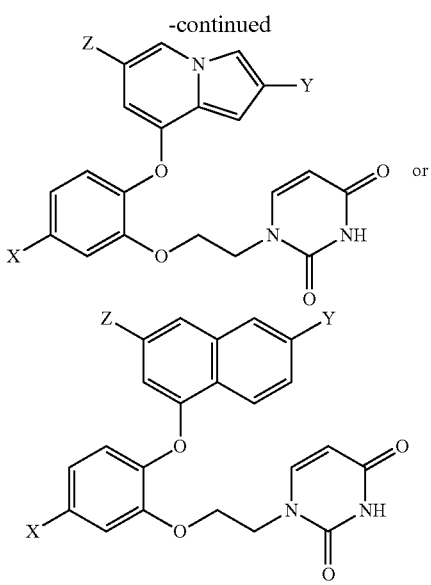

where X is H, Cl or F;
Y is H, CH$_3$, Cl, F or CN (preferably CN); and
Z is H, CH$_3$, Cl or F (preferably, H, Cl or F), or
a pharmaceutically acceptable salt, solvate or polymorph thereof. In preferred aspects of this embodiment, X is H or F, Y is CN and Z is H, F or Cl, often H or F.

Preferred compounds which show exceptional anti-HIV activity (including against WT and mutant strains) include a compound according to the chemical formula (IC'):

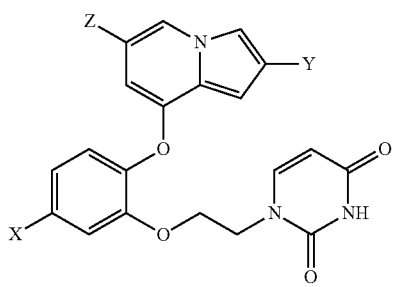

where X is H, Y is CN and Z is H; or
X is H, Y is CN and Z is F; or
X is F, Y is CN and Z is F, or
X is H, Y is CN and Z is Cl, or
a pharmaceutically acceptable salt, solvate or polymorph thereof.

Alternative compounds which also show anti-HIV activity (including against WT and mutant strains) include a compound according to the chemical formula (IIB):

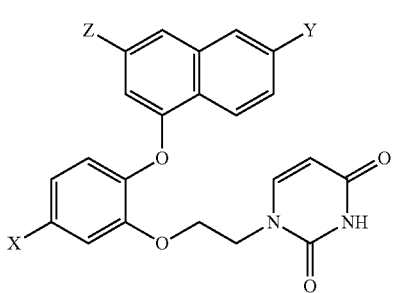

where X is H, Y is H and Z is H; or
X is H, Y is CH$_3$ and Z is H; or
X is H, Y is Cl and Z is H; or
X is H, Y is Cl and Z is Cl; or
X is H, Y is CN and Z is H; or
X is H, Y is CN and Z is Cl; or
X is F, Y is CN and Z is Cl; or
X is C, Y is CN and Z is Cl; or
X is F, Y is CN and Z is H; or
X is Cl, Y is CN and Z is H; or
X is H, Y is CN and Z is F; or
X is F, Y is CN and Z is F; or
X is Cl, Y is CN and Z is F; or
a pharmaceutically acceptable salt, solvate or polymorph thereof.

Preferred compounds according to the above formula IIB which show exceptional anti-HIV activity (including against WT and mutant strains) include compounds where
X is H, Y is CN and Z is H; or
X is F, Y is CN and Z is H; or
X is H, Y is CN and Z is F; or
X is F, Y is CN, and Z is F; or
a pharmaceutically acceptable salt, solvate or polymorph thereof.

In an alternative aspect, the invention provides a pharmaceutical composition comprising an effective amount of at least one compound according to the present invention (e.g, a compound according to formulae (I), (IA-F), (II) and (IIA) (IC') and (IIB) or as otherwise described above), in combination with a pharmaceutically acceptable carrier, additive and/or excipient, optionally in combination with at least one additional anti-HIV agent. Accordingly, pharmaceutical compositions may also include, in addition to the compounds of the present invention as described herein, at least one additional compound, including another anti-HIV agent which inhibits HIV by a mechanism other than through reverse transcriptase inhibition, although other reverse transcriptase inhibitors may be used, especially nucleoside reverse transcriptase inhibitors (NRTIs).

In another embodiment, the present application is directed to a method for inhibiting reverse transcriptase (HIV) comprising exposing reverse transcriptase to at least one compound according to the present invention (e.g., a compound of formulae (I), (IA-F), (II) and (IIA) (IC') and (JIB) or as otherwise described herein), optionally in combination with at least one additional non-nucleoside reverse transcriptase inhibitor (NNRTI) and/or at least one additional nucleoside reverse transcriptase inhibitor (NRTI). The exposure may be in vitro or in vivo (preferably, in vivo).

In yet another embodiment, the present application is directed to the treatment HIV infections and its secondary disease states and conditions, including the treatment of AIDS and ARC, said method comprising administering to a patient in need thereof an effective amount of a pharmaceutical composition comprising any one or more of the compounds according to the present invention (e.g. a compound of formulae (I), (IA-F), (II) and (IIA) (IIC') and (JIB) or as otherwise described herein), optionally in combination (co-administered) with another active agent, preferably another anti-HIV agent as otherwise disclosed herein.

These and other aspects of the invention are described in further detail in the Detailed Description of the Invention.

DETAILED DESCRIPTION OF THE INVENTION

Figure 1:
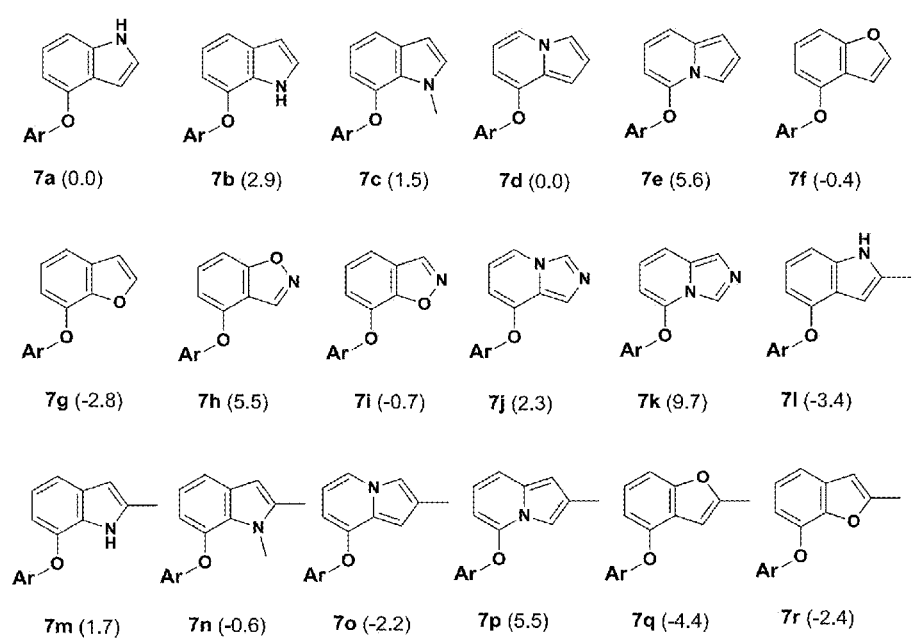
FIG. 1. Modeled compounds where Ar is the uracilylethoxyphenyl substructure of 5 or 6 with R'=Cl. The number in parentheses is the computed relative free energy of binding (kcal/mol) with HIV-RT from the FEP calculations; the statistical uncertainty in the results is ±0.5 kcal/mol.

In accordance with the present invention there may be employed conventional chemical synthetic methods and other biological and pharmaceutical techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "and" and "the" include plural references unless the context clearly dictates otherwise.

Furthermore, the following terms shall have the definitions set out below. It is understood that in the event a specific term is not defined hereinbelow, that term shall have a meaning within its typical use within context by those of ordinary skill in the art.

The term "compound", as used herein, unless otherwise indicated, refers to any specific chemical compound disclosed herein. Within its use in context, the term generally refers to a single compound comprising a hydrophobic moiety and a linker which is capable of reacting and forming a covalent bond with a fusion protein as otherwise described herein. In certain instances the term may also refer to stereoisomers and/or optical isomers (including racemic mixtures) or enantiomerically enriched mixtures of disclosed compounds. Compounds which are disclosed are those which are stable and where a choice of substituents and claim elements is available, the substituent or claim element is chosen such that stable compounds are formed from the disclosed elements and substituents. The symbol ----- in a chemical structure or formula signifies that either a double or single bond may be present between the atoms to which such symbol is attached, depending upon the valence of those atoms and substituents which are on such atoms.

The term "patient" or "subject" is used throughout the specification within context to describe an animal, especially including a domesticated mammal and preferably a human, to whom a treatment or procedure, including a prophylactic treatment or procedure is performed. For treatment of those infections, conditions or disease states which are specific for a specific animal such as a human patient, the term patient refers to that specific animal. In most instances, the patient or subject of the present invention is a domesticated/agricultural animal or human patient of either or both genders.

The term "effective" is used herein, unless otherwise indicated, to describe an amount of a compound or composition which, in context, is used to produce or effect an intended result, whether that result relates to the inhibition of reverse transcriptase or to the inhibition of growth and/or the treatment of HIV or a secondary disease state or conditions such as AIDS or ARC in a patient or subject. The term effective subsumes all other effective amount or effective concentration terms which are otherwise described or used in the present application.

The term "human immunodeficiency virus" shall be used to describe human immunodeficiency virus (HIV) and its infections, which term shall be used to embrace both human immunodeficiency virus 1 (HIV-1) and human immunodeficiency virus 2 (HIV-2). Both wild-type (WT) and mutants of HIV-1 and HIV-2 may be treated with compounds and compositions pursuant to the present invention.

"Hydrocarbon" or "hydrocarbyl" refers to any monovalent (or divalent in the case of alkylene groups) radical containing carbon and hydrogen, which may be straight, branch-chained or cyclic in nature. Hydrocarbons include linear, branched and cyclic hydrocarbons, including alkyl groups, alkylene groups, saturated and unsaturated hydrocarbon groups including aromatic groups both substituted and unsubstituted, alkene groups (containing double bonds between two carbon atoms) and alkyne groups (containing triple bonds between two carbon atoms). In certain instances, the terms substituted alkyl and alkylene are sometimes used synonymously.

"Alkyl" refers to a fully saturated monovalent radical containing carbon and hydrogen, and which may be cyclic, branched or a straight chain. Examples of alkyl groups are methyl, ethyl, n-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_6$ alkyl groups. "Alkylene" refers to a fully saturated hydrocarbon which is divalent (may be linear, branched or cyclic) and which is optionally substituted. Preferred alkylene groups are $C_1$-$C_6$ alkylene groups. Other terms used to indicate substitutent groups in compounds according to the present invention are as conventionally used in the art.

The term "aryl" or "aromatic", in context, refers to a substituted or unsubstituted monovalent aromatic radical having a single ring (e.g., benzene or phenyl). Other examples of aryl groups, in context, may include heterocyclic aromatic ring systems "heteroaryl" groups having one or more nitrogen, oxygen, or sulfur atoms in the ring (5- or 6-membered heterocyclic rings) such as imidazole, furyl, pyrrole, pyridyl, furanyl, thiene, thiazole, pyridine, pyrimidine, pyrazine, triazole, oxazole, among others, which may be substituted or unsubstituted as otherwise described herein.

The term "heterocyclic group" "heterocycle" as used throughout the present specification refers to an aromatic ("heteroaryl") or non-aromatic cyclic group forming the cyclic ring and including at least one and up to three hetero atoms such as nitrogen, sulfur or oxygen among the atoms forming the cyclic ring. The heterocyclic ring may be saturated (heterocyclic) or unsaturated (heteroaryl). Exemplary heterocyclic groups include, for example pyrrolidinyl, piperidinyl, morpholinyl, pyrrole, pyridine, pyridone, pyrimidine, imidazole, thiophene, furan, pyran, thiazole, more preferably pyrimidinyl, pyrrolidinyl, piperidinyl, morpholinyl, oxazole, isoxazole, pyrrole, pyridine, thiophene, thiazole and even more preferably pyrimidinyl, especially uracil or cytosine which are optionally substituted, furyl, 3-methylfuryl, thiazole, piperazinyl, N-methylpiperazinyl, tetrahydropyranyl and 1,4-dioxane, among others. Additional heterocyclic groups include oxazole, benzoxazole, pyrrole, dihydropyrrole, benzopyrrole, benzodihydropyrrole, indole, indolizine, among others.

Preferred heterocyclic groups $R_p$ are less than fully saturated and more preferably are pyrimidine groups, especially including uracil or cytosine groups which may be substituted at the 5- or 6-position (especially the 5-position) of the pyrimidine ring, especially 5-substituted uracil or cytosine groups according to the chemical structure:

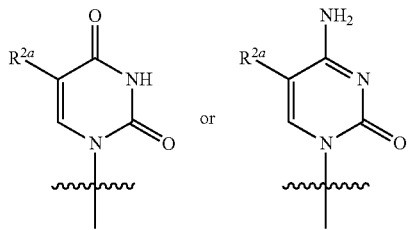

Where $R^{2a}$ is H, halogen (preferably F, Cl or Br), optionally substituted $C_1$-$C_3$ alkyl (preferably methyl, ethyl or trifluoromethyl), optionally substituted —O—($C_1$-$C_3$) alkyl (methyl, ethyl, propyl, isopropyl), including O—$CF_3$, CN.

Exemplary heteroaryl moieties which may be used in the present invention include for example, pyrrolyl, pyridinyl, pyridonyl, pyridazinyl, pyrimidinyl, pyrazinyl, pyrazolyl, imidazolyl, triazolyl, tetrazolyl, oxadiazolyl, sulfur-containing aromatic heterocycles such as thiophene (thienyl); oxygen-containing aromatic heterocycles such as furanyl and pyranyl, and including aromatic heterocycles comprising 2 or more hetero atoms selected from among nitrogen, sulfur and oxygen, such as thiazolyl, thiadiazolyl, isothiazolyl, isoxazolyl, furazanyl and oxazolyl. Further heteroaryl groups may include pyridinyl, triazinyl, pyridonyl, pyrimidinyl, imidazolyl, furanyl, pyranyl, thiazolyl. Pyrimidine groups, especially uracil and cytosine, optionally substituted, are preferred.

The term "substituted" shall mean substituted at a carbon (or nitrogen) position within context, hydroxyl, carboxyl, cyano (C≡N), nitro ($NO_2$), halogen (preferably, 1, 2 or 3 halogens, especially on an alkyl, especially a methyl group such as a trifluoromethyl), alkyl group (preferably, $C_1$-$C_{10}$, more preferably, $C_1$-$C_6$), alkoxy group (preferably, $C_1$-$C_6$ alkyl or aryl, including phenyl and substituted phenyl), ester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), nitro or amine (including a five- or six-membered cyclic alkylene amine, further including a $C_1$-$C_6$ alkyl amine or $C_1$-$C_6$ dialkyl amine which alkyl groups may be substituted with one or two hydroxyl groups), amido, which is preferably substituted with one or two $C_1$-$C_6$ alkyl groups (including a carboxamide which is substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Preferably, the term "substituted" shall mean within its context of use alkyl, alkoxy, halogen, ester, keto, nitro, cyano and amine (especially including mono- or di-$C_1$-$C_6$ alkyl substituted amines which may be optionally substituted with one or two hydroxyl groups). Any substitutable position in a compound according to the present invention may be substituted in the present invention, but no more than 3, more preferably no more than 2 substituents (in some instances only 1 or no substituents) is present on a ring. Preferably, the term "unsubstituted" shall mean substituted with one or more H atoms.

The term "human immunodeficiency virus" shall be used to describe human immunodeficiency virus I (HIV 1 and 2), the growth or replication of which may be inhibited or disease states of which may be treated using one or more methods according to the present invention. Viruses which may be treated according to the present invention include, for example, human immunodeficiency viruses 1 and 2 (HIV-1 and HIV-2), among others. The term HIV includes mutant strains of HIV including "drug resistant" or "multiple drug resistant" strains of the HIV virus which have mutated to be resistant to one or more clinically approved anti-HIV agents, including, in particular, HIV strains which are resistant to one or more NRTI compounds and/or NNRTI compounds. Exemplary HIV drug resistant strains which may be effectively treated using compounds according to the present invention include the following, among others: (defined by RT mutation)—K65R, Y115F, F116Y, Q151M, M184V, L74V, V75T, T215Y, K103N, T215Y/M184V, 5705-72 (5705.72), L100I, K101E, K103N, V106A, D110E, V179D, Y181C, D185E, D186E, Y188H, G190E, E138K, M41L, D67N, K70R, T215Y/F, K219Q/E, Y181C, K103N, L100I, Y188C/H among others, especially Y181C and/or K103N/Y181C, among others.

The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

A Category 1 HIV infection is characterized by the patient or subject being HIV positive, asymptomatic (no symptoms) and having never had fewer than 500 CD4 cells. If the patient has had any of the AIDS-defining diseases listed for categories 2 (ARC) or 3 (AIDS), then the patient is not in this category. If the patient's t-cell count has ever dropped below 500, that patient is considered either Category 2 (ARC) or Category 3 (AIDS).

A category 2 (ARC) infection is characterized by the following criteria: The patient's T-cells have dropped below 500 but never below 200, and that patient has never had any Category 3 diseases (as set forth below) but have had at least one of the following defining illnesses:
  Bacillary angiomatosis
  Candidiasis, oropharyngeal (thrush)
  Candidiasis, vulvovaginal; persistent, frequent, or poorly responsive to therapy
  Cervical dysplasia (moderate or severe)/cervical carcinoma in situ
  Constitutional symptoms, such as fever (38.5 C) or diarrhea lasting longer than 1 month
  Hairy leukoplakia, oral
  Herpes zoster (shingles), involving at least two distinct episodes or more than one dermatome
  Idiopathic thrombocytopenic purpura
  Listeriosis
  Pelvic inflammatory disease, particularly if complicated by tubo-ovarian abscess
  Peripheral neuropathy According to the U.S. government, in Category 2 ARC, the immune system shows some signs of damage but it isn't life-threatening.

A Category 3 (AIDS) infection is characterized by the following criteria:
  T-cells have dropped below 200 or
  Patent has (has had) at least one of the following defining illnesses—
    Candidiasis of bronchi, trachea, or lungs
    Candidiasis, esophageal
    Cervical cancer, invasive**
    Coccidioidomycosis, disseminated or extrapulmonary
    Cryptococcosis, extrapulmonary
    Cryptosporidiosis, chronic intestinal (greater than 1 month's duration)
    Cytomegalovirus disease (other than liver, spleen, or nodes)
    Cytomegalovirus retinitis (with loss of vision)
    Encephalopathy, HIV-related
    Herpes simplex: chronic ulcer(s) (greater than 1 month's duration); or bronchitis, pneumonitis, or esophagitis
    Histoplasmosis, disseminated or extrapulmonary
    Isosporiasis, chronic intestinal (greater than 1 month's duration)
    Kaposi's sarcoma
    Lymphoma, Burkitt's (or equivalent term)
    Lymphoma, immunoblastic (or equivalent term)
    Lymphoma, primary, of brain
    *Mycobacterium avium* complex or *M. kansasii*, disseminated or extrapulmonary
    *Mycobacterium tuberculosis*, any site (pulmonary** or extrapulmonary)
    *Mycobacterium*, other species or unidentified species, disseminated or extrapulmonary
    *Pneumocystis carinii* pneumonia
    Pneumonia, recurrent**
    Progressive multifocal leukoencephalopathy
    *Salmonella* septicemia, recurrent
    Toxoplasmosis of brain
    Wasting syndrome due to HIV The term "pharmaceutically acceptable" refers to a carrier, additive or excipient which is not unacceptably toxic to the subject to which it is administered. Pharmaceutically acceptable excipients are described at length by E. W. Martin, in "Remington's Pharmaceutical Sciences", among others well-known in the art.

A "pharmaceutically acceptable salt" of the present compound generally refers to pharmaceutically acceptable salts form of a compound which can form a salt, because of the existence of for example, amine groups, carboxylic acid groups or other groups which can be ionized in a sample acid-base reaction. A pharmaceutically acceptable salt of an amine compound, such as those contemplated in the current invention, include, for example, ammonium salts having as counterion an inorganic anion such as chloride, bromide, iodide, sulfate, sulfite, nitrate, nitrite, phosphate, and the like, or an organic anion such as acetate, malonate, pyruvate, propionate, fumarate, cinnamate, tosylate, and the like. Certain compounds according to the present invention which have carboxylic acid groups or other acidic groups which may form pharmaceutically acceptable salts, for example, as carboxylate salts, are also contemplated by the present invention.

Aspects of the present invention include compounds which have been described in detail hereinabove or to pharmaceutical compositions which comprise an effective amount of one or more compounds according to the present invention, optionally in combination with a pharmaceutically acceptable carrier, additive or excipient.

The term "pharmaceutically acceptable derivative" is used throughout the specification to describe any pharmaceutically acceptable prodrug form (such as an ester or ether or other prodrug group) which, upon administration to a patient, provides directly or indirectly the present compound or an active metabolite of the present compound.

The term "inhibitory effective concentration" or "inhibitory effective amount" is used throughout the specification to describe concentrations or amounts of compounds according to the present invention which substantially or significantly inhibit the growth or replication of susceptible viruses, especially including human immunodeficiency viruses 1 and 2 (HIV-1 and HIV-2).

The term "preventing effective amount" is used throughout the specification to describe concentrations or amounts of compounds according to the present invention which are prophylactically effective in preventing, reducing the likelihood of infection or delaying the onset of infections in patients caused by human immunodeficiency viruses 1 and 2 (HIV-1 and HIV-2) and other viruses. The terms inhibitory effective amount or preventive effective amount also generally fall under the rubric "effective amount".

The term "co-administration" is used to describe the administration of two or more active compounds, in this case a compound according to the present invention, in combination with an additional anti-HIV agent or other biologically active agent, in effective amounts. Although the term coadministration preferably includes the administration of two or more active compounds to the patient at the same time, it is not necessary that the compounds actually be administered at the exact same time, only that amounts of compound will be administered to a patient or subject such that effective concentrations are found in the blood, serum or plasma, or in the pulmonary tissue at the same time.

Compounds according to the present invention may be administered with one or more anti-viral agent, including other anti-HIV agents including nucleoside reverse transcriptase inhibitors (NRTI), other non-nucleoside reverse transcriptase inhibitors (i.e., those which are not representative of the present invention), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C (Elvucitabine), ETR (etravirine), Edurant (rilpivirine), Festinavir, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other agents which may be used in coadministration with compounds according to the present invention include, for example, other NNRTI's (i.e., other than the NNRTI's according to the present invention) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxycarbonyl)phenyl)hept-1-enyl)-2-methoxybenzoate (Alkenyldiarylmethane analog, Adam analog), 5Cl3PhS-2IndolCONH2 (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-Cyano-2-indoyly)carbonyl]-4-[3-(isopropylamino)-2-pyridinyl]piperazine (piperazine1 pyridine 4 indolyl derivative), 1-[5-[[N-(methyl)methylsulfonylamino]-2-indolylcarbonyl-4-[3-(isopropylamino)-2-pyridinyl] piperazine (piperazine 1pyridine 5 indolyl derivative), 1-[3-(Ethylamino)-2-[pyridinyl]-4-[(5-hydroxy-2-indolyl) carbonyl]piperazine, 1-[(6-Formyl-2-indoyly)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione (2-Pyridinone 3pyrid 3MeNH Derivative), R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

Co-administration also includes the administration of other non anti-viral agents which may be beneficial for patients with HIV, AIDS or ARC or other secondary disease states or conditions of patients with HIV infections.

Compounds according to the present invention may be used in pharmaceutical compositions having biological/pharmacological activity for the treatment of, for example, viral infections, as well as a number of other conditions and/or disease states which may appear or occur secondary to the viral infection. These compositions comprise an effective amount of any one or more of the compounds disclosed hereinabove, optionally in combination with a pharmaceutically acceptable additive, carrier or excipient. Compounds according to the present invention may also be used as intermediates in the synthesis of compounds exhibiting biological activity as well as standards for determining the biological activity of the present compounds as well as other biologically active compounds.

The compositions of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, transdermally, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. The present compounds may also be formulated for vaginal administration.

Topical application for the lower intestinal tract can be effected in a rectal suppository formulation (see above) or in a suitable enema formulation. Topically administered transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound of the instant invention that may be combined with the carrier materials to produce a single dosage form will vary depending upon the host treated, the particular mode of administration. Preferably, the compositions should be formulated so that a dosage of between about 0.01 and 150, preferably about 0.5 to about 25 mg/kg of patient/day of the novel compound can be administered to a patient receiving these compositions.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.25 milligram to about 1 gram, more preferably about 1 milligram to about 750 milligrams, and even more preferably about 10 milligrams to about 500-600 milligrams of active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free compounds hynor prodrug forms of the compounds according to the present invention.

In particularly preferred embodiments according to the present invention, the compounds and compositions are used to treat, prevent or delay the onset of viral infections of mammals and in particular HIV 1 and 2 infections in humans. Preferably, to treat, prevent or delay the onset of a viral infection, the compositions will be administered in oral dosage form in amounts ranging from about 250 micrograms up to about 500 mg or more at least once a day, preferably, up to four times a day, within the dosage range used for therapeutic treatment. The present compounds are preferably administered orally, but may be administered parenterally, topically, in suppository or other form. Compounds according to the present invention may also be used to reduce the likelihood that a HIV infection may worsen into AIDS or ARC symptoms and/or secondary disease states and/or conditions.

Certain compounds according to the present invention, because of their low toxicity to host cells, may advantageously be employed prophylactically to prevent (reduce the likelihood of) a viral infection or to prevent the occurrence of clinical symptoms associated with the viral infection, for example AIDS or ARC secondary to HIV. Thus, the present invention also encompasses methods for the prophylactic treatment (preventing, reducing the likelihood or delaying the onset) of viral infections, and in particular HIV and conditions which occur secondary to those virus infections. In this aspect according to the present invention, the present compositions are used to prevent reduce the likelihood of or delay the onset of a viral infection, in particular, HIV or a virus related disease or condition such as AIDS or ARC.

This prophylactic method comprises administering to a patient in need of such treatment or who is at risk for the development of an HIV or other viral infection or a disease state or condition which occurs secondary to an HIV infection, an amount of a compound according to the present invention effective for alleviating, preventing or delaying the onset of the viral infection or secondary condition or disease state. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In the case of compounds of the present invention for the prophylactic treatment of viral infections, these compounds may be administered within the same dosage range for therapeutic treatment (as described hereinabove, as a prophylactic agent to prevent the proliferation of the viral infection or alternatively, to prolong the onset of or reduce the likelihood of a patient contracting a virus infection which manifests itself in clinical symptoms.

In addition, compounds according to the present invention may be administered alone or in combination with other agents, including other compounds of the present invention.

Certain compounds according to the present invention may be effective for enhancing the biological activity of certain agents according to the present invention by reducing the metabolism, catabolism or inactivation of other compounds and as such, are co-administered for this intended effect.

As indicated, compounds according to the present invention may be administered alone or in combination with other anti-viral agents for the treatment of a virus infection as otherwise described herein, especially including other compounds of the present invention or compounds which are otherwise disclosed as being useful for the treatment of HIV, including those presently used to treat HIV such as nucleoside reverse transcriptase inhibitors (NRTI), other non-nucleoside reverse transcriptase inhibitors, protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-D4FC, NVP (Nevirapine), DLV (Delavirdine), EFV (Efavirenz), ETR (etravirine), Edurant (rilpivirine), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development, among others as well as compounds which are disclosed in inter alia, U.S. Pat. Nos. 6,240,690; 6,316,505; 6,316,492; 6,232,120; 6,180,604; 6,114,327; 5,891,874; 5,821,242; 5,532,215; 5,491,135; 5,179,084; and 4,880,784, among others, relevant portions of which are incorporated by reference herein.

The compounds disclosed in the above-referenced patents may be used in combination with the present compounds for their additive activity or treatment profile against HIV and/or other viruses and in certain instances, for their synergistic effects in combination with compounds of the present invention. Preferred secondary or additional compounds for use with the present compounds are those which do not inhibit HIV or another virus. Certain compounds according to the present invention may be effective for enhancing the biological activity of certain agents according to the present invention by reducing the metabolism or inactivation of other compounds and as such, are co-administered for this intended effect.

Compounds according to the present invention may be used as active agents in pharmaceutical compositions as inhibitors of reverse transcriptase and as anti-viral agents, said compositions comprising an effective amount of one or more of the compounds disclosed above, formulated as a pharmaceutical dosage form, optionally in combination with a pharmaceutically acceptable carrier, additive or excipient. Pharmaceutical compositions according to the present invention may be used in the treatment of HIV infections (all forms, including human immunodeficiency virus I and II), and numerous additional viral infections, especially including drug resistant forms of these viruses.

In other aspects of the present invention, certain compounds according to the present invention may be used as antagonists in binding assays, as analytical agents, as agents to be used to isolate or purify proteins (especially viral reverse transcriptase), and/or as intermediates in the synthesis of further agents, among other uses.

Novel Nanomolar and Picomolar Inhibitors of HIV Reverse Transcriptase

The analog of 3 with the CV group truncated to just cyano has an $EC_{50}$ of 14 nM towards the WT virus, and other compounds with the cyano of the CV group replaced by

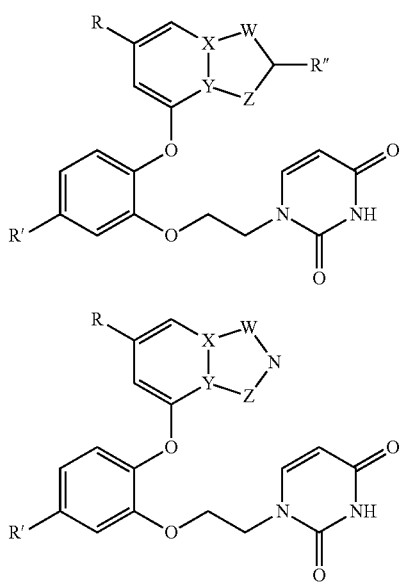

chlorine, $OCH_3$, or $CONH_2$ showed 100 to 1000-fold losses in activity. These findings are consistent with the modeling and crystallography,[9,10] which document (a) close contact between the CV group and Trp229 in the NNRTI binding site, and (b) projection of the cyano group into the "tunnel" heading towards the polymerase active site with a water molecule hydrogen bonded to the cyano nitrogen atom. In order to replace these features and keeping in mind space constraints, it was decided to consider 6:5 heterobicyclic possibilities as indicated by 5 and 6. In 5, R" would likely be cyano, while in 6 the azole nitrogen would retain a hydrogen bond accepting site for a water molecule. In both cases, the choice of heteroatoms in the five-membered ring for optimal interaction with Trp229 was not obvious, nor was the effect of loss of the torsional degree of freedom associated with the CV group. In view of the wide range of options and the anticipated synthetic challenges, guidance was sought from computational analyses, specifically free energy perturbation calculations to predict relative free energies of binding for many alternatives.

Computational Design

The computational procedures that were utilized are exactly the same as in earlier studies.[9,14] Starting from a crystal structure of the protein, the BOMB program[7] was used to build initial structures for the desired protein-ligand complexes. Conjugate-gradient energy minimizations were performed to relax the structures and Monte Carlo free-energy perturbation (MC/FEP) were carried out to compute relative free energies of binding. The calculations were performed with the MCPRO program[15] using the OPLS-AA force field for the protein,[16] OPLS/CM1A for the ligands,[17] and the TIP4P water model.[18] The FEP calculations used 11 windows of simple overlap sampling, and many were also checked using 14 windows of double-wide sampling.[19] The typical difference between the results was about 0.5 kcal/mol, which is a good measure of the statistical uncertainties. When both procedures were executed, the average of the results is reported. Each window covered at least 10 million configurations of equilibration and 10 million configurations of averaging. The unbound ligands and complexes were solvated in water caps with a 25-Å radius, amounting to ca. 2000 and 1250 water molecules, respectively. The 175 amino acid residues nearest to the ligand were included in the model for the complexes. A residue-based cutoff for non-bonded interactions was invoked at 10 Å. After short conjugate-gradient optimizations, the backbone atoms of the protein were not moved. The ligand and side chains with any atom within ca. 10 Å of the ligand were fully sampled. All water molecules were sampled using translations and rigid rotations.

The alternative heterocycles that were considered are designated 7a-7k in FIG. 1. They are typical 6:5 fused-ring possibilities, namely, indoles, indolizines, benzofurans, benzisoxazoles, and imidazopyridines. 7a, 7d, 7e, and 7b represent a 'nitrogen walk' around the 5-membered ring; the remaining isoindole isomer was excluded as such structures are labile.[20]

Furthermore, benzothiophenes were not considered as they appeared less promising in initial structure building than the benzofurans, and they are both prone to have metabolic liabilities.[8] It was also anticipated that a substituent R" would be utilized as indicated in 5, so the methylated analogs 7l-7r were modeled.

Figure 2:
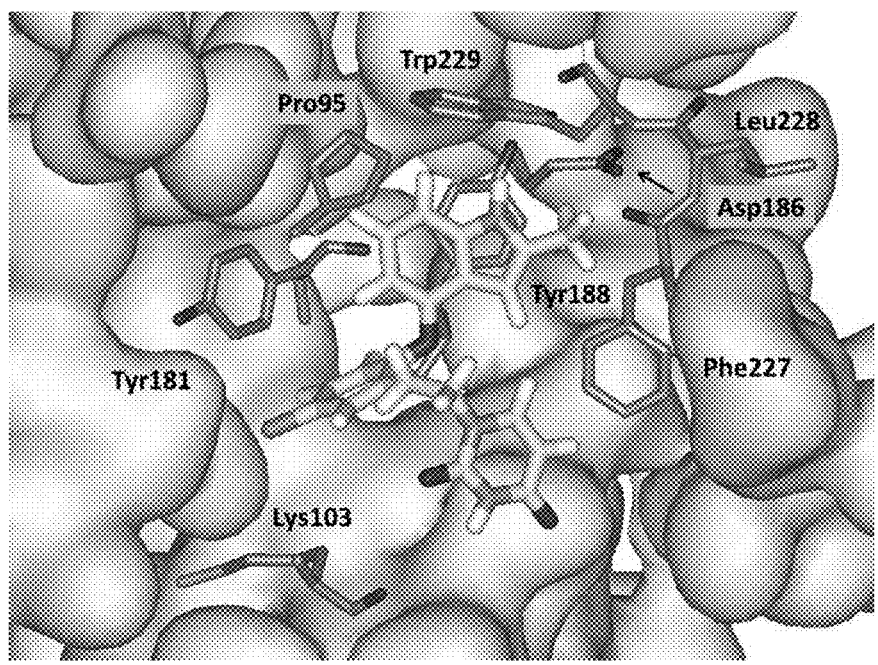
FIG. 2. Illustration of a configuration from an MC simulation of the indole 7l bound to wild type HIV-1 reverse transcriptase. Carbon atoms of 7l are rendered in yellow. All water molecules and many residues in front of the ligand have been removed for clarity.

The structural situation is exemplified for the complex of 7l in FIG. 2. The expectation from the modeling for 7a-7r and the crystallography for 3 and 4,[10] assuming 7l would bind at all, is that the indole fragment would make π contacts face-to-face with Tyr188 and edge-to-face with Tyr181 and Trp229. In addition, the methyl group or another substituent at C2 would project below the Phe227-Leu228-Trp229 loop into the tunnel heading towards the polymerase active site. The tunnel contains water molecules; however, the pocket below C3 of the indole is dry. Consequently, heterocycles with an unsaturated nitrogen in the C3 position, e.g., the benzimidazole corresponding to 7a or benzoxazole corresponding to 7f, were not considered. There is also no water in the small pocket between Pro95 and Tyr188. Thus, introductions of nitrogen atoms into the three possible sites for the six-membered ring were not evaluated.

The results of the MC/FEP calculations are summarized in FIG. 1. Many of the perturbations were made from 7a, which is taken as the reference compound for the listed relative free energies of binding, $\Delta\Delta G_b$. For methylated compounds, the perturbations were made to the desmethyl analog, e.g., 7m to 7b. One can attempt to rationalize the results after the fact, but even correct qualitative predictions in the absence of the computations are elusive owing to the numerous interactions involved. For example, it might seem to be unsurprising that 7b is computed to be less well bound than 7a since there is no water in the pocket for a hydrogen bond with the indole NH of 7b. However, the indole NH of 7a is also not able to participate in a hydrogen bond and the favorability of the electrostatic interactions with Trp229 and Tyr188 are unclear. The methylated 7c does bind better than 7b since the methyl group is placed in the pocket, though whether or not there is enough room is unclear without the result. The strong preference for the indolizine 7d over its isomer 7e is striking and must reflect electrostatic differences, which have arisen before for indolizine derivatives.[21] Similarly, 7g is preferred over 7f. Furans are very poor hydrogen-bond acceptors, so the pattern is that it is beneficial to have a more acidic (positive) hydrogen near the tryptophan ring (7a, 7d, 7g) than a more electron rich atom. Continuing, introduction of a nitrogen atom at C2 of the 5-membered ring turned out to be detrimental in each case, 7h-7k, by ca. 3 kcal/mol. In the MC simulations it is found that water in the tunnel does not penetrate past the Phe227-Trp229 loop, so a hydrogen bond with water is not made to the 2-position nitrogen atom. Thus, it appears that a cyano group at this position is needed to reach a water molecule in the tunnel.

Finally, the results for introduction of a methyl group at C2 to yield 7l-7r were interesting. In some cases, there is significant benefit, e.g., 7a going to 7l, while in others there is little change (7e to 7p, or 7g to 7r). In analyzing this, it appears that a key factor is the angle of projection of the methyl group into the tunnel. For 7l in the snapshot in FIG. 2 the NH—C2-CH$_3$ bond angle is 116° and the methyl group is directed upward above C$_\alpha$ of Phe227. The corresponding angle (C3-C2-CH$_3$) in snapshots for 7m is near 130°, which brings the methyl group too close to the C$_\alpha$ atom. When 2-methylindole is optimized with OPLS/CM1A the corresponding angles are 120.1° and 130.2°. With ab initio calculations at the HF/6-311G(d) level the results are 120.6° and 130.2°, and with MP2/6-311G(d) optimizations they are 121.0° and 130.5°.[22] For 2-methylbenzofuran, the O—C2-CH$_3$ and C3-C2-CH$_3$ angles are computed to be 118.3° and 129.7° with OPLS/CM1A. Thus, 7f benefits from addition of the methyl group in going to 7q, while the addition of the methyl group to 7g to give 7r is predicted to reduce the binding affinity. This reverses the preference for 7g over 7f.

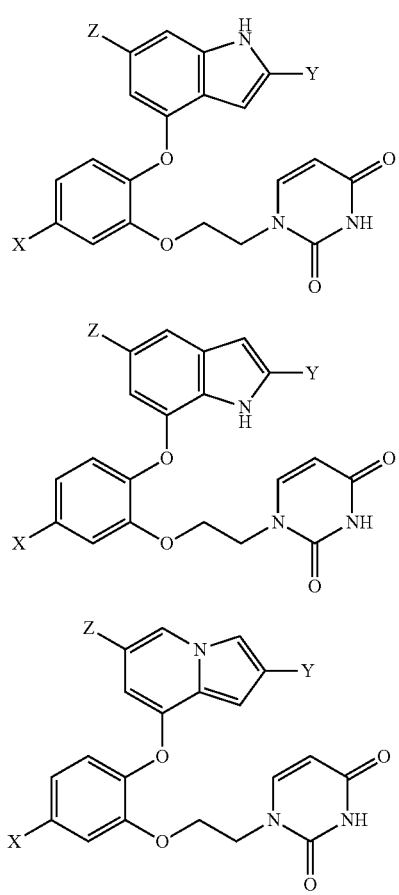

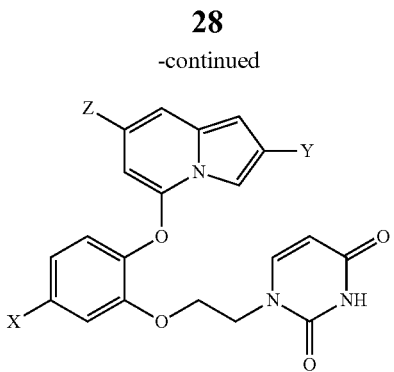

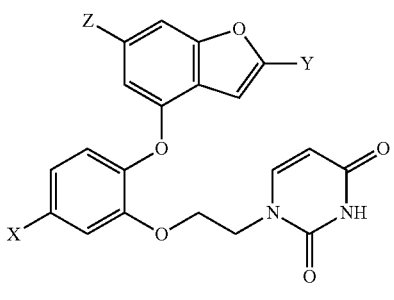

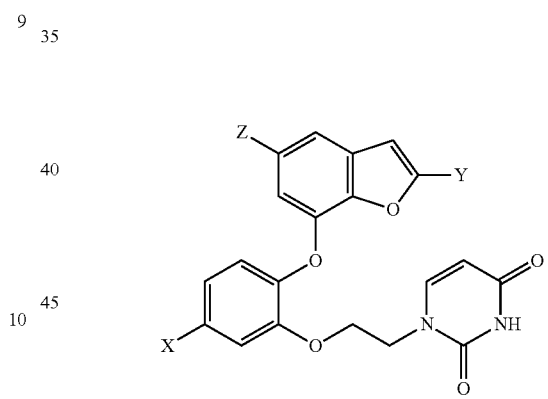

Synthetic Chemistry

Based on the MC/FEP results in FIG. 1, the synthetic efforts were directed at substituted indoles, indolizines, and benzofurans corresponding to 8, 10, and 12. A few of the isomers 9, 11, and 13 were also prepared. A list of analogs that were synthesized is given in Table 1, below.

TABLE 1

Inhibitory Activity (EC$_{50}$) for HIV-1 and Cytotoxicity (CC$_{50}$) in μM

| Compd | X | Y | Z | WT EC$_{50}$[a] | Y181C EC$_{50}$[a] | 103N181C EC$_{50}$[a] | CC$_{50}$[b] |
|---|---|---|---|---|---|---|---|
| 3 | | | | 0.000055 | 0.049 | 0.220 | 10 |
| 4 | | | | 0.00032 | 0.016 | 0.085 | 45 |

TABLE 1-continued

Inhibitory Activity ($EC_{50}$) for HIV-1 and Cytotoxicity ($CC_{50}$) in μM

| Compd | X | Y | Z | WT $EC_{50}{}^a$ | Y181C $EC_{50}{}^a$ | 103N181C $EC_{50}{}^a$ | $CC_{50}{}^b$ |
|---|---|---|---|---|---|---|---|
| 8a | H | H | H | 0.085 | ND | ND | 53 |
| 8b | Cl | H | H | 1.6 | NA | NA | 18 |
| 8c | H | $CH_3$ | H | 0.39 | NA | NA | 15 |
| 8d | H | CN | H | 0.056 | 38 | 5.5 | 72 |
| 8e | H | CN | $CH_3$ | 0.010 | NA | 0.80 | 1.2 |
| 8f | H | CN | Cl | 0.34 | 27 | 2.7 | 81 |
| 9a | H | H | $CH_3$ | 6.0 | ND | ND | >100 |
| 9b | H | $CH_3$ | H | NA | NA | NA | 17 |
| 10a | H | $CH_3$ | H | 0.050 | ND | ND | 9.0 |
| 10b | H | CN | H | 0.00038 | 0.31 | 0.011 | >100 |
| 10c | H | CN | $CH_3$ | 0.00090 | 0.80 | 0.032 | 3.0 |
| 10d | H | CN | F | 0.00070 | 0.17 | 0.068 | 40 |
| 10e | H | CN | Cl | 0.0037 | 0.22 | 0.022 | 39 |
| 10f | F | CN | H | 0.0027 | 0.60 | 0.22 | 100 |
| 10g | F | CN | $CH_3$ | 0.0020 | 0.40 | 0.25 | 17 |
| 10h | F | CN | F | 0.00040 | 0.25 | 0.010 | 50 |
| 10i | F | CN | Cl | 0.0025 | 0.16 | 0.11 | 15 |
| 10j | 4-F | CN | H | 0.0020 | 9.0 | 0.22 | 35 |
| 10k | 4,5-diF | CN | H | 0.0032 | 1.2 | 0.50 | 19 |
| 10l | 4,5-diF | CN | F | 0.0068 | 1.2 | 0.23 | 54 |
| 10m | Cl | CN | H | 0.0051 | 1.8 | 0.90 | 55 |
| 10n | Cl | CN | Cl | 0.022 | 0.41 | 0.53 | 20 |
| 11a | F | CN | H | 0.017 | 6.9 | 1.3 | >100 |
| 12a | H | CN | H | 0.018 | NA | 0.42 | >100 |
| 12b | H | CN | $CH_3$ | 0.21 | NA | 1.3 | >100 |
| 12c | H | CN | Cl | 0.019 | 1.9 | 0.26 | >100 |
| 12d | F | CN | H | 0.040 | 3.5 | 4.0 | >100 |
| 12e | F | CN | $CH_3$ | 0.26 | NA | 5 | >100 |
| 12f | Cl | H | H | 0.800 | ND | ND | 19 |
| 12g | Cl | $CH_3$ | H | 0.025 | NA | NA | 8.0 |
| 12h | Cl | CN | H | 0.0070 | NA | NA | 7.0 |
| 13a | Cl | H | H | 0.900 | ND | ND | 50 |
| nevirapine | | | | 0.11 | NA | NA | >100 |
| efavirenz | | | | 0.002 | 0.010 | 0.030 | 15 |
| etravirine | | | | 0.001 | 0.008 | 0.005 | 11 |
| rilpivirine | | | | 0.00067 | 0.00065 | 0.002 | 8 |

$^a$For 50% protection in MT-2 cells; antiviral curves used triplicate samples at each concentration.
ND for not measured.
NA for $EC_{50} > CC_{50}$.
$^b$For 50% inhibition of MT-2 cell growth; toxicity curves also used triplicate samples.

While complete synthetic details and compound characterization are provided in the Supplementary Information, the synthetic routes for the key compounds with a cyano group in the 2-position of the bicyclic heterocycle are summarized here. The identity of all compounds was confirmed by $^1$H and $^{13}$C NMR and high-resolution mass spectrometry; purity was >95% as judged by high-performance liquid chromatography.

For the 2-cyanoindoles 8 (Y=CN), the pathway is illustrated in Scheme 1. The syntheses began with an $S_NAr$ reaction between a 2-fluorobenzaldehyde and a 2-benzyloxyphenol to yield the phenoxybenzaldehyde scaffold.[23] Cyclization to the indole was achieved using methyl azidoacetate,[24] which was followed by reduction of the ester to the alcohol, and then oxidation to the aldehyde.[25] After conversion of the aldehyde at C2 to the desired nitrile[26] and Boc-protection of the indole nitrogen, the benzyl group was cleaved. To install the uracil containing side chain, the phenol was unmasked and alkylated with 3-benzoyl,1-bromoethyluracil. Finally, the Boc group was removed with tetra-n-butylammonium fluoride, and the uracil moiety was deprotected under basic conditions to afford the desired products. It may be noted that alternatives to the Boc-protection were considered via addition of methyl chloroformate or triisopropylsilyl chloride; however, in these cases, the deprotection step proved difficult.

For the indolizines 10 (Y=CN), comparatively easy installation of the desired cyano group at the 2-position was possible using acrylonitrile in the cyclization sequence,[27] as summarized in Scheme 2. The resultant 8-bromo-2-cyanoindolizines underwent an $S_NAr$ reaction with a substituted 2-methoxyphenol to yield the diarylethers. Installation of the uracilylethoxy side chain then proceeded as in Scheme 1, following demethylation of the methoxy group with $BBr_3$. The starting picolinaldehydes were obtained either by DIBALH reduction of the corresponding 2-methylester or $SeO_2$ oxidation of the 2-methyl analog when Z was chlorine.

Scheme 1. Synthesis of the 2-Cyanoindoles
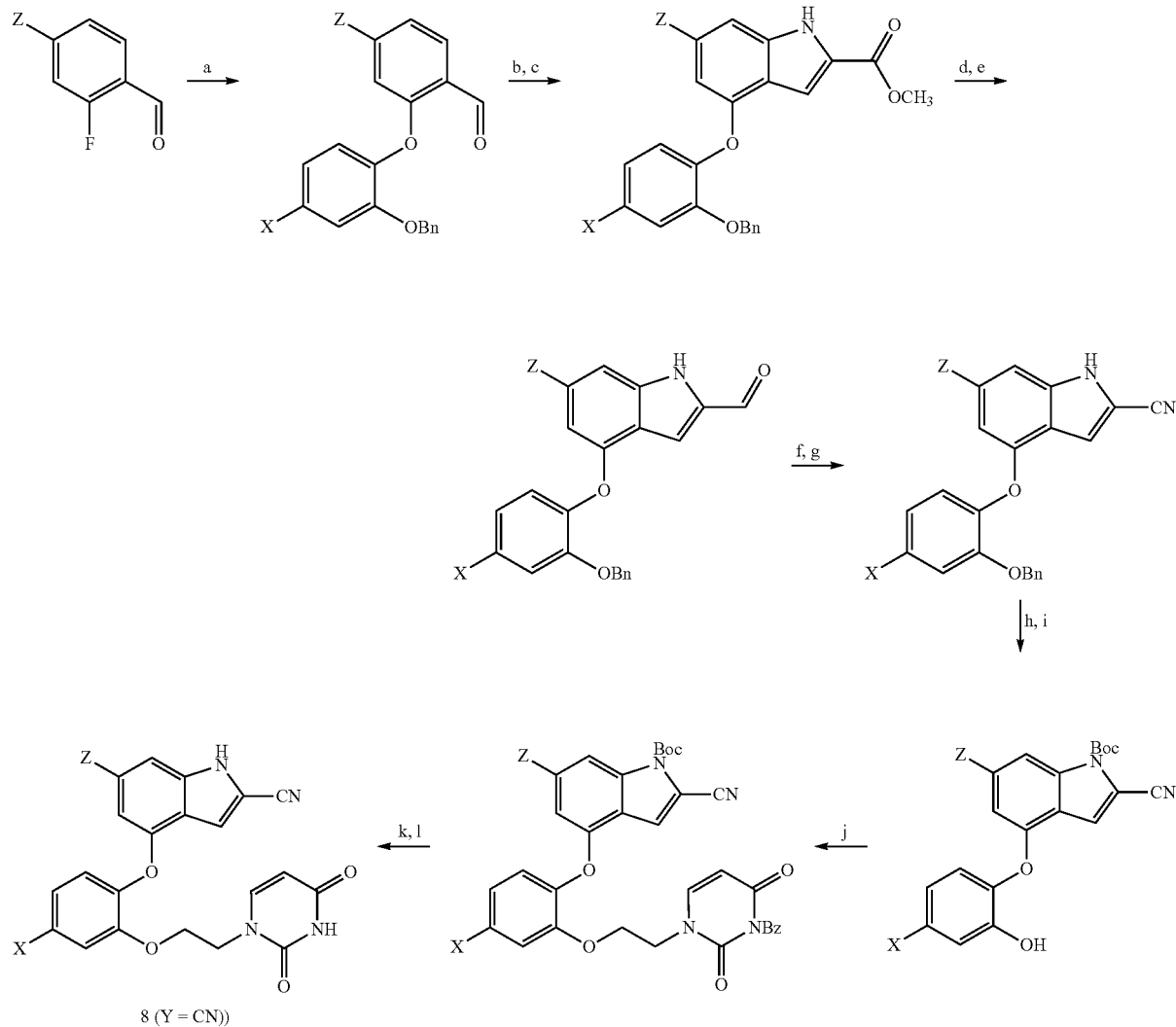
Reagents: (a) K$_2$CO$_3$, DMF, 100-120° C., 12 h; (b) methyl azidoacetate, −40° C., NaOMe, MeOH, 12 h; (c) xylene, reflux, 4 h; (d) LAH, THF, 0° C., 0.5 h; (e) MnO$_2$, DCM, rt, 24 h; (f) NH$_2$OSO$_3$H, MeOH, reflux, 0.5 h; (g) Cu(OAc)$_2$, CH$_3$CN, reflux, 1 h; (h) 4-DMAP, Boc$_2$O, THF, rt, 12 h; (i) H$_2$/Pd/C, MeOH, rt, 0.5 h; (j) 3-benzoyl,1-bromoethyluracil, K$_2$CO$_3$, DMF, 60° C., 2 h; (k) TBAF, THF, reflux, 24 h; (l) NH$_3$, MeOH, rt, 12 h.
Scheme 2. Synthesis of the 2-Cyanoindolizines
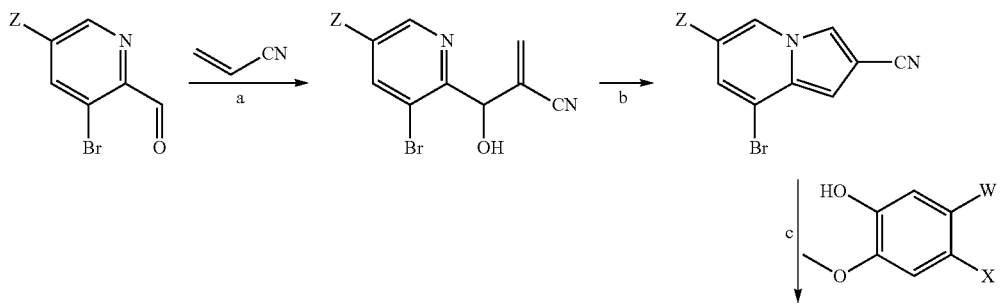

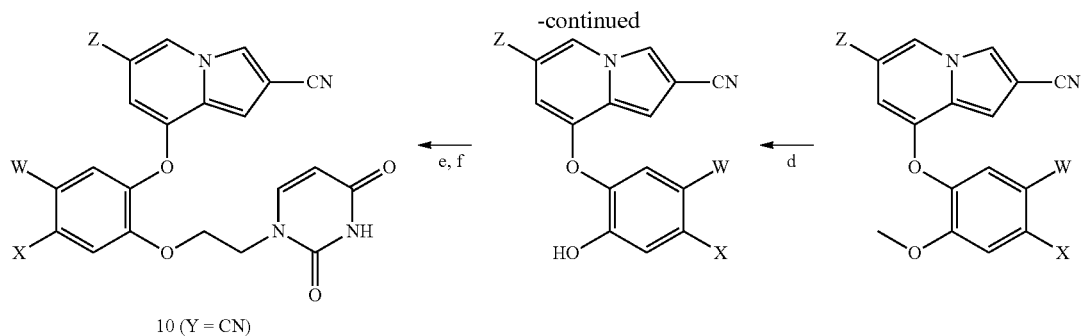

10 (Y = CN)

Reagents: (a) DABCO, neat, 2 h; (b) $Ac_2O$, 100° C., 2 h→140° C., 16 h; (c) CuI, $Cs_2CO_3$, 2,2,6,6-tetramethyl-3,5-heptanedione, dioxane, 120° C., 18 h; (d) $BBr_3$, DCM, −78° C.→0° C., 3 h; (e) 3-benzoyl,1-bromoethyluracil, $Cs_2CO_3$ or $K_2CO_3$, DMF, 60° C., 3 h; (f) $NH_4OH$, DCM, 16 h.

Scheme 3. Synthesis of the 2-Cyanobenzofurans

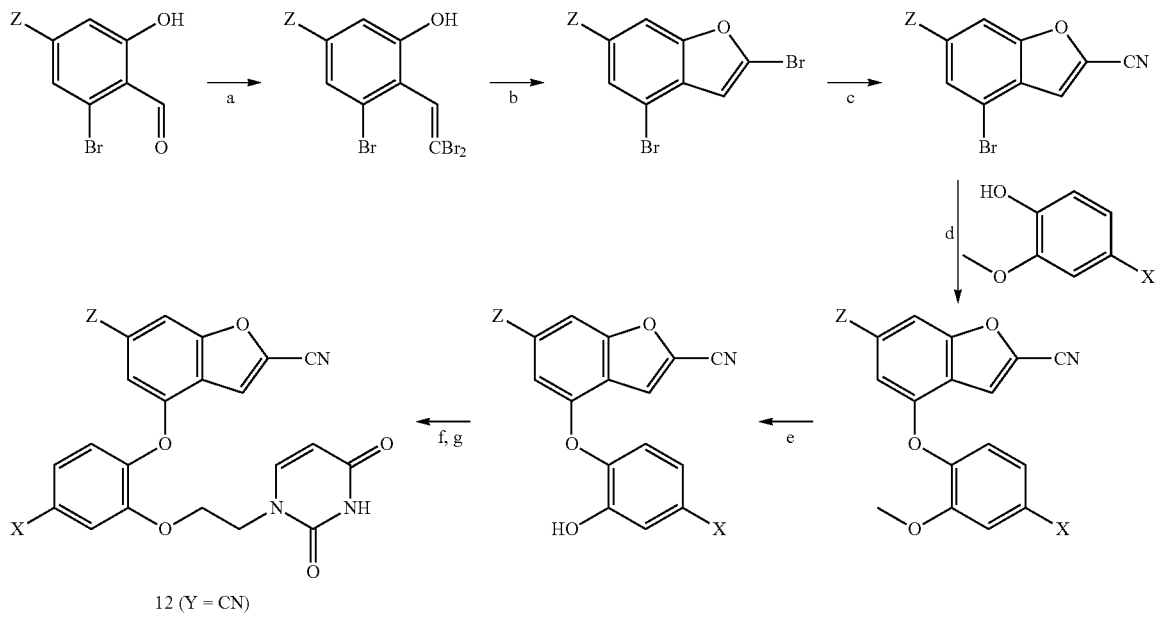

12 (Y = CN)

Reagents: (a) $PPh_3$, $CBr_4$, DCM, 0° C.→RT, 2 h; (b) CuI, $K_2CO_3$, 80° C., 4 h; (c) NaCN, DMSO, 100° C., 24 h; (d) CuI, $Cs_2CO_3$, N,N-dimethylglycine hydrochloride, dioxane, 90° C., 18 h; (e) $BBr_3$, DCM, −78° C.→0° C., 3 h; (f) 3-benzoyl, 1-bromoethyluracil, $Cs_2CO_3$ or $K_2CO_3$, DMF, 60° C., 3 h; (g) $NH_4OH$, DCM, 16 h.

For the 2-cyanobenzofurans 12 (Y=CN), the synthetic route in Scheme 3 begins with conversion of 2-hydroxybenzaldehyde derivatives to dibromovinyphenols using tetrabromomethane and triphenylphosphine (Scheme 3). A ligand-free, copper-catalyzed cross-coupling ensued to yield substituted 2-bromobenzofurans,[28] which was followed by selective displacement of the 2-bromine with sodium cyanide to yield 2-cyanobenzofurans. The rest of the sequence then proceeded as for the 2-cyanoindolizines. Access to the starting aldehydes was more involved in this case requiring a five step procedure beginning with commercially available 2-bromo-6-methoxyanilines, as detailed in the Supplementary Information.

Assay Results

As in previous studies,[6,9,14] activities against the IIIB strain of HIV-1 were measured using human MT-2 T-cells; $EC_{50}$ values are obtained as the dose required to achieve 50% protection of the infected cells by the MTT colorimetric method.[29,30] Activities against variant strains of the virus, which contain the clinically important Y181C and K103N/Y181C mutations in the RT enzyme, were also determined. $CC_{50}$ values for inhibition of MT-2 cell growth by 50% are obtained simultaneously. The antiviral and toxicity curves used triplicate samples at each concentration. The results including those for several reference NNRTIs are listed in Table 1.

The results for activity towards the wild-type virus are discussed first. The parent indole 8a turned out to be an 85-nM inhibitor, which is more potent than the drug nevirapine. Addition of a chlorine at C5 in the phenyl ring (8b) and of a 2-methyl group in the bicycle (8c) were not beneficial; however, the 2-cyano analog 8d did provide an improvement to 56 nM. Elaboration with a methyl group at the 6-position to yield 8e yielded a 10-nM NNRTI, while a chlorine at this position (8l) reduced the potency to 340 nM. Increased steric sensitivity is indicated in the pocket near Pro95 (FIG. 2) compared to the case with the cyanovinylphenyl-containing catechol diethers,[9] which would be consistent with the greater rigidity of the bicyclic alternatives. Only two of the isomeric indoles, 9a and 9b, were prepared. 9b, the isomer of 8c, was inactive, which is qualitatively consistent with the expectations from the MC/FEP results for 7l and 7m in FIG. 1. For 9a, comparison can be made with 8a; the added methyl group reduces the activity ca. 70-fold, which is consistent with the predictions for 7a and 7m in FIG. 1. In general, quantitative agreement is not expected between the MC/FEP results for relative free energies of binding and the $EC_{50}$ results from the cell-based assays. Correct qualitative guidance is all that is needed for great facilitation of lead optimization.

The first two indolizines that were synthesized were 10a and 10b. The 2-cyano analog 10b was extremely potent at 0.38 nM (380 pM) and more than 100-fold more so than the methyl analog 10a. 10b also showed no cytotoxicity ($CC_{50}$) up to the maximum tested concentration, 100 μM. This demonstrates that the design strategy of replacing the cyanovinylphenyl substituent could be very successful with proper choice of a cyano-substituted bicyclic heterocycle. A substituent in the 6-position of the indolizine was then explored with 10c-10e. The methyl and fluoro derivatives, 10c and 10d, are high picomolar inhibitors, while the Z=Cl analog 10e was again less potent at 3.7 nM. Among the remaining indolizines, the difluoro compound 10h was the most potent with an $EC_{50}$ of 0.4 nM; it also shows low cytotoxicity with a $CC_{50}$ of 50 μM. Placement of a fluorine at C4 in the phenyl ring yielded 10j, which was found to have similar potency as the 5-fluoro analog, 10f. However, there was no added benefit of having fluorines at both C4 and C5 (10k, 10l). The isomeric indolizine 11a, was also prepared. Consistent with the FEP results, it is less active than its isomer 10f, though the 6-fold difference is smaller than what might be expected from the results in FIG. 1. This may stem from the computations being for the methyl (7o, 7p) rather than cyano compounds and/or limitations with the point-charge model in the force field and its accounting of the aryl-aryl interactions with Tyr181, Tyr188, and Trp229 (FIG. 2).

The focus on the benzofurans was also for the 2-cyano substituted cases. The parent 12a emerged as an 18-nM inhibitor. Addition of the 6-methyl group to give 12b was now significantly detrimental (210 nM), while a chlorine at this position (12c) had no impact. For the fluoro analogs, 12d and 12e, addition of the 6-methyl group is again detrimental, and for the chloro compounds 12f-12g the 100-fold benefit of progressing from hydrogen to methyl to cyano at the 2-position is apparent. The isomeric benzofuran 13a was also prepared. Based on the FEP results in FIG. 1, a strong preference for the 12 series over 13 was not expected. However, the qualitative order is correct for the one case of 13a versus its isomer 12f. Overall, the FEP results were highly successful in narrowing the field of possible synthetic targets and in leading the discovery of the strikingly potent indolizines, especially 10b and 10h.

The performance of the compounds towards the mutant strains of HIV-1 is also recorded in Table 1. The variations in the results are difficult to rationalize with confidence in the absence of more experimental structural characterization of the complexes. However, the general pattern is that compounds that are more potent towards the wild type virus are also more potent towards the variants. Furthermore, the usual pattern with NNRTIs is that they are more potent towards the single Y181C variant than the double K103N/Y181C variant. Both variants are clinically important and the double mutant is viewed as being the most challenging variant. The K103N mutation is found in 57% of cases of NNRTI resistance and Y181C is found in 25% of cases.[31] Thus, it was surprising to find that the new compounds are almost uniformly more active towards the K103N/Y181C than the Y181C variant. The $EC_{50}$ values of 11 and 10 nM for 10b and 10h with the double variant are impressive and represent significant improvement over the results for 3 and 4. However, 3 and 4 perform ca. 10-fold better for the single mutant. Among the new compounds the greatest potency towards the Y181C variant is for 10d and 10i at 170 and 160 nM. It is easy to say that the present compounds are expected to lose potency towards Y181C variants owing to loss of aryl-aryl contacts indicated in FIG. 2 and in the crystal structures for the complexes of 3 and 4.[10] However, the reason for the greater loss for 10b and 10h is unclear, and the reason for the gain in activity for adding the K103N mutation is especially obscure.

Crystallography

Figure 3:
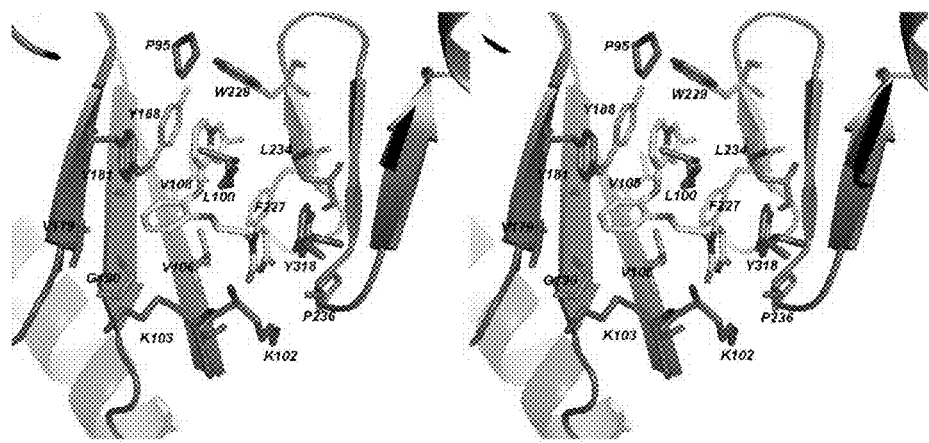
FIG. 3. Stereo view of the crystal structure for 10b complexed with HIV-RT. Numerous contacts in the binding site are apparent and consistent with those in the crystal structures for 3 and 4 and in the modeled structure in FIG. 2. The PDB code is 4MFB.

In order to begin to obtain a deeper understanding of the variations in activity for the indolizines, an X-ray crystal structure for 10b with WT HIV-1 RT was determined in the same manner as for 3 and 4.[10] The best crystals obtained using the recombinant RT52A enzyme diffracted to amplitudes extending to 2.88 Å, and phases were determined via molecular replacement using the structure for 3 as the search model (PDB code: 4H4M).[10] The overall conformation of the binding pocket is similar to the 4H4M structure in which the β6-β10-β9 sheet p66: residues 105-110, 186-191, 178-183, respectively) and YMDD loop (p66: residues 183-186) shift in order to interact with the bound inhibitor. The crystal structure for the complex with 10b is illustrated in FIG. 3; the positioning of the ligand and the contacts are predominantly as expected from FIG. 2 with the cyano group projecting into the tunnel behind Phe227. An all-atom alignment comparing the inhibitor and non-nucleoside binding pocket of the 4H4M structure and the 10b:RT complex gives an rmsd of only 0.75 Å.

Figure 4:
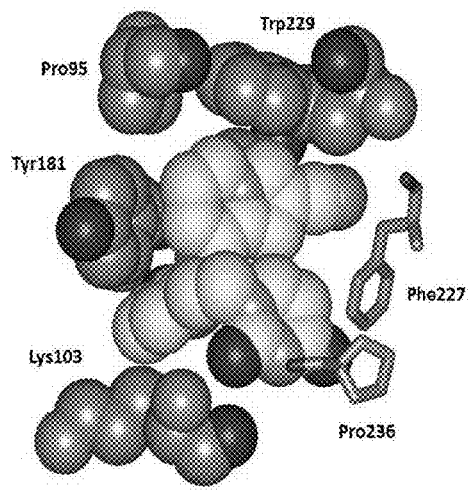
FIG. 4. A space-filling rendering made from the crystal structure of 10b bound to HV-RT. Carbon atoms of 10b are in yellow. Notable points are the hydrogen bond between a uracil oxygen atom and the backbone NH of Lys103, the aryl-aryl contacts with Tyr181 and Trp229, and the orientation of Lys103 including the contact of the $C_\beta$ atom with the inhibitor.

In the computer simulations and the crystal structure for 3 and 10b there is some variation in the conformation of the uracilylethoxy group where the dihedral angle for the connection to the central phenyl ring (C2-C1-O—C) can either be near 180° (anti as in FIG. 3) or nearer syn as in the case for 3.[10] The change is accompanied by some differences in hydrogen bonding between the uracil ring and Lys102, Lys103, and Pro236. In the present case, the C2 carbonyl oxygen of the uracil is 3.1 Å from the backbone N of Lys103, and N3 of the uracil is 3.4 Å from the backbone carbonyl oxygen of Pro236. However, the latter pair is not oriented well for hydrogen bonding, as illustrated in FIG. 4. This region is solvent exposed and significant exchange of protein-ligand, protein-water, and ligand-water hydrogen bonds is observed in the MC simulations.

There are additional points of note. The orientation of Tyr181 is the same in FIGS. 2 and 3 with the tyrosine ring and the central ring of the inhibitor perpendicular, while in the crystal structures for 3 and 4 they are parallel owing to 90° rotation of the tyrosine ring. In both cases the interaction is offset so it is not an optimal aryl-aryl interaction. However, the edge-to-face interaction between Tyr181 and the indolizine 6-membered ring of 10b does appear to be ideal and is such that a substituent could not be placed at C6 of the indolizine (Z in 10) without steric conflict with the tyrosine ring. The tight packing is apparent in FIG. 4. It seems likely that placement of a substituent at C6 would be accompanied by rotation of the tyrosine ring to the parallel geometry observed for the complexes of 3 and 4. Thus, the adverse effects of the Tyr181Cys mutation on potency for the indolizines can be attributed primarily to the loss of the aryl-aryl interaction between the bicyclic heterocycle and Tyr181.

Turning to Lys103, the orientation of its side chain is the same in the three crystal structures and from the MC modeling of the complexes. The side chain extends into the entrance channel of the NNRTI binding site with the ammonium group solvent exposed (FIGS. 3 and 4).

The shortest contact between the side chain and the inhibitors is between $C_\beta$ and C5 in the central ring at 3.8 to 4.1 Å separation. A substituent on C5 (X in 8-13) would also be in van der Waals contact with $C_\beta$ of Lys103. It is unclear based on the present structures why conversion of Lys103 to Asn is beneficial for the heterobicyclic catechol diethers and not so for the cyanovinylphenyl analogs. Crystal structures for additional complexes such as for 3 and 10b with Y181C, K103N, and K103N/Y181C HIV-RT are much desired to provide clarification.

Figure 5:
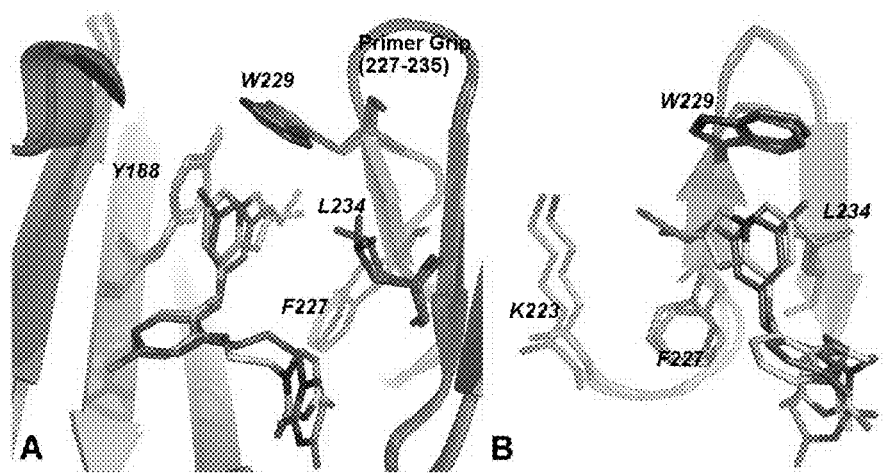
FIG. 5. Two views comparing the crystal structures for 3 and 10b. In A, the difference in conformation of the uracilylethoxy side chain is apparent, while B illustrates that the cyano group of 3 extends farther into the tunnel region and closer to Lys223.
Figure 6:
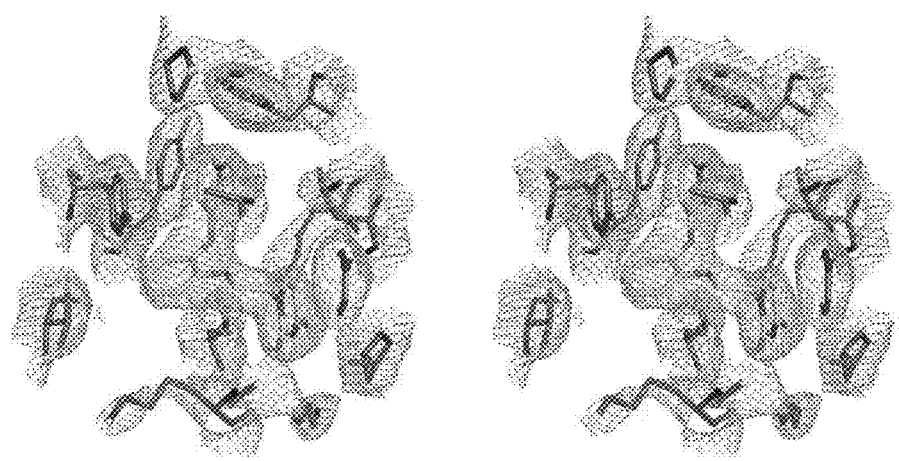
FIG. 6. Stereoview of the final $2F_o$-$F_c$ electron density (contour level of 1.0σ) showing the non-nucleoside binding pocket for the RT:10b complex, as determined in the experiment of Example 11.

A final structural point concerns the positioning of the cyano groups of the inhibitors in the tunnel. FIG. 5 provides two views comparing the crystal structures for 3 and 10b. They show that there are some differences such that the indolizine makes closer contact with Trp229 and that the cyano group of 3 extends further into the tunnel. As a result the cyano nitrogen atom of 3 is only 3.6 Å from the ammonium nitrogen of Lys223 (FIG. 5b), while the corresponding distance in the complex for 10b is 5.8 Å. In the crystal structure for 4, the side chain of Lys223 has a conformational kink that increases the separation to 6.5 Å (PDB code: 4H4O). There is water in this region that promotes the variety of possible arrangements. In any event, ion-dipole interactions with Lys223 or direct hydrogen bonding to water or Lys223 are expected to be contributing to the observed strong benefits of the cyano groups to the antiviral activity.

Solubility

Poor solubility, which has been a problem for many NNRTIs, often leads too low bioavailability, difficulties in formulation, and high dosages.[6,32,33] The issue reflects the hydrophobic nature of the NNRTI binding site. In the design of the catechol diethers, attention was paid to having both good potency and aqueous solubility. In our laboratory, solubilities are measured using a shake-flask procedure.[6,34] The compounds are dissolved in Britton-Robinson buffer and stirred in vials for 48 hours at 25° C. The pH of the buffer solutions is 6.5 as measured by a Corning General Purpose pH Combination probe (4136L21). The solution containing excess solid is filtered using a Whatman Mini-UniPrep syringeless filter device with a 0.45 μM pore size, and the supernatant is analyzed by UV-vis spectrophotometry (Agilent 8453).

As shown in Table 2, the solubilities for the drugs etravirine and rilpivirine are below 1 μg/ml, which is well outside the normal range of 4-4000 μg/ml for oral drugs.[6,33] The solubilities of the most potent indolizine analogs, 10b and 10h, are both ca. 40 μg/ml. 4, the cyanovinylphenyl analog of 10h, is 4-fold less soluble at 11 μg/ml. As also shown in Table 2, there is reasonable inverse correlation of the observed solubilities with computed octanol-water partition coefficients, which are readily obtained using ChemDraw.[38] Thus, the new compounds have solubilities somewhat less than for nevirapine, but much greater than for etravirine or rilpivirine, a favorable increase in solubility, while maintaining or increasing anti-HIV activity in many instances.

TABLE 2

Experimental Aqueous Solubility at pH 6.5 (S) and Computed ClogP

| Compd | S, μg/mL | ClogP | Compd | S, μg/mL | ClogP |
|---|---|---|---|---|---|
| 1b/4 | 10.8 | 3.09 | nevirapine | 167[a] | 2.65 |
| 1c | 510 | 3.38 | efavirenz | 68.0 | 4.67 |
| 10b | 37.9 | 2.70 | etravirine | <<1[b] | 5.22 |
| 10h | 43.8 | 3.14 | rilpavirine | 0.02,[c] | 5.75 |
| 14e | 4.3 | 3.30 | rilpivirine | 0.24[d] | 5.75 |

[a]Ref. 35.
[b]Ref. 36.
[c]Ref. 5, pH 7.
[d]Ref 37, pH 7.4.

Naphthalene Inhibitors

Potent naphthalene-containing inhibitors of HIV Reverse Transcriptase were synthesized in accordance with Scheme 4:

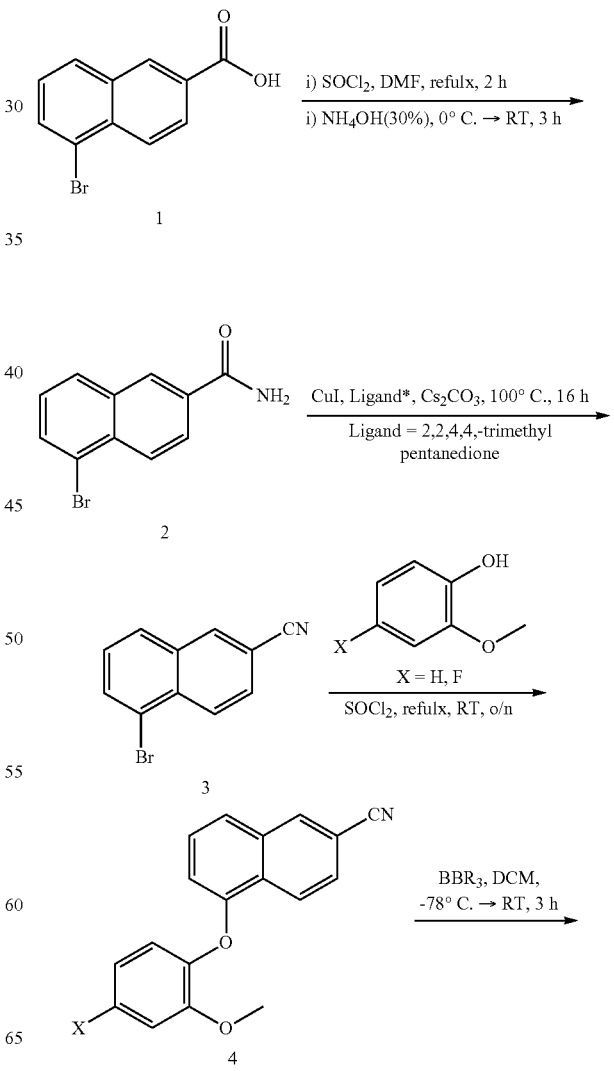

Scheme 4. Synthesis of the Naphthalene Inhibitors

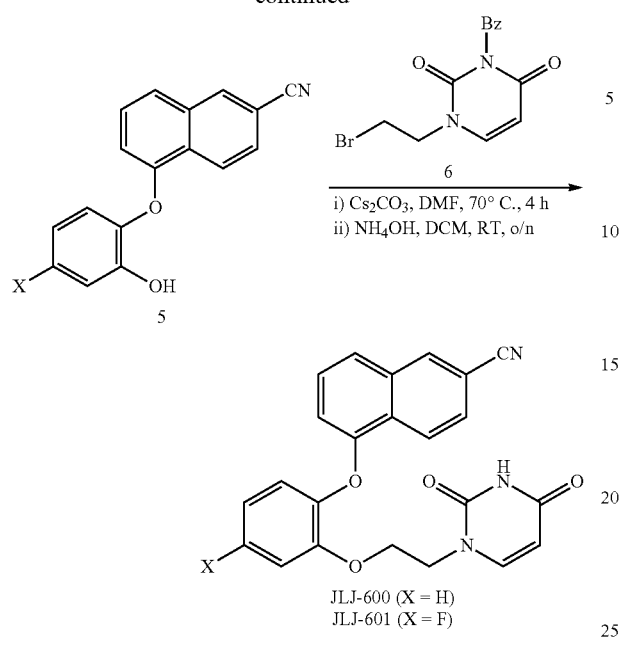

The naphthalene inhibitors having the structure 14 shown below, exhibited the HIV Reverse Transcriptase activity indicated in Table 3 and Table 4 (which shows a number of naphthalene inhibitors in comparison to other compounds according to the present invention).

TABLE 3

Inhibitory Activity ($EC_{50}$) for HIV-1 and Cytotoxicity ($CC_{50}$) in μM

14

| Compd | X | Y | Z | WT $EC_{50}{}^a$ | Y181C $EC_{50}{}^a$ | 103N181C $EC_{50}{}^a$ | $CC_{50}{}^b$ |
|---|---|---|---|---|---|---|---|
| 14e | H | CN | H | 0.00053 | 0.019 | 0.015 | >100 |
| 14i | F | CN | H | 0.00049 | 0.010 | 0.048 | >100 |
| 14k | H | CN | F | 0.0011 | 0.008 | 0.006 | >100 |
| 14l | F | CN | F | 0.0019 | 0.0056 | 0.021 | >100 |
| nevirapine | | | | 0.11 | NA | NA | >100 |
| efavirenz | | | | 0.002 | 0.010 | 0.030 | 15 |
| etravirine | | | | 0.001 | 0.008 | 0.005 | 11 |
| rilpivirine | | | | 0.00067 | 0.00065 | 0.002 | 8 |

$^a$For 50% protection in MT-2 cells; antiviral curves used triplicate samples at each concentration.
ND for not measured.
NA for $EC_{50} > CC_{50}$.
$^b$For 50% inhibition of MT-2 cell growth; toxicity curves also used triplicate samples.

Activity of Certain Preferred Compounds According to the Present Invention

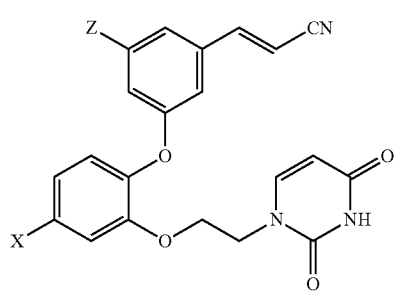

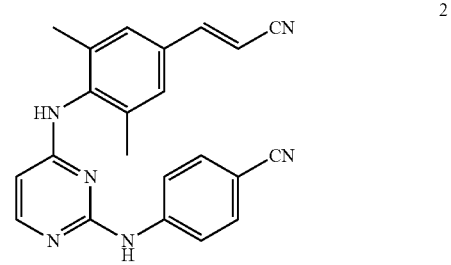

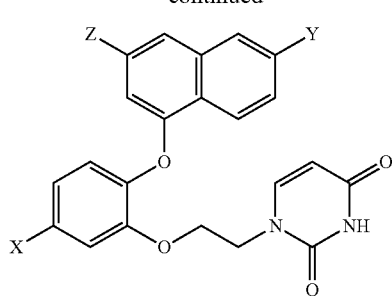

14

TABLE 4

Inhibitory Activity (EC$_{50}$) for HIV-1 and Cytotoxicity (CC$_{50}$) in μM-
Highly Active Compounds of the Present Invention

| Compd | X | Y | Z | WT EC$_{50}$[a] | Y181C EC$_{50}$[a] | K103N/ Y181C EC$_{50}$[a] | CC$_{50}$[b] |
|---|---|---|---|---|---|---|---|
| 1a/3 | Cl | — | Cl | 0.000055 | 0.049 | 0.220 | 10 |
| 1b/4 | F | — | F | 0.00032 | 0.016 | 0.085 | 45 |
| 1c-532 | H | — | Cl | 0.00031 | 0.046 | 0.024 | 18 |
| 8d | H | CN | H | 0.056 | 38 | 5.5 | 72 |
| 8e | H | CN | CH$_3$ | 0.010 | NA | 0.80 | 1.2 |
| 8f | H | CN | Cl | 0.34 | 27 | 2.7 | 81 |
| 9c | H | CN | H | 0.018 | NA | 0.42 | >100 |
| 9d | H | CN | Cl | 0.019 | 1.9 | 0.26 | >100 |
| 9e | F | CN | H | 0.040 | 3.5 | 4.0 | >100 |
| 9f | Cl | CN | H | 0.0070 | NA | NA | 7.0 |
| 10b | H | CN | H | 0.00038 | 0.31 | 0.011 | >100 |
| 10e | H | CN | F | 0.00070 | 0.17 | 0.068 | 40 |
| 10d | H | CN | Cl | 0.0037 | 0.22 | 0.022 | 39 |
| 10f | F | CN | F | 0.00040 | 0.25 | 0.010 | 50 |
| 10h | F | CN | Cl | 0.0025 | 0.16 | 0.11 | 15 |
| 14a | H | H | H | 0.060 | 5.7 | 5 | 80 |
| 14b | H | CH$_3$ | H | 0.25 | 12 | 15 | 40 |
| 14c | H | Cl | H | 0.014 | 1.0 | 0.71 | >100 |
| 14d | H | Cl | Cl | 0.038 | 0.43 | 0.52 | 45 |
| 14e | H | CN | H | 0.00053 | 0.019 | 0.015 | >100 |
| 14f | H | CN | Cl | 0.0022 | 0.013 | 0.0075 | 24 |
| 14g | F | CN | Cl | 0.0045 | 0.0053 | 0.046 | 16 |
| 14h | Cl | CN | Cl | 0.011 | 0.049 | 0.280 | 20 |
| 14i | F | CN | H | 0.00049 | 0.010 | 0.048 | >100 |
| 14j | Cl | CN | H | 0.0015 | 0.048 | 0.290 | >100 |
| 14k | H | CN | F | 0.0011 | 0.008 | 0.006 | >100 |
| 14l | F | CN | F | 0.0019 | 0.0056 | 0.021 | >100 |
| 14m | Cl | CN | F | 0.005 | 0.032 | 0.150 | 18 |
| nevirapine | | | | 0.11 | NA | NA | >100 |
| efavirenz | | | | 0.002 | 0.010 | 0.030 | 15 |
| etravirine | | | | 0.001 | 0.008 | 0.005 | 11 |
| rilpivirine | | | | 0.00067 | 0.00065 | 0.002 | 8 |

[a]For 50% protection in MT-2 cells; antiviral curves used triplicate samples at each concentration.
ND for not measured.
NA for EC$_{50}$ > CC$_{50}$.
[b]For 50% inhibition of MT-2 cell growth; toxicity curves also used triplicate samples.

CONCLUSION

Computer simulations guided the discovery of potent, novel inhibitors of HIV-1 reverse transcriptase. MC/FEP calculations were used to analyze possible replacements for a cyanovinylphenyl group that has been featured in prior NNRTIs, but that possesses reactivity concerns. The results indicated that indoles, indolizines, benzofurans and naphthalenes as represented by 8, 10, 12 and 14 are the most viable. The compounds presented in Table 4, above, represent the most active compounds in the series which have been presented.

The predictions were validated by synthesis and assaying that yielded inhibitors of the wild-type virus with EC$_{50}$ values of 10 nM or lower in all four series. The most active compounds are 10b, 10f and 14e, 14i, 14k, and 14l, which are strikingly potent with EC$_{50}$ values of 0.4-0.5 nM towards the wild-type virus and ca. 10 nM towards a difficult variant strain bearing K103N and Y181C mutations in the RT enzyme. The structural characterization was much enhanced by obtaining an X-ray crystal structure for 10b in complex with HIV-RT at 2.88-Å resolution. The structure confirmed the expected placement of the inhibitor in the binding site, the extensive aryl-aryl interactions with Tyr181, Tyr188, and Trp229, and the extension of the cyano group of 10b towards Lys223 in the tunnel region. The contact between Tyr181 and the C6-C7 region of the indolizine appears to be optimal and can explain the significant loss in activity of 10b and 10h towards the Y181C variant. However, the structural origin of the ca. 30-fold gain in activity upon addition of the K103N mutation is unclear and makes further crystallographic investigation desirable. The aqueous solubilities of 10b and 10h were also measured and, at ca. 40 μg/ml, they are in the normal range for oral drugs. In comparison to the FDA-approved drug efavirenz, 10b and 10h show improved activity towards the wild-type virus and the K103N/Y181C variant, diminished activity towards the Y181C variant, lower cytotoxicity, and similar solubility.

In comparison to etravirine and rilpivirine, the new NNRTIs show similar activity towards the wild-type virus and the K103N/Y181C variant, poorer activity towards the Y181C variant, reduced cytotoxicity, and at least 100-fold greater solubility. Overall, the valuable role that FEP calculations can play in lead optimization has been further illustrated,[7] equivalents for a cyanovinylphenyl group have been reported, and novel, potent anti-HIV agents with low cytotoxicity and good solubility have been discovered and structurally characterized.

The activity results for the naphthyl ethers are summarized in Table 4 along with corresponding data for key compounds in the 1, and 8-10 series and for four FDA-approved NNRTIs. This is the initial report for 1c and 14a-m. Among the naphthyl ethers, 14e, 14i, and 14k emerged as extremely potent NNRTIs. Before discussing the structure-activity data in more detail, it is helpful to present the crystallographic results for the complex of 14e with HIV-RT. Consistent with the crystal structures for 1a, 1b, and 5a,[5,7] key interactions for 14e include aryl-aryl contacts with Tyr181, Tyr188, and Trp229 and the naphthyl fragment, a glancing edge-to-face interaction between Tyr181 and the catechol ring, and a hydrogen bond between the C2 carbonyl group of the uracil ring and the backbone NH of Lys103. The cyano group on C6 of the naphthalene projects into the channel leading to the RT polymerase active site; computer simulations using standard methods 4,5 indicate that the cyano nitrogen is hydrogen-bonded to a water molecule.

The importance of the cyano group is apparent in the WT activities for 14a, 14b, 14c, and 14e; the unsubstituted 14a is 100-fold less active than 14e. The difference in the activities of the core structures is reflected in the data for 1c (0.32 nM), 8f (340), 9c (19), 10e (3.7), and 14f (2.2), which are identically substituted with the cyano group and a chlorine. The activity for 1c likely benefits from the added torsional degree of freedom for the cyanovinyl side chain, which allows some optimization of the interaction with Trp229. The torsion angle between the phenyl ring and vinyl group is 173° and 135° in the crystal structures for 1a and 1b,[7] while in Monte Carlo simulations for the complex of 1a and HIV-RT it ranges from 130°-180° with an average of 155°.[4] The naphthyl compound is then the next most active, followed by the indolizine.

Among the cyanonaphthalenes, 14e-14m, substitutions with fluorine or chlorine are not beneficial for WT activity except for the X=F analogue 14i, which has similar potency to 14e (0.5 nM). Additional options for substitution are limited owing to the tight packing in the binding site; aza analogues of the naphthalene group are also unlikely to be productive as there are no opportunities for hydrogen bonding with the aza nitrogens. In the indolizine series, the most potent compound is 10b, the parent cyano analogue.

Turning to the results for the viral variants, significant gains have been made with the naphthyl ethers. There are multiple compounds with $EC_{50}$ values below 20 nM for the Y181C or K103N/Y181C variants. The reason for the more than 10-fold improvements towards the Y181C variant over the results for identically substituted indolizines appears to be subtle. When the crystal structures for 10b and 14e are overlaid, there is little difference except the indolizinyl fragment is tipped up towards Trp229 more than the naphthyl group. This causes the edge of the indolizine nearest Tyr181 (C6 and C7) to be a few tenths of an Å closer to the tyrosine ring than for the left edge of the naphthalene ring system. Thus, the interaction between the indolizinyl fragment and Tyr181 may be more attractive than for naphthyl, and loss of the interactions in going to Cys181 is more damaging for indolizinyl compounds 9 than naphthyl compounds 14. Further crystallographic and computational analyses are being pursued.

The activity data for 14e, 14f, 14k, and 14l are particularly notable. 14k and 14l are more potent than efavirenz for all three viral strains, and 14k is essentially identical to etravirine in potency. The naphthyl ethers are also less cytotoxic than efavirenz, etravirine, and rilpivirine with excellent results ($CC_{50}$>100 μM) for the very potent 14e, 14i, 14k, and 14l. The $EC_{50}$ results for etravirine and rilpivirine are impressive, though they are accompanied by extremely low solubility. The solubility data are summarized in Table 2, which includes previously unpublished results for 1c and 14e. As noted before, the normal range for solubility of oral drugs is 4-4,000 μg/mL corresponding to an S of $10^{-2}$-$10^{-5}$M for a compound with a molecular weight of 400.[16,17] Though 14e barely makes it into this range, its solubility represents a ca. 40-fold improvement over etravirine and rilpivirine. The indolizines are an additional 10-fold more soluble, similar to efavirenz. For the cyanovinylphenyl series, a curious result is that while the difluoro 1b has a solubility of 11 μg/mL, duplicate measurements for the chloro analogue 1c confirmed its remarkably high solubility, 510 μg/mL. The ClogP values for the listed catechol diethers are all near 3, which is again in the normal range of 0-5 for oral drugs,[18] while etravirine and rilpivirine fall in the 5-6 region.

In summary, catechol diethers that incorporate a 6-cyano-1-naphthyl substituent have been explored as NNRTIs. Compounds 14e and 14i are very potent (0.5 nM) inhibitors of wild type HIV-1, while 14k has $EC_{50}$ values below 10 nM for all three viral strains. In comparison to heterobicyclic alternatives the naphthyl ethers show improved performance against the variant strain of the virus incorporating the Tyr181Cys mutation in HIV-RT. 14e also shows much enhanced solubility in comparison to the most recently FDA-approved NNRTIs, etravirine and rilpivirine, though its solubility is 10-fold less than for the corresponding indolizine 10b. A crystal structure for the complex of 14e with WT HIV-RT confirmed the expected binding mode. Compounds such as 14e, 14f, and 14k which feature sub-20 nM potency towards all three viral strains and very low cytotoxicity are promising for anti-viral (HIV) therapy.

The invention is illustrated further in the following non-limiting examples.

EXAMPLES

1. General Information

NMR spectra were recorded on Agilent DD2 600 (600 MHz), DD2 500 (500 MHz) and DD2 400 (400 MHz) instruments. Column chromatography was carried out using CombiFlash over redisep column cartridges employing Merck silica gel (Kieselgel 60, 63-200 μm). Pre-coated silica gel plates F-254 were used for thin-layer analytical chromatography. Mass determination were performed using electrospray ionization on water Micromass ZQ (LC-MS) and on an Agilent Technologies 6890N (GC-MS). HRMS (ESI-TOF) analyses were performed on Waters Xevo QTOF equipped with Z-spray electrospray ionization source. The purity (≥95%) of all final synthesized compounds was determined by reverse phase HPLC, using a Waters 2487 dual λ absorbance detector with a Waters 1525 binary pump and a Phenomenex Luna 5μ C18(2) 250×4.6 mm column. Samples were run at 1 mL/min using gradient mixtures of 5-100% of water with 0.1% trifluoroacetic acid (TFA) (A) and 10:1 acetonitrile:water with 0.1% TFA (B) for 22 min followed by 3 min at 100% B.

Example 1

2.1. Synthesis of Compounds 8a-c

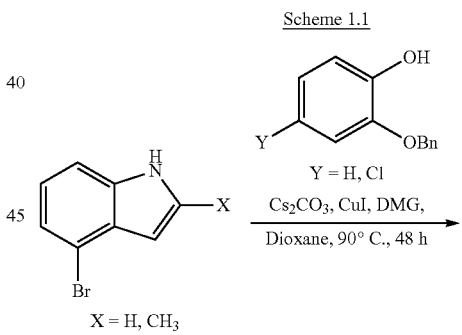

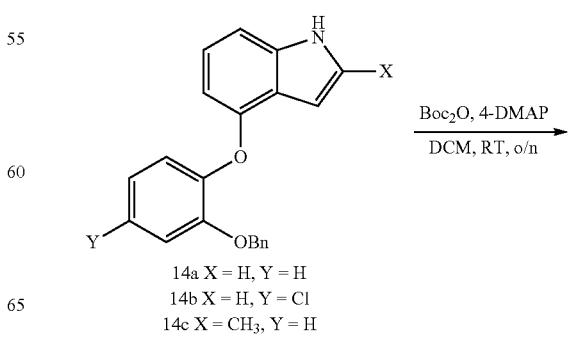

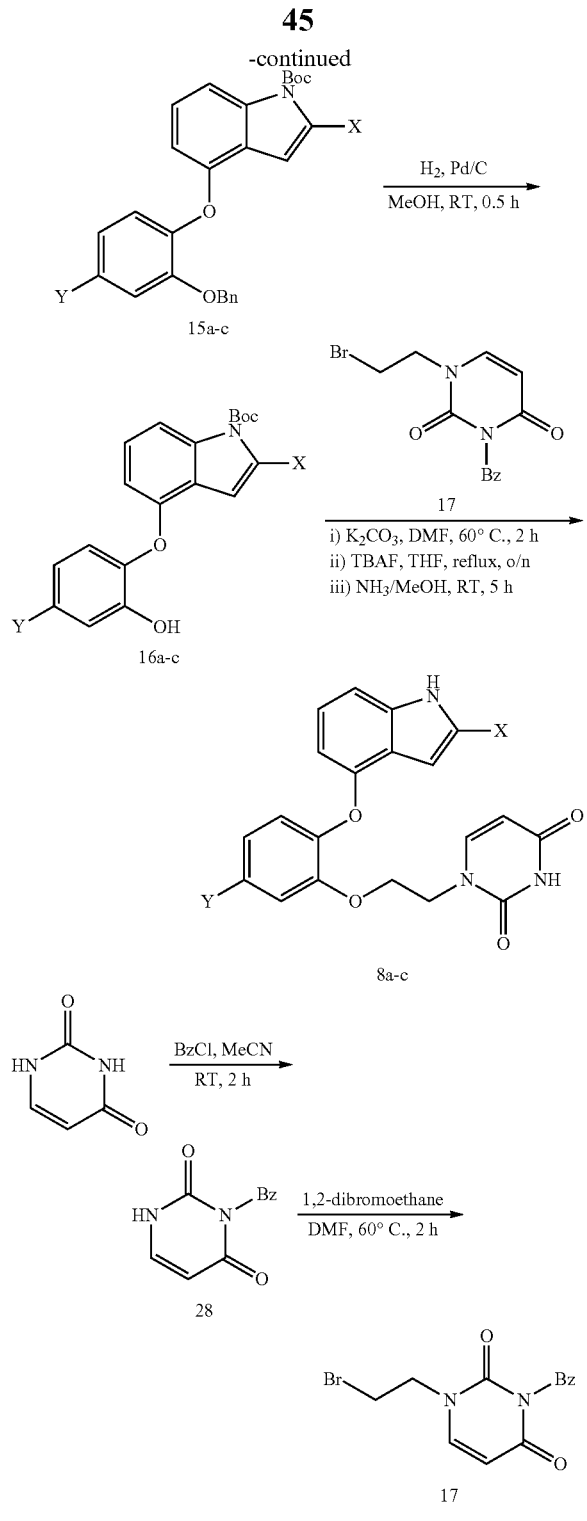

4-(2-(benzyloxy)phenoxy)-1H-indole (54a)

(42%) $^1$H NMR (500 MHz, CDCl$_3$) □ 8.19 (s, br, 1H), 7.24 (s, 4H), 7.13 (d, J=3.0 Hz, 2H), 7.08 (d, J=8.0 Hz, 1H), 7.06-7.03 (m, 4H), 6.93-6.89 (m, 1H), 6.56-6.55 (m, 2H), 5.14 (s, 2H). GC-MS (ES) for C$_{21}$H$_{17}$NO$_2$ [M]$^+$ 315.

4-(2-(benzyloxy)-4-chlorophenoxy)-1H-indole (54b)

(23%) $^1$H NMR (500 MHz, CDCl$_3$) □ 8.19 (s, br, 1H), 7.24 (s, 4H), 7.22 (d, J=2.5 Hz, 1H), 7.15-7.13 (m, 1H), 7.08 (d, J=8.0 Hz, 1H), 7.02 (d, J=2.5 Hz, 1H), 6.93 (s, 1H), 6.93 (s, 1H), 6.88 (d, J=2.5 Hz, 1H), 6.54 (d, J=8.0 Hz, 1H), 6.52 (t, J=3.0 Hz, 1H), 5.12 (s, 2H). GC-MS (ES) for C$_{21}$H$_{16}$ClNO$_2$ [M]$^+$ 349.

4-(2-(benzyloxy)phenoxy)-2-methyl-1H-indole (54c)

(23%) $^1$H NMR (400 MHz, CDCl$_3$) □ 7.89 (s, br, 1H), 7.28-7.26 (m, 4H), 7.24-7.23 (m, 2H), 7.04 (t, J=1.2 Hz, 1H), 7.03 (d, J=1.2 Hz, 1H), 7.01 (s, 1H), 6.98 (s, 1H), 6.57 (d, J=0.8 Hz, 1H), 6.54 (d, J=0.8 Hz, 1H), 6.17-6.16 (m, 1H), 5.16 (s, 2H), 2.41 (s, 3H). GC-MS (ES) for C$_2$H$_{19}$NO$_2$ [M]$^+$ 329.

Step 2[2]

To a solution of phenoxyindole (1.0 equiv) and 4-dimethylaminopyridine (1.5 equiv) in dry THF (5.0 mL per mmol phenoxyindole) at 0° C. was added a solution of Boc$_2$O (1.5 equiv) in dry THF (3.0 mL per mmol Boc$_2$O). After addition, the reaction was stirred at room temperature overnight. The reaction mixture was quenched with brine and extracted with ethyl acetate (3×10 mL). The combined organic layer was dried over anhydrous Na$_2$SO$_4$, concentrated by rotary evaporation, and purified by column chromatography to give 15a-c.

tert-butyl 4-(2-(benzyloxy)phenoxy)-1H-indole-1-carboxylate (15a)

(21%) $^1$H NMR (500 MHz, CDCl$_3$) □ 7.87 (d, J=8.0 Hz, 1H), 7.52 (d, J=3.5 Hz, 1H), 7.25-7.23 (m, 3H), 7.20-7.18 (m, 3H), 7.09-7.06 (m, 1H), 7.05-7.01 (m, 2H), 6.94-6.91 (m, 1H), 6.63 (d, J=10.5 Hz, 1H), 6.64 (s, 1H), 5.10 (s, 2H), 1.69 (s, 9H). GC-MS (ES) for C$_{26}$H$_{25}$NO$_4$ [M]$^+$ 415.

tert-butyl 4-(2-(benzyloxy)-4-chlorophenoxy)-1H-indole-1-carboxylate (15b)

(53%) $^1$H NMR (500 MHz, CDCl$_3$) □ 7.88 (d, J=8.5 Hz, 1H), 7.51 (d, J=4 Hz, 1H), 7.25-7.24 (m, 4H), 7.18-7.16 (m, 2H), 7.03 (d, J=2.5 Hz, 1H), 6.93 (d, J=9.0 Hz, 1H), 6.93 (d, J=9.0 Hz, 1H), 6.90 (d, J=2.0 Hz, 1H), 6.62-6.60 (m, 2H), 5.07 (s, 2H), 1.68 (s, 9H). GC-MS (ES) for C$_{26}$H$_{24}$ClNO$_4$ [M]$^+$ 449.

tert-butyl 4-(2-(benzyloxy)phenoxy)-2-methyl-1H-indole-1-carboxylate (15c)

(42%) $^1$H NMR (400 MHz, CDCl$_3$) □ 7.84 (d, J=8.4 Hz, 1H), 7.25-7.24 (m, 5H), 7.10 (t, J=8.0 Hz, 1H), 7.04-7.02 (m, 2H), 6.91 (s, 1H), 6.90-6.88 (m, 1H), 6.64 (d, J=8.0 Hz, 1H), 6.36 (s, 1H), 5.12 (s, 2H), 2.53 (s, 3H), 1.69 (s, 9H). GC-MS (ES) for C$_{27}$H$_{27}$NO$_4$ [M]$^+$ 429.

Step 3

To a solution of t-butyl phenoxyindole carboxylate (1.0 equiv) in dry MeOH: THF (1:1, 8.0 mL per mmol indole) was added Pd over carbon (0.15 equiv). The reaction mixture was purged with N$_2$ three times, then a H$_2$ balloon was attached, Step 1[1]

A solution of indole (1.0 equiv), phenol (1.3 equiv), Cs$_2$CO$_3$ (1.5 equiv), CuI (0.1 equiv) and N,N-dimethylglycine hydrochloride (0.3 equiv) in dry dioxane (5.0 mL per indole intermediate) was stirred at 90-100° C. under N$_2$ atmosphere in a sealed tube for 48 h. The reaction was cooled down, quenched with brine, and extracted with ethyl acetate (3×10 mL). The combined organic layer was dried over anhydrous Na$_2$SO$_4$, concentrated by rotary evaporation, and purified by column chromatography to give 54a-c.

and the reaction was stirred at room temperature until completion. The crude was filtered, concentrated by rotary evaporation, and purified by column chromatography to give 16a-c.

tert-butyl 4-(2-hydroxyphenoxy)-1H-indole-1-carboxylate (16a)

(53%) $^1$H NMR (400 MHz, CDCl$_3$) □ 7.95 (d, J=8.0 Hz, 1H), 7.55 (d, J=3.6 Hz, 1H), 7.22 (d, J=8.0 Hz, 1H), 7.09-7.03 (m, 2H), 6.83-6.77 (m, 3H), 6.55 (d, J=4.0 Hz, 1H), 5.71 (s, 1H), 1.68 (s, 9H). GC-MS (ES) for C$_{19}$H$_{19}$NO$_4$ [M]$^+$ 325.

tert-butyl 4-(4-chloro-2-hydroxyphenoxy)-1H-indole-1-carboxylate (16b)

(77%) $^1$H NMR (400 MHz, CDCl$_3$) □ 7.97 (d, J=8.0 Hz, 1H), 7.55 (d, J=3.6 Hz, 1H), 7.25 (d, J=8.0 Hz, 1H), 7.08 (d, J=2.4 Hz, 1H), 6.79-6.75 (m, 3H), 6.71 (d, J=8.8 Hz, 1H), 6.53 (d, J=3.6 Hz, 1H), 5.76 (s, 1H), 1.68 (s, 9H). GC-MS (ES) for C$_{19}$H$_{18}$ClNO$_4$ [M]$^+$ 359.

tert-butyl 4-(2-hydroxyphenoxy)-2-methyl-1H-indole-1-carboxylate (16c)

(90%) $^1$H NMR (500 MHz, CDCl$_3$) □ 7.92 (d, J=8.5 Hz, 1H), 7.29 (s, 1H), 7.15 (td, J=8.0, 1.0 Hz, 1H), 7.05 (d, J=8.0 Hz, 1H), 7.02-6.98 (m, 1H), 6.78-6.75 (m, 2H), 6.28 (s, 1H), 5.68 (s, 1H), 2.56 (s, 3H), 1.68 (s, 9H). GC-MS for C$_{20}$H$_{21}$NO$_4$ [M]$^+$ 339.

Step 4[2,3]

A solution of phenol (1.0 equiv) and K$_2$CO$_3$ (1.2 equiv) in dry DMF (4.0 mL per mmol phenol) were stirred at room temperature for 1 h. After this period, a solution of 1-(2-bromoethyl)pyrimidine-2,4(1H,3H)-dione (1.2 equiv) in dry DMF (4.0 mL per mmol phenol) was added. The reaction mixture was stirred at 60° C. for 2 h and then at room temperature overnight. The reaction was quenched with brine and extracted with ethyl acetate (3×10 mL). The combined organic layer was dried over anhydrous Na$_2$SO$_4$ and concentrated in vacuo. The crude product was dissolved in dry THF and TBAF (5.0 equiv, 1.0M solution in THF) were added and stirred at reflux under N$_2$ atmosphere overnight. The crude was cooled down, quenched with saturated NH$_4$Cl, and extracted with ethyl acetate (3×10 mL). The combined organic layer was dried over anhydrous Na$_2$SO$_4$, concentrated in vacuo and the crude was taken to the next reaction. To a solution of crude product in dry MeOH (3.0 mL) was added 3.0 mL of NH$_4$OH and the reaction was stirred at room temperature until completion. The crude reaction was concentrated by rotary evaporation and purified by column chromatography to give 8a-c. Further purification was performed by HPLC (5-100% of water with 0.1% trifluoroacetic acid (TFA) (A) and 10:1 acetonitrile:water with 0.1% TFA(B)).

1-(2-(2-((1H-indol-4-yl)oxy)phenoxy)ethyl)pyrimidine-2,4(1H,3H)-dione (8a)

(10%) $^1$H NMR (400 MHz, Acetone-d$_6$) □ 9.82 (s, br, 1H), 7.85 (d, J=8.4 Hz, 1H), 7.66 (d, J=3.6 Hz, 1H), 7.22-7.19 (m, 2H), 7.17 (t, J=8.0 Hz, 1H), 7.11 (dd, J=7.8, 1.2 Hz, 1H), 7.04-7.00 (m, 1H), 6.81 (d, J=8.0 Hz, 1H), 6.71 (d, J=3.6 Hz, 1H), 6.42 (d, J=8.0 Hz, 1H), 4.99 (dd, J=8.0, 2.4 Hz, 1H), 4.23 (t, J=4.4 Hz, 2H), 3.92 (t, J=4.4 Hz, 2H). $^{13}$C NMR (100 MHz, CDCl$_3$) □ 150.91, 150.82, 149.85, 148.98, 145.81, 125.40, 124.93, 122.56, 122.26, 114.50, 114.28, 109.79, 107.52, 105.88, 103.82, 103.58, 101.19, 66.80, 48.14. HR-MS (ES) calcd for C$_{20}$H$_{17}$N$_3$O$_4$ [M+1]$^+$ 364.1219 found 364.1255.

1-(2-(2-((1H-indol-4-yl)oxy)-5-chlorophenoxy)ethyl)pyrimidine-2,4(1H,3H)-dione (8b)

(30%) $^1$H NMR (500 MHz, CD$_3$OD) □ 7.77 (d, J=8.5 Hz, 1H), 7.55 (d, J=4.0 Hz, 1H), 7.13 (d, J=2.5 Hz, 1H), 7.07 (t, J=8.0 Hz, 1H), 7.0 (d, J=8.5 Hz, 1H), 6.96 (dd, J=8.5, 2.0 Hz, 1H), 6.73 (d, J=7.5 Hz, 1H), 6.6 (d, J=4.0 Hz, 1H), 6.31 (d, J=8.0 Hz, 1H), 4.89 (d, J=8.0 Hz, 1H), 4.14 (t, J=4.5 Hz, 2H), 3.86 (t, J=4.5 Hz, 2H). $^{13}$C NMR (125 MHz, CD$_3$OD) □ 152.53, 152.36, 150.99, 147.41, 127.54, 126.38, 125.98, 124.23, 123.09, 116.42, 111.01, 110.68, 108.41, 106.68, 104.85, 101.50, 68.16. HR-MS (ES) calcd for C$_{20}$H$_{16}$ClN$_3$O$_4$ [M+1]$^+$ 398.0829 found 398.0851.

1-(2-(2-((2-methyl-1H-indol-4-yl)oxy)phenoxy)ethyl)pyrimidine-2,4(1H,3H)-dione (8c)

(30%) $^1$H NMR (500 MHz, CD$_3$OD) □ 7.72 (d, J=8.5 Hz, 1H), 7.14-7.08 (m, 1H), 7.06 (dd, J=8.0, 1.5 Hz, 1H), 6.99-6.93 (m, 3H), 6.77 (d, J=8.0 Hz, 1H), 6.33 (s, 1H), 6.28 (d, J=8.0 Hz, 1H), 4.92 (d, J=8.0, 1H), 4.14 (t, J=4.5 Hz, 2H), 3.86 (t, J=4.5 Hz, 2H), 2.54 (d, J=1.0 Hz, 3H). $^{13}$C NMR (125 MHz, CD$_3$OD) □ 151.91, 151.71, 151.46, 147.59, 146.25, 139.70, 138.26, 126.55, 124.69, 123.31, 123.12, 116.10, 111.22, 108.75, 105.38, 101.43, 68.08, 17.28. HR-MS (ES) calcd for C$_{21}$H$_{19}$N$_3$O$_4$ [M+1]$^+$378.1454 found 378.1470.

Example 2

Synthesis of Compound 17

Step 1

Triethylamine (4.5 mmol) and benzoyl chloride (4.5 mmol) were added to a solution of uracil (3.0 mmol) in acetonitrile (15 mL) and the mixture was stirred for 2 h. The reaction mixture was poured into brine (20 mL) and extracted with ethyl acetate (2×30 mL). The organic layer was sequentially washed with brine, dried over anhydrous Na$_2$SO$_4$, and concentration by rotary evaporation. After completion, the reaction mixture was concentrated by rotary evaporation and purified by column chromatography to give 28.

3-benzoylpyrimidine-2,4(1H,3H)-dione (28)

(43%) $^1$H NMR (500 MHz, DMSO-d$_6$) u 11.61 (s, 1H), 7.96 (dd, J=8.3, 1.1 Hz, 2H), 7.79 (t, J=7.4 Hz, 1H), 7.68 (d, J=7.7 Hz, 1H), 7.62 (t, J=7.9 Hz, 2H), 5.75 (d, J=7.7 Hz, 1H). LC-MS (ES) for C$_{11}$H$_9$N$_2$O$_3$ [M+1]$^+$ 316.98.

Step 2

1,2-dibromoethane (3.3 mmol), and K$_2$CO$_3$ (2.0 mmol) were added to a solution of 28 (1.3 mmol) in dry DMF (10 mL) and the mixture was stirred for 3 h at 60° C. to complete the reaction. The reaction mixture was poured into brine (20 mL) and extracted with ethyl acetate (2×25 mL). The organic layer was sequentially washed with brine, dried over anhydrous Na$_2$SO$_4$, concentrated by rotary evaporation, and purified by column chromatography to give 17.

3-benzoyl-1-(2-bromoethyl)pyrimidine-2,4(1H,3H)-dione (17)

(37%) $^1$H NMR (400 MHz, CDCl$_3$) □ 8.00-7.93 (m, 2H), 7.73-7.66 (m, 1H), 7.57-7.50 (m, 2H), 7.36 (d, J=8.0 Hz, 1H), 5.86 (d, J=8.0 Hz, 1H), 4.19 (t, J=5.7 Hz, 2H), 3.72 (t, J=5.7 Hz, 2H). LC-MS (ES) for $C_{13}H_{11}BrN_2O_3$ [M+1]$^+$ 323.90.

Example 3

2.2. Representative synthesis of Compounds 8 d-f

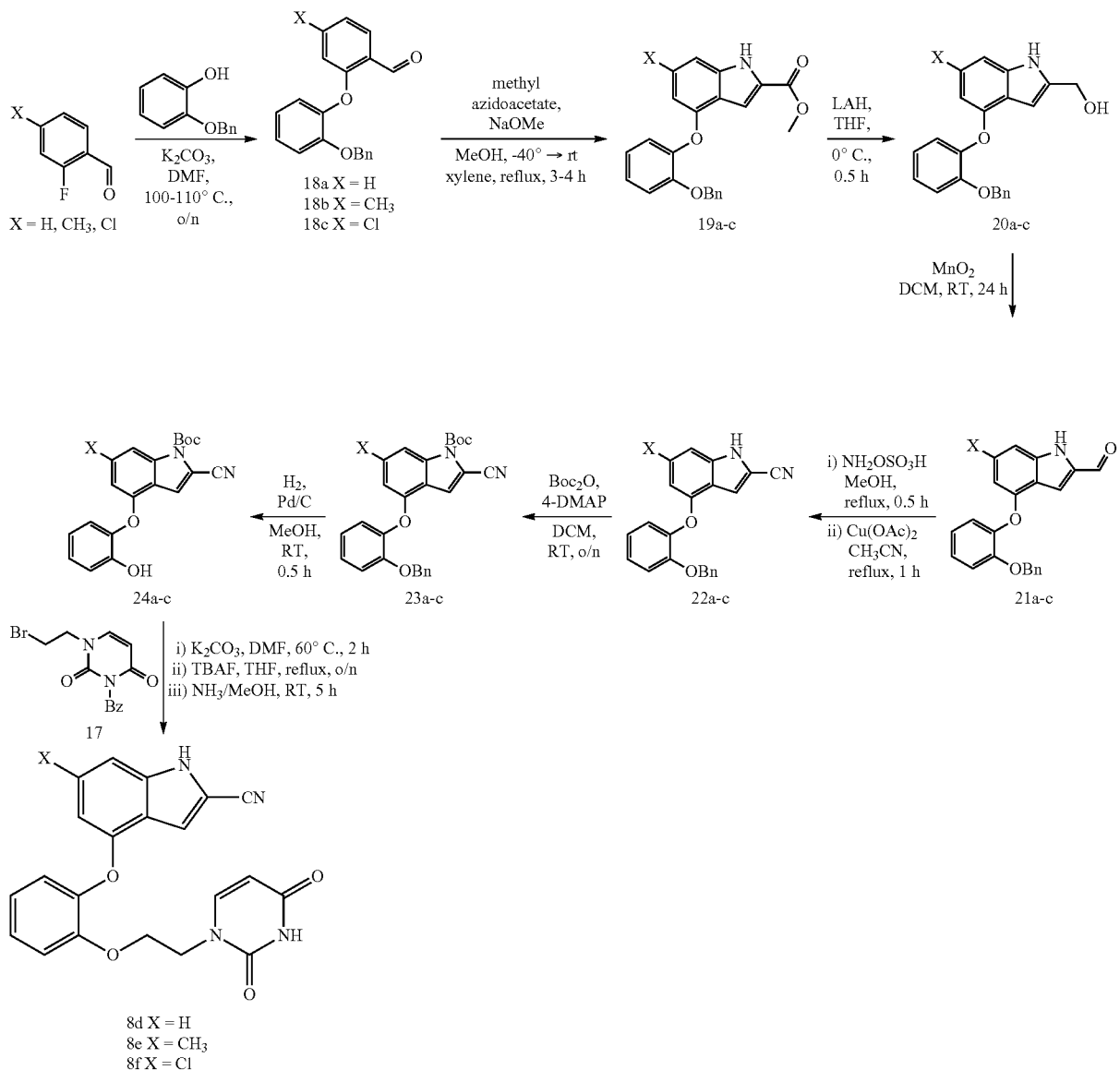

Scheme 1.2

Step 1

A solution of benzylaldehyde (1.0 equiv), 2-benzyloxyphenol (1.0 equiv), and $K_2CO_3$ (1.5 equiv) in dry DMF (3.0 mL per mmol benzylaldehyde) were stirred at 100-110° C. under $N_2$ atmosphere overnight. The reaction was cooled down, quenched with 1N HCl, and extracted with ethyl acetate (3×15 mL). The combined organic layer was dried over anhydrous $Na_2SO_4$, concentrated by rotary evaporation and purified by column chromatography to give 18a-c.

2-(2-(benzyloxy)phenoxy)benzaldehyde (18a)

(69%) $^1$H NMR (400 MHz, CDCl$_3$) δ 10.65 (s, 1H), 7.91 (dd, J=7.8, 2.0 Hz, 1H), 7.46-7.42 (m, 1H), 7.25 (d, J=2.4 Hz, 2H), 7.19-7.15 (m, 2H), 7.14-7.10 (m, 4H), 7.08 (dd, J=8.2, 1.6 Hz, 1H), 7.01 (td, J=7.8, 1.2 Hz, 1H), 6.75 (d, J=8.4 Hz, 1H), 5.06 (s, 2H). GC-MS (ES) for $C_{20}H_{16}O_3$ [M]$^+$ 304.

2-(2-(benzyloxy)phenoxy)-4-methylbenzaldehyde (18b)

(46%) $^1$H NMR (500 MHz, CDCl$_3$) δ 10.58 (s, 1H), 7.81 (d, J=8.0 Hz, 1H), 7.27-7.26 (m, 3H), 7.18-7.13 (m, 4H), 7.07 (dd, J=8.5, 1.0 Hz, 1H), 7.01 (td, J=7.5, 1.5 Hz, 1H), 6.93 (d, J=7.0 Hz, 1H), 6.53 (s, 1H), 5.06 (s, 2H), 2.28 (s, 3H). GC-MS (ES) for $C_{21}H_{18}O_3$ [M]$^+$ 318.

2-(2-(benzyloxy)phenoxy)-4-chlorobenzaldehyde (18c)

(60%) $^1$H NMR (400 MHz, CDCl$_3$) δ 10.56 (s, 1H), 7.81 (d, J=8.4 Hz, 1H), 7.27-7.26 (m, 4H), 7.21 (dd, J=7.2, 1.6 Hz, 1H), 7.17 (dd, J=8.0, 1.6 Hz, 1H), 7.11 (d, J=1.6 Hz, 1H), 7.09-7.07 (m, 1H), 7.05 (t, J=0.8 Hz, 1H), 7.03 (s, 1H), 6.69 (d, J=1.2 Hz, 1H), 5.05 (s, 2H). GC-MS (ES) for C$_{20}$H$_{15}$ClO$_3$ [M]$^+$ 338.

Step 2[4]

To a stirred solution of (benzyloxy)phenoxybenzaldehyde (1.0 equiv) and methyl 2-azidoacetate (4.0 equiv) in dry MeOH (4.0 mL per mmol benzaldehyde) under N$_2$ atmosphere at −40° C., was added a solution of 25% sodium methoxide (4.0 equiv) dropwise. The reaction was stirred at −40° C. for 2 h, and then to 0° C. for 2 h. After this time, the reaction mixture was allowed to warm to room temperature and stirred overnight. The crude reaction was concentrated in vacuo, quenched with water, and extracted with dry xylenes (3×20 mL). The combined organic layer was dried over anhydrous Na$_2$SO$_4$. The above solution was added dropwise to a stirring solution of dry xylene and stirred at reflux for 4 h under N$_2$ atmosphere. The crude reaction was cooled down, quenched with water, and extracted with ethyl acetate (3×15 mL). The combined organic layer was dried over anhydrous Na$_2$SO$_4$, concentrated by rotary evaporation, and purified by column chromatography to give 19a-c.

methyl 4-(2-(benzyloxy)phenoxy)-1H-indole-2-carboxylate (19a)

(62%) $^1$H NMR (400 MHz, CDCl$_3$) δ 8.84 (s, br, 1H), 7.31-7.30 (m, 1H), 7.22-7.21 (m, 4H), 7.17-7.16 (m, 2H), 7.11 (d, J=8.0 Hz, 2H), 7.09-7.07 (m, 1H), 7.05 (dd, J=6.4, 1.2 Hz, 1H), 6.97-6.93 (m, 1H), 6.47 (d, J=6.8 Hz, 1H), 5.10 (s, 2H), 3.92 (s, 3H). GC-MS (ES) for C$_{23}$H$_{19}$NO$_4$ [M]$^+$ 373.

methyl 4-(2-(benzyloxy)phenoxy)-6-methyl-1H-indole-2-carboxylate (19b)

(46%) $^1$H NMR (500 MHz, CDCl$_3$) δ 9.06 (s, br, 1H), 7.44-7.42 (m, 2H), 7.31-7.24 (m, 4H), 7.18-7.16 (m, 1H), 7.14-7.12 (m, 1H), 7.10 (s, 1H), 7.00-6.98 (m, 1H), 6.92 (d, J=1.5 Hz, 1H), 6.36 (s, 1H), 5.12 (s, 2H), 3.91 (s, 3H), 2.30 (s, 3H). GC-MS (ES) for C$_{24}$H$_{21}$NO$_4$ [M]$^+$ 387.

methyl 4-(2-(benzyloxy)phenoxy)-6-chloro-1H-indole-2-carboxylate (19c)

(47%) $^1$H NMR (500 MHz, CDCl$_3$) δ 8.84 (s, br, 1H), 7.30 (d, J=1.5 Hz, 1H), 7.23-7.22 (m, 4H), 7.15-7.14 (m, 5H), 7.09 (s, 1H), 6.99 (td, J=7.5, 1.5 Hz, 1H), 6.37 (s, 1H), 5.07 (s, 2H), 3.93 (s, 3H). GC-MS (ES) for C$_{23}$H$_{18}$ClNO$_4$ [M]$^+$ 407.

Step 3[5]

A solution of the methyl 4-(2-(benzyloxy)phenoxy)-1H-indole-2-carboxylate (1.0 equiv) in dry THF was added to a solution of LAH (3.0 equiv) in dry THF at 0° C. and stirred for 30 min at 0° C. The reaction was quenched by adding water (3.0 mL) dropwise (very slowly), then aq. 20% NaOH (3.0 mL), and water (5.0 mL) dropwise. Afterwards, a solution of DCM:MeOH (8:1, 25 mL) was added and the slurry was stirred at room temperature for 1 h. The crude reaction was filtered and the organic layer was dried over anhydrous Na$_2$SO$_4$, concentrated by rotary evaporation, and purified by column chromatography to give 20a-c.

(4-(2-(benzyloxy)phenoxy)-1H-indol-2-yl)methanol (20a)

(51%) $^1$H NMR (400 MHz, CDCl$_3$) δ 8.36 (s, br, 1H), 7.23 (d, J=1.2 Hz, 4H), 7.08 (d, J=4.4 Hz, 1H), 7.06 (s, 1H), 7.05-7.03 (m, 2H), 7.02-7.00 (m, 1H), 6.92-6.88 (m, 2H), 6.56 (dd, J=6.8, 1.2 Hz, 1H), 6.38 (d, J=1.6 Hz, 1H), 5.13 (s, 2H), 4.78 (s, 2H). GC-MS (ES) for C$_{22}$H$_{19}$NO$_3$ [M]$^+$ 345.

(4-(2-(benzyloxy)phenoxy)-6-methyl-1H-indol-2-yl)methanol (20b)

(37%) $^1$H NMR (500 MHz, CDCl$_3$) δ 8.22 (s, br, 1H), 7.42 (s, 1H), 7.25 (s, 3H), 7.14-7.12 (m, 1H), 7.03 (td, J=8.0, 1.5 Hz, 2H), 6.94 (td, J=8.0, 1.5 Hz, 1H), 6.91-6.89 (m, 1H), 6.39 (s, 1H), 5.14 (s, 2H), 4.75 (s, 2H), 2.37 (s, 3H). GC-MS (ES) for C$_{23}$H$_{21}$NO$_3$ [M]$^+$ 359.

(4-(2-(benzyloxy)phenoxy)-6-chloro-1H-indol-2-yl)methanol (20c)

(43%) $^1$H NMR (400 MHz, CDCl$_3$) δ 8.40 (s, br, 1H), 7.42 (s, 1H), 7.25-7.22 (m, 4H), 7.19-7.18 (m, 2H), 7.11-7.07 (m, 2H), 7.06 (s, 1H), 7.03 (dd, J=8.8, 1.6 Hz, 1H), 6.97-6.93 (m, 1H), 6.39-6.38 (m, 1H), 5.09 (s, 2H), 4.76 (s, 2H). GC-MS (ES) for C$_{22}$H$_{18}$ClNO$_3$ [M]$^+$ 379.

Step 4[5]

To a solution of (4-(2-(benzyloxy)phenoxy)-1H-indol-2-yl)methanol (1.0 equiv) in dry DCM (5.0 mL per mmol indole) was added MnO$_2$ (5.0 equiv) and the reaction was stirred at room temperature for 24 h under N$_2$ atmosphere. The crude was filtered through celite and the organic layer was concentrated in vacuo to yield 21a-c.

4-(2-(benzyloxy)phenoxy)-1H-indole-2-carbaldehyde (21a)

(82%) $^1$H NMR (500 MHz, CDCl$_3$) δ 9.77 (s, 1H), 8.92 (s, br, 1H), 7.34 (d, J=2.5 Hz, 1H), 7.23 (d, J=8.0 Hz, 1H), 7.20-7.19 (m, 3H), 7.16-7.13 (m, 2H), 7.12-7.09 (m, 3H), 7.07 (dd, J=8.5, 1.0 Hz, 1H), 6.99 (td, J=7.5, 1.5 Hz, 1H), 6.44 (d, J=8.0 Hz, 1H), 5.07 (s, 2H). GC-MS (ES) for C$_{22}$H$_{17}$NO$_3$ [M]$^+$ 343.

4-(2-(benzyloxy)phenoxy)-6-methyl-1H-indole-2-carbaldehyde (21b)

(86%) $^1$H NMR (500 MHz, CDCl$_3$) δ 9.71 (s, 1H), 8.79 (s, br, 1H), 7.26-7.25 (m, 2H), 7.15-7.13 (M, 4H), 7.06 (d, J=8.0 Hz, 1H), 6.99 (d, J=7.0 Hz, 1H), 6.89 (s, 1H), 6.27 (s, 1H), 5.09 (s, 2H), 2.36 (s, 3H). GC-MS (ES) for C$_{23}$H$_{19}$NO$_3$ [M]$^+$ 357.

4-(2-(benzyloxy)phenoxy)-6-chloro-1H-indole-2-carbaldehyde (21c)

(66%) $^1$H NMR (500 MHz, CDCl$_3$) δ 9.76 (s, 1H), 8.91 (s, br, 1H), 7.33 (dd, J=2.0, 0.5 Hz, 1H), 7.22-7.20 (m, 3H), 7.19 (s, 1H), 7.18 (s, 1H), 7.12-7.10 (m, 2H), 7.09 (t, J=1.5 Hz, 1H), 7.07 (dd, J=8.5, 1.0 Hz, 1H), 7.02 (td, J=7.8, 1.5 Hz, 1H), 6.36 (d, J=1.5 Hz, 1H), 5.06 (s, 2H). GC-MS (ES) for C$_{22}$H$_{16}$ClNO$_3$ [M]$^+$ 377.

Step 5[6]

A solution of 4-(2-(benzyloxy)phenoxy)-1H-indole-2-carbaldehyde (1.0 equiv) in dry MeOH (7.5 mL per mmol indole) and hydroxylamine-O-sulfonic acid (2.0 equiv) was stirred at room temperature for 15 min and then heated at reflux for 30 min. The reaction mixture was cooled down and concentrated in vacuo. The residue was triturated with water, filtered, and the slurry was dissolved in ethyl acetate. The organic layer was dried over anhydrous $Na_2SO_4$ and concentrated in vacuo. Afterwards, the crude product was diluted in dry $CH_3CN$ (10 mL per mmol indole) and anhydrous $Cu(OAc)_2$ (0.1 equiv) was added to the above solution and stirred at reflux for 1 h. The crude reaction was then cooled down and concentrated in vacuo. After that, the crude product was extracted with ether (3×15 mL) and the organic layer was washed with aq. 5% $H_2SO_4$ (3×10 mL), washed with water, dried over anhydrous $Na_2SO_4$, concentrated by rotary evaporation, and purified by column chromatography to give 22a-c.

4-(2-(benzyloxy)phenoxy)-1H-indole-2-carbonitrile (22a)

(38%) $^1$H NMR (500 MHz, CDCl$_3$) δ 8.50 (s, br, 1H), 7.24-7.20 (m, 5H), 7.14-7.11 (m, 4H), 7.07 (t, J=9.0 Hz, 2H), 6.97 (t, J=7.5 Hz, 1H), 6.48 (d, J=7.5 Hz, 1H), 5.06 (s, 2H). GC-MS (ES) for $C_{22}H_{16}N_2O_2$ [M]$^+$ 340.

4-(2-(benzyloxy)phenoxy)-6-methyl-1H-indole-2-carbonitrile (22b)

(19%) $^1$H NMR (500 MHz, CDCl$_3$) δ 8.34 (s, br, 1H), 7.23-7.22 (m, 3H), 7.14-7.11 (m, 4H), 7.10 (dd, J=8.0, 1.5 Hz, 1H), 7.05 (dd, J=8.0, 1.0 Hz, 1H), 6.97 (td, J=7.5, 1.0 Hz, 1H), 6.87 (s, 1H), 6.32 (s, 1H), 5.07 (s, 2H), 2.35 (s, 3H). GC-MS (ES) for $C_{23}H_{18}N_2O_2$ [M]$^+$ 354.

4-(2-(benzyloxy)phenoxy)-6-chloro-1H-indole-2-carbonitrile (22c)

(40%) $^1$H NMR (400 MHz, CDCl$_3$) δ 8.51 (s, br, 1H), 7.24-7.22 (m, 5H), 7.13-7.10 (m, 2H), 7.07-7.06 (m, 2H), 7.04 (dd, J=10.0, 1.6 Hz, 1H), 7.01-6.99 (m, 1H), 6.40 (d, J=1.6 Hz, 1H), 5.05 (s, 2H). GC-MS (ES) for $C_{22}H_{15}ClN_2O_2$ [M]$^+$ 374.

Step 6

To a solution of 4-(2-(benzyloxy)phenoxy)-1H-indole-2-carbonitrile (1.0 equiv) and 4-Dimethylamino pyridine (1.5 equiv) in dry THF (20 mL per mmol indole) at 0° C. was added a solution of Boc$_2$O (1.5 equiv) in dry THF (10 mL per mmol indole). After addition, the crude reaction was stirred at room temperature overnight. The reaction was quenched with brine and extracted with ethyl acetate (3×10 mL). The combined organic layer was dried over anhydrous $Na_2SO_4$, concentrated by rotary evaporation, and purified by column chromatography to give 23a-c.

tert-butyl 4-(2-(benzyloxy)phenoxy)-2-cyano-1H-indole-1-carboxylate (23a)

(80%) $^1$H NMR (500 MHz, CDCl$_3$) δ 7.88 (d, J=8.5 Hz, 1H), 7.42 (s, 1H), 7.32 (t, J=8.0 Hz, 1H), 7.23-7.22 (m, 3H), 7.15 (td, J=7.5, 1.5 Hz, 1H), 7.11 (dd, J=7.8, 1.5 Hz, 1H), 7.09-7.07 (m, 2H), 7.05 (dd, J=7.5, 1.0 Hz, 1H), 6.98 (td, J=8.0, 1.0 Hz, 1H), 6.58 (d, J=8.0 Hz, 1H), 5.02 (s, 2H), 1.74 (s, 9H). GC-MS (ES) for $C_{27}H_{24}N_2O_4$ [M]$^+$ 440.

tert-butyl 4-(2-(benzyloxy)phenoxy)-2-cyano-6-methyl-1H-indole-1-carboxylate (23b)

(74%) $^1$H NMR (500 MHz, CDCl$_3$) δ 7.74 (s, 1H), 7.34 (s, 1H), 7.24-7.23 (m, 4H), 7.15 (t, J=8.0 Hz, 1H), 7.12-7.09 (m, 2H), 7.05 (d, J=8.0 Hz, 1H), 6.98 (t, J=7.5 Hz, 1H), 6.41 (s, 1H), 5.04 (s, 2H), 2.38 (s, 3H), 1.73 (s, 9H). GC-MS (ES) for $C_{28}H_{26}N_2O_4$ [M]$^+$ 454.

tert-butyl 4-(2-(benzyloxy)phenoxy)-6-chloro-2-cyano-1H-indole-1-carboxylate (23c)

(80%) $^1$H NMR (500 MHz, CDCl$_3$) δ 7.93 (s, 1H), 7.40 (s, 1H), 7.24-7.23 (m, 3H), 7.19 (dd, J=8.0, 1.5 Hz, 1H), 7.16 (dd, J=8.0, 1.5 Hz, 1H), 7.10-7.08 (m, 2H), 7.06 (dd, J=8.0, 1.5 Hz, 1H), 7.01 (dd, J=8.0, 1.5 Hz, 1H), 6.51 (d, J=1.5 Hz, 1H), 5.01 (s, 2H), 1.73 (s, 9H). GC-MS (ES) for $C_{27}H_{23}ClN_2O_4$ [M]$^+$ 474.

Step 7

To a solution of t-butyl phenoxyindole carboxylate (1.0 equiv) in dry MeOH: THF (1:1, 25 mL per mmol indole) was added Pd over carbon (0.2 equiv). The reaction mixture was purged with $N_2$ three times, then a $H_2$ balloon was attached, and the reaction was stirred at room temperature until completion. The crude was filtered, concentrated by rotary evaporation, and purified by column chromatography to give 24a-c.

tert-butyl 2-cyano-4-(2-hydroxyphenoxy)-1H-indole-1-carboxylate (24a)

(71%) $^1$H NMR (500 MHz, CDCl$_3$) δ 7.99 (d, J=8.5 Hz, 1H), 7.40 (t, J=8.0 Hz, 2H), 7.11-7.08 (m, 2H), 6.88-6.85 (m, 2H), 6.76 (d, J=8.0 Hz, 1H), 5.47 (s, br, 1H), 1.73 (s, 9H). GC-MS (ES) for $C_{20}H_{18}N_2O_4$ [M]$^+$ 350.

tert-butyl 2-cyano-4-(2-hydroxyphenoxy)-6-methyl-1H-indole-1-carboxylate (24b)

(60%) $^1$H NMR (500 MHz, CDCl$_3$) δ 7.84 (s, 1H), 7.32 (s, 1H), 7.11-7.08 (m, 2H), 6.87-6.86 (m, 2H), 6.59 (s, 1H), 5.47 (s, br, 1H), 2.42 (s, 3H), 1.73 (s, 9H). GC-MS (ES) for $C_{21}H_{20}N_2O_4$ [M]$^+$ 364.

tert-butyl 6-chloro-2-cyano-4-(2-hydroxyphenoxy)-1H-indole-1-carboxylate (24c)

(74%) $^1$H NMR (500 MHz, CDCl$_3$) δ 8.06 (s, 1H), 7.39 (t, J=1.0 Hz, 1H), 7.18-7.15 (m, 1H), 7.11 (d, J=8.0, 1.5 Hz, 1H), 6.96-6.92 (m, 2H), 6.71 (d, J=1.5 Hz, 1H), 5.35 (s, 1H), 1.74 (s, 9H). GC-MS (ES) for $C_{20}H_{17}ClN_2O_4$ [M]$^+$ 384.

Step 8

A solution of phenol (1.0 equiv) and $K_2CO_3$ (1.2 equiv) in dry DMF (4.0 mL per mmol phenol) were stirred at rt for 1 hr. Then, a solution of 1-(2-bromoethyl)pyrimidine-2,4(1H,3H)-dione (1.2 equiv) in dry DMF (4.0 mL per mmol phenol) was added and the reaction mixture was stirred at 60° C. for 2 h and then at room temperature. After overnight, the crude reaction was quenched with brine and extracted with ethyl acetate (3×10 mL). The combined organic layer was dried over anhydrous $Na_2SO_4$ and concentrated in vacuo. The crude product was dissolved in dry THF and TBAF (5.0 equiv, 1.0M solution in THF) was added and stirred at reflux under $N_2$ atmosphere overnight. The crude was cooled down, quenched with saturated $NH_4Cl$, and extracted with ethyl acetate (3×10 mL). The combined organic layer was dried over anhydrous $Na_2SO_4$ and concentrated in vacuo. The crude was taken to next reaction. To a solution of crude product in dry MeOH (3.0 mL) was added 3.0 mL of a $NH_4OH$ and the crude reaction was stirred at room temperature until reaction completion. The crude reaction was by rotary evaporation and purified column chromatography to give 8d-f. Further purification was performed by HPLC (5-100% of water with 0.1% trifluoroacetic acid (TFA) (A) and 10:1 acetonitrile:water with 0.1% TFA(B)) to afford final product.

4-(2-(2-(2,4-dioxo-3,4-dihydropyrimidin-1(2H)-yl)ethoxy)phenoxy)-1H-indole-2-carbonitrile (8d)

(10%) $^1$H NMR (500 MHz, DMSO-$d_6$) δ 12.50 (s, 1H), 11.12 (s, 1H), 7.32 (s, 1H), 7.22-7.20 (m, 2H), 7.19 (s, 1H), 7.14-7.11 (m, 1H), 7.10 (d, J=4.0 Hz, 2H), 6.84 (d, J=7.5 Hz, 1H), 6.13 (d, J=9.0 Hz, 1H), 4.79 (dd, J=8.0, 2.0 Hz, 1H), 4.14 (t, J=6.0 Hz, 2H), 3.83 (t, J=5.0 Hz, 2H). $^{13}$C NMR (200 MHz, DMSO-$d_6$) δ 163.36, 157.74, 157.59, 150.71, 150.12, 145.55, 143.03, 138.85, 129.38, 126.42, 126.13, 122.53, 121.84, 117.26, 114.59, 114.53, 110.27, 106.41, 105.16, 103.74, 99.83, 66.12, 46.99. HR-MS (ES) calcd for $C_{21}H_{16}N_4O_4$ [M+1]$^+$ 389.1250 found 389.1247.

4-(2-(2-(2,4-dioxo-3,4-dihydropyrimidin-1(2H)-yl)ethoxy)phenoxy)-6-methyl-1H-indole-2-carbonitrile (8e)

(10%) $^1$H NMR (500 MHz, DMSO-$d_6$) δ 12.34 (s, 1H), 11.15 (s, 1H), 7.25 (s, 1H), 7.23-7.21 (m, 2H), 7.12 (d, J=8.0 Hz, 1H), 7.02 (td, J=5.0, 1.0 Hz, 1H), 6.89 (s, 1H), 6.85 (d, J=8.0 Hz, 1H), 5.97 (s, 1H), 4.78 (dd, J=8.0, 2.0 Hz, 1H), 4.15 (t, J=5.0 Hz, 2H), 3.84 (t, J=5.0 Hz, 2H), 2.24 (s, 3H). $^{13}$C NMR (200 MHz, DMSO-$d_6$) δ 163.39, 157.81, 157.67, 151.34, 150.74, 150.19, 145.55, 139.17, 136.51, 126.13, 122.53, 121.89, 115.37, 114.73, 144.66, 110.31, 106.06, 104.42, 99.81, 66.16, 47.13, 21.69. HR-MS (ES) calcd for $C_{22}H_{18}N_4O_4$ [M+1]$^+$ 403.1407 found 403.1395.

6-chloro-4-(2-(2-(2,4-dioxo-3,4-dihydropyrimidin-1(2H)-yl)ethoxy)phenoxy)-1H-indole-2-carbonitrile (8f)

(8%) $^1$H NMR (400 MHz, DMSO-$d_6$) δ 12.70 (s, 1H), 11.12 (s, 1H), 7.39 (d, J=1.2 Hz, 1H), 7.25 (d, J=1.6 Hz, 1H), 7.22 (dd, J=7.5, 1.2 Hz, 1H), 7.15 (s, 1H), 7.13 (s, 1H), 7.09-7.05 (m, 1H), 6.88 (d, J=8.0 Hz, 1H), 5.99 (d, J=1.2 Hz, 1H), 4.76 (dd, J=7.8, 2.4 Hz, 1H), 4.17 (t, J=4.8 Hz, 2H), 3.85 (t, J=4.8 Hz, 2H). $^{13}$C NMR (200 MHz, DMSO-$d_6$) δ 163.27, 157.85, 157.70, 152.28, 150.67, 150.07, 145.38, 142.04, 138.48, 130.64, 126.93, 122.85, 121.99, 115.93, 114.67, 110.54, 106.10, 99.73, 66.07, 47.05. HR-MS (ES) calcd for $C_{21}H_{15}ClN_4O_4$ [M+1]$^+$ 423.0861 found 423.0847.

Example 4

3. Synthesis of Compounds 9a-b

Scheme 1.3

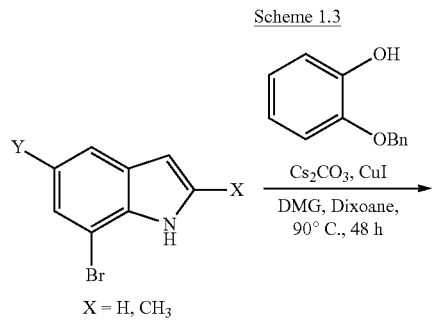

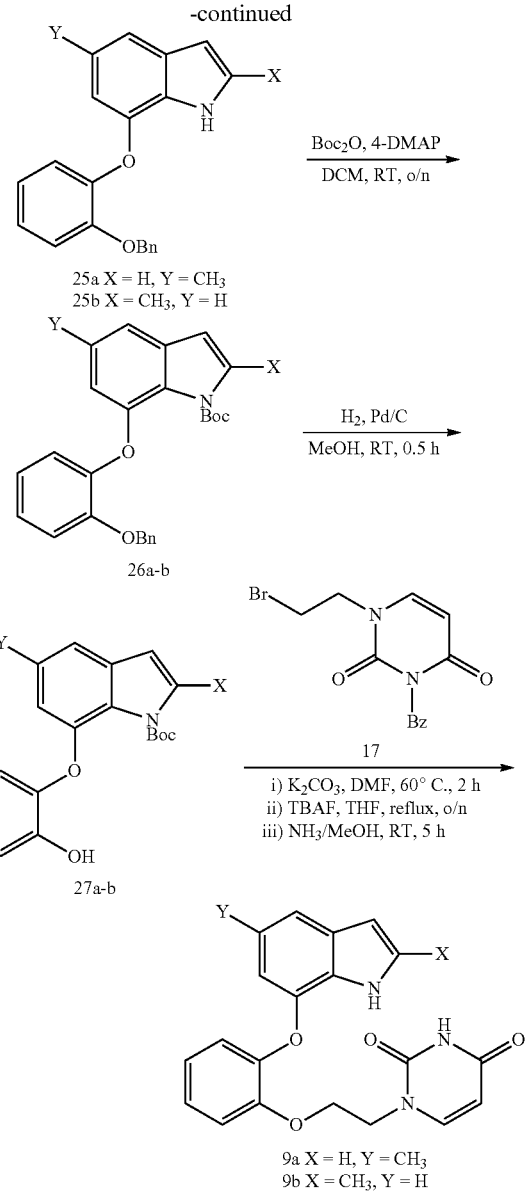

Step 1

7-(2-(benzyloxy)phenoxy)-5-methyl-1H-indole (25a)

Following step 1 in the synthetic scheme 1.1, 25a, from 7-bromo-5-methyl-1H-indole, was obtained after column chromatography. (47%) $^1$H NMR (500 MHz, CDCl$_3$) δ 8.27 (s, br, 1H), 7.42-7.42 (m, 4H), 7.27-7.26 (m, 2H), 7.09-7.07 (m, 4H), 6.94 (d, J=1.0 Hz, 1H), 6.50 (s, 1H), 6.47 (t, J=2.5 Hz, 1H), 5.12 (s, 2H), 2.37 (s, 3H). GC-MS (ES) for $C_{22}H_{19}NO_2$ [M]$^+$ 329.

7-(2-(benzyloxy)phenoxy)-2-methyl-1H-indole (25b)

Following step 1 in the synthetic scheme 1.1, 25b, from 7-bromo-2-methyl-1H-indole, was obtained after column chromatography. (84%) $^1$H NMR (500 MHz, CDCl$_3$) δ 8.14 (s, br, 1H), 7.28-7.27 (m, 4H), 7.23 (d, J=7.0 Hz, 1H), 7.08-

7.07 (m, 2H), 6.94 (s, 1H), 6.93-6.92 (m, 1H), 6.89 (td, J=8.0, 1.5 Hz, 1H), 6.84 (dd, J=7.5, 1.5 Hz, 1H), 6.60 (d, J=7.5 Hz, 1H), 6.23 (d, J=2.0 Hz, 1H), 5.12 (s, 2H), 2.37 (s, 3H). GC-MS (ES) for $C_{21}H_{19}NO_2$ [M]$^+$ 329.

Step 2 tert-butyl 7-(2-(benzyloxy)phenoxy)-5-methyl-1H-indole-1-carboxylate (26a)

Following step 2 in the synthetic scheme 1.1 26a, from 25a, was obtained after column chromatography. (53%) $^1$H NMR (400 MHz, CDCl$_3$) δ 7.53 (d, J=2.8 Hz, 1H), 7.26-7.22 (m, 5H), 7.08 (s, 1H), 6.98-6.96 (m, 2H), 6.87 (t, J=2.8 Hz, 2H), 6.60 (s, 1H), 6.48 (d, J=3.6 Hz, 1H), 5.13 (s, 2H), 2.31 (s, 3H), 1.46 (s, 9H). GC-MS (ES) for $C_{27}H_{27}NO_4$ [M]$^+$ 429.

tert-butyl 7-(2-(benzyloxy)phenoxy)-2-methyl-1H-indole-1-carboxylate (26b)

Following step 2 in the synthetic scheme 1.1 26b, from 25b, was obtained after column chromatography. (61%) $^1$H NMR (500 MHz, CDCl$_3$) δ 7.43 (d, J=7.0 Hz, 1H), 7.24-7.23 (m, 2H), 7.18-7.13 (m, 4H), 7.04-7.03 (m, 1H), 7.01 (s, 1H), 6.99 (s, 1H), 6.96-6.95 (m, 1H), 6.59 (d, J=8.0 Hz, 1H), 6.29 (d, J=1.0 Hz, 1H), 5.10 (s, 2H), 2.50 (s, 3H), 1.48 (s, 9H). GC-MS (ES) for $C_{27}H_{27}NO_4$ [M]$^+$ 429.

Step 3 tert-butyl 7-(2-hydroxyphenoxy)-5-methyl-1H-indole-1-carboxylate (27a)

Following step 3 in the synthetic scheme 1.1 27a, from 26a, was obtained after column chromatography. (21%) $^1$H NMR (500 MHz, CDCl$_3$) δ 9.18 (s, 1H), 7.25 (s, 1H), 7.14 (d, J=8.0 Hz, 1H), 7.11 (dd, J=9.2, 2.0 Hz, 1H), 7.07 (dd, J=7.3, 1.5 Hz, 1H), 6.87 (td, =8.3, 1.5 Hz, 1H), 6.71 (s, 1H), 6.42 (s, 1H), 2.19 (s, 3H), 1.53 (s, 9H). GC-MS (ES) for $C_{20}H_{21}NO_4$ [M]$^+$ 339.

tert-butyl 7-(2-hydroxyphenoxy)-2-methyl-1H-indole-1-carboxylate (27b)

Following step 3 in the synthetic scheme 1.1 27b, from 26b, was obtained, after column chromatography. (63%) $^1$H NMR (500 MHz, CDCl$_3$) δ 7.72 (s, 1H), 7.15 (dd, J=7.75, 1.0 Hz, 1H), 7.07-7.06 (m, 1H), 7.05 (t, J=2.0 Hz, 1H), 6.91 (td, J=7.8, 2.0 Hz, 1H), 6.87 (td, J=7.5, 1.5 Hz, 1H), 6.68 (dd, J=8.0, 0.5 Hz, 1H), 6.31 (d, J=1.0 Hz, 1H), 5.46 (s, 1H), 2.52 (s, 3H), 1.60 (s, 9H). GC-MS (ES) for $C_{20}H_{21}NO_4$ [M]$^+$ 339.

Step 4

1-(2-(2-((5-methyl-1H-indol-7-yl)oxy)phenoxy)ethyl)pyrimidine-2,4(1H,3H)-dione (9a)

Following step 4 in the synthetic scheme 1.1 9a, from 27a, was obtained after column chromatography. Further purification was performed by HPLC (5-100% of water with 0.1% trifluoroacetic acid (TFA) (A) and 10:1 acetonitrile:water with 0.1% TFA (B)) to afford final product. (8%) $^1$H NMR (500 MHz, DMSO-d$_6$) δ 11.20 (s, br, 1H), 7.28 (d, J=7.5 Hz, 1H), 7.11 (td, J=8.0, 1.5 Hz, 2H), 7.06 (dd, J=8.0, 1.5 Hz, 1H), 6.93 (td, J=8.0, 1.5 Hz, 1H), 6.88 (dd, J=8.0, 1.5 Hz, 1H), 6.75 (s, 1H), 6.52 (s, br, 1H), 6.25 (s, 1H), 5.26 (dd, J=7.5, 2.0 Hz, 1H), 4.16 (t, J=5.0 Hz, 2H), 3.92 (t, J=5.0 Hz, 2H), 2.13 (s, 3H). $^{13}$C NMR (125 MHz, DMSO-d$_6$) δ 152.73, 150.83, 149.26, 145.84, 145.62, 144.37, 136.61, 134.35, 129.40, 124.34, 121.73, 120.08, 119.73, 116.16, 114.88, 100.33, 66.38, 20.53. HR-MS (ES) calcd for $C_{21}H_{19}N_3O_4$ [M+1]$^+$ 378.1454 found 378.1470.

1-(2-(2-((2-methyl-1H-indol-7-yl)oxy)phenoxy)ethyl)pyrimidine-2,4(1H,3H)-dione (9b)

Following step 4 in the synthetic scheme 1.1 9b, from 27b, was obtained after column chromatography. Further purification was performed by HPLC (5-100% of water with 0.1% trifluoroacetic acid (TFA) (A) and 10:1 acetonitrile:water with 0.1% TFA (B)) to afford final product. (20%). $^1$H NMR (500 MHz, Acetone-d$_6$) δ 10.23 (s, br, 1H), 9.84 (s, br, 1H), 7.15-7.14 (m, 3H), 7.05 (dd, J=8.0, 1.5 Hz, 1H), 7.00-6.96 (m, 1H), 6.80 (t, J=8.0 Hz, 1H), 6.55 (d, J=8.0 Hz, 1H), 6.27 (dd, J=7.5, 0.5 Hz, 1H), 6.23-6.22 (m, 1H), 4.91 (d, J=7.5 Hz, 1H), 4.20 (t, J=5.0 Hz, 2H), 3.83 (t, J=5.0 Hz, 2H), 2.47 (d, J=0.5 Hz, 3H).$^{13}$C NMR (125 MHz, Acetone-d$_6$) δ163.80, 151.15, 146.33, 145.67, 144.35, 125.84, 122.63, 122.22, 119.98, 115.46, 114.64, 114.61, 106.45, 101.17, 67.59, 48.52, 13.44. HR-MS (ES) calcd for $C_{21}H_{19}N_3O_4$ [M+1]$^+$ 378.1454 found 378.1456.

Example 5

4.1. Synthesis of Compounds 10a-n

Scheme 2.1

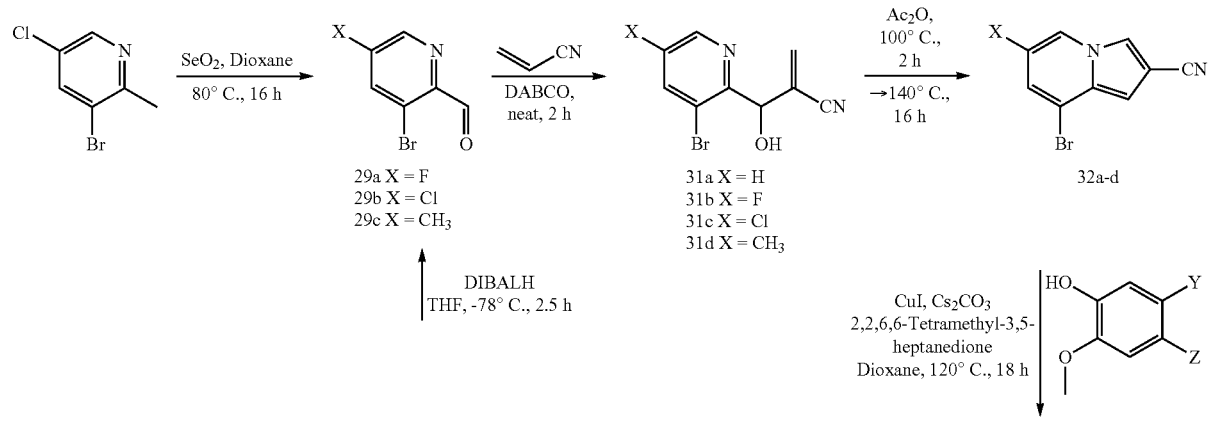

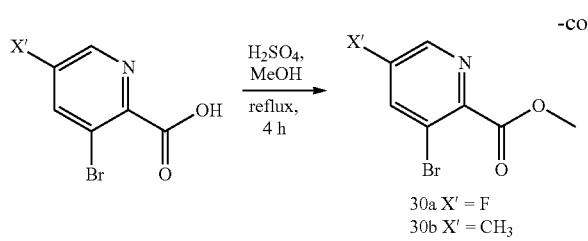
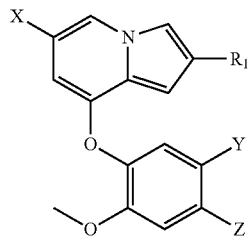

30a X' = F
30b X' = CH₃

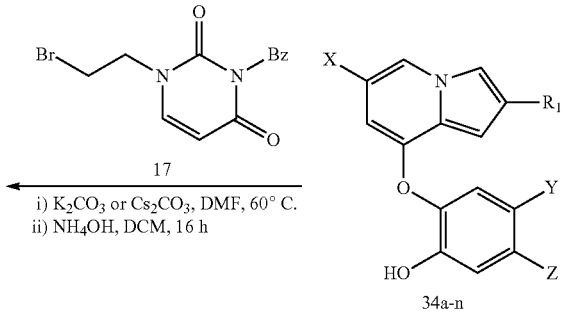

33a R₁ = CH₃, X = H, Y = H, Z = H    33b R₁ = CN, X = H, Y = H, Z = H
33c R₁ = CN, X = CH₃, Y = H, Z = H   33d R₁ = CN, X = F, Y = H, Z = H
33e R₁ = CN, X = Cl, Y = H, Z = H    33f R₁ = CN, X = H, Y = H, Z = F
33g R₁ = CN, X = CH₃, Y = H, Z = F   33h R₁ = CN, X = F, Y = H, Z = F
33i R₁ = CN, X = Cl, Y = H, Z = F    33j R₁ = CN, X = H, Y = F, Z = H
33k R₁ = CN, X = H, Y = F, Z = F     33l R₁ = CN, X = F, Y = F, Z = F
33m R₁ = CN, X = H, Y = H, Z = Cl    33n R₁ = CN, X = Cl, Y = H, Z = Cl

BBr₃, DCM
−78° C. → 0° C., 3 h

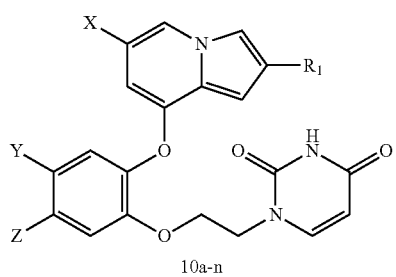

10a-n i) K₂CO₃ or Cs₂CO₃, DMF, 60° C.
ii) NH₄OH, DCM, 16 h

17

34a-n

Step A1

A mixture of SeO₂ (16 mmol) in dioxane (20 mL) was pre-heated over 80° C., then a solution of 3-bromo-5-chloro-2-methylpyridine (4.0 mmol) in dioxane (5.0 mL) was added. After stirring at 80° C. for 16 h, the reaction mixture was cooled and filtered. The filtrate was concentrated by rotary evaporation, and purified by column chromatography to give 29b.

3-bromo-5-chloropicolinaldehyde (29b)

(76%) $^1$H NMR (400 MHz, CDCl₃) δ 10.20 (s, 1H), 8.81 (s, 1H), 7.69 (s, 1H). LC-MS (ES) for C₆H₃BrClNO [M+1]⁺ 220.99.

Step B1

A mixture of the corresponding 3-bromopicolinic acid (1.0 equiv) and sulfonic acid (10 equiv) in MeOH (2.0 mL per mmol pyridine) was heated at reflux for 4 h. The reaction mixture was cooled in ice bath and neutralized with 2N aq. Na₂CO₃ solution. The aqueous layer was extracted with ethyl acetate, and the combined organic solution was dried over anhydrous Na₂SO₄, concentrated by rotary evaporation, and purified by column chromatography to give 30a-b.

methyl 3-bromo-5-fluoropicolinate (30a)

(76%) $^1$H NMR (400 MHz, CDCl₃) δ 8.43 (d, J=4 Hz, 1H), 7.72 (dd, J=4.0, 8.0 Hz, 1H), 3.94 (s, 3H). LC-MS (ES) for C₇H₅BrFNO₂ [M+1]⁺ 235.06.

methyl 3-bromo-5-methylpicolinate (30b)

(92%) $^1$H NMR (400 MHz, CDCl₃) δ 8.40-8.33 (m, 1H), 7.77 (dd, J=1.8, 0.8 Hz, 1H), 3.93 (s, 3H), 2.33 (s, 3H). LC-MS (ES) for C₈H₈BrNO₂ [M+1]⁺ 230.98.

Step B2

A solution of the corresponding methyl picolinate (1.0 equiv) in THF (1.0 mL per mmol picolinate) was cooled to −78° C. After 10 min, diisobutylaluminum hydride (1.5 equiv, 1.0 M in THF) was added dropwise over 40 min and stirred for an additional 2.5 h at −78° C. After which it was quenched by MeOH and diluted with 1N aq. NaHCO₃ solution. The aqueous solution was extracted with ethyl acetate, and the combined organic solution was dried over anhydrous Na₂SO₄, concentrated by rotary evaporation, and purified by column chromatography to give 29a and 29c.

3-bromo-5-fluoropicolinaldehyde (29a)

(86%) $^1$H NMR (400 MHz, CDCl₃) δ 10.12 (s, 1H), 8.57 (d, J=2.4 Hz, 1H), 7.78-7.70 (m, 1H). LC-MS (ES) for C₆H₃BrFNO₂ [M+1]⁺ 220.33.

3-bromo-5-methylpicolinaldehyde (29c)

(89%) $^1$H NMR (400 MHz, CDCl₃) δ 10.15 (s, 1H), 8.51 (s, 1H), 7.79 (s, 1H), 2.37 (s, 3H). LC-MS (ES) for C₇H₆BrNO [M+1]⁺ 201.01.

Step 2

A mixture of the corresponding pyridine-2-carbaldehydes (1.0 equiv), acrylonitrile (10 equiv) and 1,4-diazabicyclo[2.2.2]octane (DABCO) (1.1 equiv) was stirred for 1.5 h at room temperature, diluted with ethyl acetate, and washed with water. The organic layer was dried over anhydrous Na₂SO₄, concentrated by rotary evaporation, and purified by column chromatography to give 31a-d.

2-((3-bromopyridin-2-yl)(hydroxy)methyl)acrylonitrile (31a)

(82%) $^1$H NMR (400 MHz, CDCl$_3$) δ 8.61 (dd, J=4.7, 1.2 Hz, 1H), 7.95 (dd, J=8.1, 1.4 Hz, 1H), 7.27 (dd, J=8.0, 4.7 Hz, 1H), 6.14 (dd, J=22.0, 0.6 Hz, 2H), 5.55 (d, J=8.0 Hz, 1H), 5.23 (d, J=8.0 Hz, 1H). LC-MS (ES) for C$_9$H$_6$BrClN$_2$O [M+1]$^+$ 238.98.

2-((3-bromo-5-fluoropyridin-2-yl)(hydroxy)methyl) acrylonitrile (31b)

(86%) $^1$H NMR (400 MHz, CDCl$_3$) δ 8.44 (d, J=2.0 Hz, 1H), 7.69 (dd, J=4.0, 8.0 Hz, 1H), 6.05 (s, 2H), 5.48 (d, J=8.0 Hz, 1H), 4.78 (d, J=8.0 Hz, 1H). LC-MS (ES) for C$_9$H$_6$BrFN$_2$O [M+1]$^+$ 258.97.

2-((3-bromo-5-chloropyridin-2-yl)(hydroxy)methyl) acrylonitrile (31c)

(64%) $^1$H NMR (400 MHz, CDCl$_3$) δ 8.51 (d, J=2.0 Hz, 1H), 7.91 (d, J=2.0 Hz, 1H), 6.10 (d, J=0.9 Hz, 2H), 5.47 (d, J=8.0 Hz, 1H), 4.77 (d, J=8.0 Hz, 1H). LC-MS (ES) for C$_9$H$_6$BrClN$_2$O [M+1]$^+$ 274.94.

2-((3-bromo-5-methylpyridin-2-yl)(hydroxy)methyl) acrylonitrile (31d)

(86%) $^1$H NMR (400 MHz, CDCl$_3$) δ 8.35 (s, 1H), 7.70 (d, J=1.8 Hz, 1H), 6.05 (d, J=0.6 Hz, 2H), 5.42 (d, J=7.9 Hz, 1H), 5.13 (d, J=8.0 Hz, 1H), 2.31 (S, 3H). LC-MS (ES) for C$_{10}$H$_9$BrN$_2$O [M+1]$^+$ 253.00.

Step 3[7]

A solution of the corresponding pyridine intermediate (1.0 equiv) in acetic anhydride (1.0 mL per mmol of pyridine intermediate) was heated at 100° C. for 2 h. After this time, the reaction mixture was heated at 140° C. for 7 h or overnight. The solution was cooled to room temperature, then a solution of sodium bicarbonate was added at 0° C., and stirred for 30 min. Ethyl acetate was added and the organic layer was extracted and washed with brine, dried over anhydrous Na$_2$SO$_4$, concentrated by rotary evaporation, and purified column by chromatography to give 32a-d.

8-bromoindolizine-2-carbonitrile (32a)

(86%) $^1$H NMR (400 MHz, CDCl$_3$) δ 7.51 (d, J=7.9 Hz, 1H), 7.08-6.98 (m, 1H), 6.61-6.30 (m, 1H). LC-MS (ES) for C$_9$H$_5$BrN$_2$ [M+1]$^+$ 220.12.

8-bromo-6-fluoroindolizine-2-carbonitrile (32b)

(48%) $^1$H NMR (400 MHz, CDCl$_3$) 7.78 (s, 1H), 7.66 (s, 1H), 7.02 (s, 1H), 6.85 (s, 1H). LC-MS (ES) for C$_9$H$_4$BrFN$_2$ [M+1]$^+$240.07.

8-bromo-6-chloroindolizine-2-carbonitrile (32c)

(48%) $^1$H NMR (400 MHz, Acetone-d$_6$) δ 8.61-8.58 (m, 1H), 8.27 (d, J=1.7 Hz, 1H), 7.30 (d, J=1.5 Hz, 1H), 7.00 (s, 1H). LC-MS (ES) for C$_9$H$_4$BrClN$_2$ [M+1]$^+$ 256.22.

8-bromo-6-methylindolizine-2-carbonitrile (32d)

(65%) $^1$H NMR (400 MHz, CDCl$_3$) 7.60-7.57 (m, 2H), 6.87 (d, J=0.9 Hz, 1H), 6.73 (s, 1H), 2.17 (s, 3H). LC-MS (ES) for C$_{10}$H$_7$BrN$_2$ [M+1]$^+$ 236.04.

Step 4

A mixture of the corresponding indolizine intermediate (1.0 equiv), the corresponding catechol (2.5 equiv), Cs$_2$CO$_3$ (2.2 equiv), CuI (0.2 equiv) and 2,2,6,6-tetramethyl-3,5-heptanedione (0.4 equiv) in dioxane (1.0 mL per mmol indolizine) in a sealed tube was heated at 120° C. under nitrogen atmosphere for 18 h. The cooled mixture was partitioned between ethyl acetate and water. The organic layer was separated, and the aqueous layer was extracted with ethyl acetate. The combined organic layers were washed with brine, dried over anhydrous Na$_2$SO$_4$, concentrated by rotary evaporation, and purified by column chromatography to give 33a-n.

8-(2-methoxyphenoxy)-2-methylindolizine (33a)

(87%) $^1$H NMR (400 MHz, CDCl$_3$) δ 7.40 (d, J=8.4 Hz, 1H), 7.23-7.12 (m, 2H), 7.09-6.99 (m, 1H), 6.93-6.88 (m, 1H), 6.63 (dd, J=8.1, 1.2 Hz, 1H), 6.17-6.10 (m, 2H), 3.78 (s, 3H), 2.10 (s, 3H). LC-MS (ES) for C$_{16}$H$_{15}$NO$_2$ [M+1]$^+$ 254.12.

8-(2-methoxyphenoxy)indolizine-2-carbonitrile (33b)

(40%) $^1$H NMR (400 MHz, CDCl$_3$) δ 7.61 (d, J=6.9 Hz, 1H), 7.09-7.01 (m, 2H), 6.47 (t, J=7.2 Hz, 1H), 3.69 (3H, s). LC-MS (ES) for C$_{16}$H$_{12}$N$_2$O$_2$ [M+1]$^+$ 265.24

8-(2-methoxyphenoxy)-6-methylindolizine-2-carbonitrile (33c)

(84%) $^1$H NMR (400 MHz, CDCl$_3$) δ 7.56 (d, J=2.0 Hz, 1H), 7.34 (s, 1H), 7.19-7.13 (m, 1H), 7.03 (dd, J=7.9, 1.6 Hz, 1H), 6.98 (d, J=8.0 Hz, 1H), 6.93 (td, J=8.0, 1.6 Hz, 1H), 6.80 (s, 1H), 5.65 (s 1H), 3.75 (s, 3H), 2.05 (s, 3H). LC-MS (ES) for C$_{17}$H$_{14}$N$_2$O$_2$ [M+1]$^+$ 279.11.

6-fluoro-8-(2-methoxyphenoxy)indolizine-2-carbonitrile (33d)

(51%) $^1$H NMR (400 MHz, CDCl$_3$) δ 7.56 (d, J=2.0 Hz, 1H), 7.49 (ddd, J=4.0, 1.7, 0.9 Hz, 1H), 7.09 (dd, J=7.9, 1.6 Hz, 1H), 7.08-7.03 (m, 1H), 7.00-6.91 (m, 3H), 5.71 (dd, J=10.0, 1.7 Hz, 1H), 3.74 (s, 3H). LC-MS (ES) for C$_{16}$H$_{11}$FN$_2$O$_2$ [M+1]$^+$ 283.10.

6-chloro-8-(2-methoxyphenoxy)indolizine-2-carbonitrile (33e)

(57%) $^1$H NMR (400 MHz, Acetone-d$_6$) δ 7.61-7.59 (m, 1H), 7.53 (d, J=1.6 Hz, 1H), 7.02-6.91 (m, 4H), 6.79 (d, J=1.5 Hz, 1H), 5.52 (s, 1H), 3.74 (s, 3H). LC-MS (ES) for C$_{16}$H$_{11}$ClN$_2$O$_2$ [M+1]$^+$ 299.06.

8-(4-fluoro-2-methoxyphenoxy)indolizine-2-carbonitrile (33f)

(76%) $^1$H NMR (400 MHz, CDCl$_3$) δ 7.60 (d, J=1.6 Hz, 1H), 7.57 (d, J=6.9 Hz, 1H), 6.90 (dd, J=8.9, 5.2 Hz, 1H), 6.85-6.79 (m, 2H), 6.69 (dd, J=8.8, 5.2 Hz, 1H), 6.18 (t, J=7.2 Hz, 1H), 5.93 (d, J=7.2 Hz, 1H), 3.88 (s, 3H). LC-MS (ES) for C$_{16}$H$_{11}$FN$_2$O$_2$ [M+1]$^+$ 283.07.

8-(4-fluoro-2-methoxyphenoxy)-6-methylindolizine-2-carbonitrile (33g)

(79%) $^1$H NMR (400 MHz, CDCl$_3$) δ 7.53 (d, J=1.7 Hz, 1H), 7.36-7.30 (m, 1H), 7.00 (dd, J=8.8, 5.7 Hz, 1H), 6.83-

6.78 (m, 1H), 6.71 (dd, J=10.1, 2.8 Hz, 1H), 6.62 (ddd, J=8.8, 7.9, 2.9 Hz, 1H), 3.73 (s, 3H), 2.05 (s, 3H). LC-MS (ES) for C$_{17}$H$_{13}$FN$_2$O$_2$ [M+1]$^+$297.10.

6-fluoro-8-(4-fluoro-2-methoxyphenoxy)indolizine-2-carbonitrile (33h)

(51%) $^1$H NMR (400 MHz, CDCl$_3$) δ 7.61 (d, J=1.7 Hz, 1H), 7.51 (ddd, J=4.1, 1.7, 0.9 Hz, 1H), 7.05 (dd, J=8.8, 5.7 Hz, 1H), 6.95 (dd, J=1.5, 0.9 Hz, 1H), 6.72 (dd, J=10.0, 2.8 Hz, 1H), 6.65 (ddd, J=8.8, 7.8, 2.9 Hz, 1H), 5.68 (dd, J=10.0, 1.7 Hz, 1H), 3.72 (s, 3H). LC-MS (ES) for C$_{16}$H$_{10}$F$_2$N$_2$O$_2$ [M+1]$^+$ 301.09.

6-chloro-8-(4-fluoro-2-methoxyphenoxy)indolizine-2-carbonitrile (33i)

(50%) $^1$H NMR (400 MHz, CDCl$_3$) δ 7.62-7.57 (m, 2H), 7.04 (dd, J=8.8, 5.7 Hz, 1H), 6.93 (s, 1H), 6.78-6.61 (m, 2H), 5.68 (d, J=1.3 Hz, 1H), 3.72 (s, 3H). LC-MS (ES) for C$_{15}$H$_{10}$ClFN$_2$O$_2$ [M+1]$^+$ 317.05.

8-(5-fluoro-2-methoxyphenoxy)indolizine-2-carbonitrile (33j)

(41%) $^1$H NMR (400 MHz, CDCl$_3$) δ 7.64 (d, J=1.6 Hz, 1H), 7.57 (d, J=6.9 Hz, 1H), 6.94-6.84 (m, 2H), 6.83 (s, 1H), 6.78 (dd, J=8.7, 2.9 Hz, 1H), 6.43 (t, J=7.2 Hz, 1H), 5.89 (d, J=7.4 Hz, 1H), 3.74 (s, 3H). LC-MS (ES) for C$_{16}$H$_{11}$FN$_2$O$_2$ [M+1]$^+$ 283.06.

8-(4,5-difluoro-2-methoxyphenoxy)indolizine-2-carbonitrile (33k)

(50%) $^1$H NMR (500 MHz, CDCl$_3$) δ 7.69 (d, J=1.6 Hz, 1H), 7.61 (d, J=7.0 Hz, 1H), 6.97 (dd, J=10.2, 7.9 Hz, 1H), 6.89 (s, 1H), 6.85 (dd, J=11.6, 7.4 Hz, 1H), 6.46 (t, J=7.2 Hz, 1H), 5.85 (d, J=7.4 Hz, 1H), 3.76 (s, 3H). LC-MS (ES) for C$_{16}$H$_{10}$F$_2$N$_2$O$_2$ [M+1]$^+$ 301.08.

8-(4,5-difluoro-2-methoxyphenoxy)-6-fluoroindolizine-2-carbonitrile (33l)

(55%) $^1$H NMR (400 MHz, CDCl$_3$) δ 7.63 (d, J=1.7 Hz, 1H), 7.54 (ddd, J=4.1, 1.7, 0.9 Hz, 1H), 6.99 (dd, J=10.0, 7.8 Hz, 1H), 6.95-6.91 (m, 1H), 6.83 (dd, J=11.5, 7.3 Hz, 1H), 5.72 (dd, J=9.8, 1.7 Hz, 1H), 3.71 (s, 3H). LC-MS (ES) for C$_{16}$H$_9$F$_3$N$_2$O$_2$ [M+1]$^+$ 319.08.

8-(4-chloro-2-methoxyphenoxy)indolizine-2-carbonitrile (33m)

(74%) $^1$H NMR (400 MHz, CDCl$_3$) δ 7.75 (d, J=1.6 Hz, 1H), 7.65 (d, J=6.9 Hz, 1H), 7.08 (d, J=2.3 Hz, 1H), 6.81 (s, 1H), 6.88 (d, J=1.9 Hz, 1H), 6.82 (d, J=1.2 Hz, 1H), 6.27 (t, J=7.2 Hz, 1H), 5.98 (d, J=7.4 Hz, 1H), 3.86 (s, 3H). LC-MS (ES) for C$_{15}$H$_9$ClN$_2$O$_2$ [M+1]$^+$ 285.49.

6-chloro-8-(4-chloro-2-methoxyphenoxy)indolizine-2-carbonitrile (33n)

(73%) $^1$H NMR (400 MHz, CDCl$_3$) δ 7.53 (d, J=1.8 Hz, 1H), 7.31 (d, J=1.4, 1.0 Hz, 1H), 7.01 (dd, J=1.8, 0.9 Hz, 1H), 6.78-6.72 (m, 2H), 6.34 (d, J=1.5 Hz, 1H), 5.47 (d, J=1.8 Hz, 1H), 3.70 (s, 3H). LC-MS (ES) for C$_{16}$H$_{10}$Cl$_2$N$_2$O$_2$ [M+1]$^+$ 334.10.

Step 5

A solution of BBr$_3$ (2.5 equiv, 1.0M in DCM) was added dropwise to a solution of the corresponding diether intermediate (1.0 equiv) in anhydrous DCM (1.0 mL per mmol diether intermediate) under N$_2$ atmosphere at −78° C. The reaction mixture was stirred for an additional 3h at 0° C. After this period, the solution was quenched with ice water, and the organic layer washed with water. The organic layer was dried over anhydrous Na$_2$SO$_4$, concentration by rotary evaporation, and purified by column chromatography to give 34a-n.

2-((2-methylindolizin-8-yl)oxy)phenol (34a)

(64%) $^1$H NMR (400 MHz, CDCl$_3$) δ 7.31 (d, J=8.2 Hz, 1H), 7.10-6.92 (m, 4H), 6.60 (dd, J=8.1, 1.2 Hz, 1H), 6.17-6.09 (m, 3H), 2.08 (s, 3H). LC-MS (ES) for C$_{15}$H$_{13}$NO$_2$ [M+1]$^+$ 240.01.

8-(2-hydroxyphenoxy)indolizine-2-carbonitrile (34b)

(94%) $^1$H NMR (400 MHz, CDCl$_3$) δ 7.59 (d, J=7.0 Hz, 1H), 7.10-7.05 (m, 2H), 6.47 (t, J=7.2 Hz, 1H). LC-MS (ES) for C$_{15}$H$_{10}$N$_2$O$_2$ [M+1]$^+$ 250.21

8-(2-hydroxyphenoxy)-6-methylindolizine-2-carbonitrile (34c)

(40%) $^1$H NMR (400 MHz, CDCl$_3$) δ 7.48 (d, J=1.9 Hz, 1H), 7.32 (s, 1H), 7.02-6.93 (m, 2H), 6.88 (d, J=8.0 Hz, 1H), 6.77 (t, J=8.0 Hz, 1H), 6.68 (s, 1H), 5.79 (s 1H), 5.35 (s, 1H), 2.00 (s, 3H). LC-MS (ES) for C$_{16}$H$_{12}$N$_2$O$_2$ [M+1]$^+$ 265.20.

6-fluoro-8-(2-hydroxyphenoxy)indolizine-2-carbonitrile (34d)

(57%) $^1$H NMR (400 MHz, CDCl$_3$) δ 7.61 (d, J=2.0 Hz, 1H), 7.51 (ddd, J=4.0, 1.7, 0.9 Hz, 1H), 7.26-7.17 (m, 1H), 6.95 (td, J=8.3, 1.5 Hz, 2H), 6.86-6.78 (m, 2H), 5.87 (dd, J=9.7, 1.7 Hz, 1H), 5.25 (s, 1H). LC-MS (ES) for C$_{15}$H$_9$FN$_2$O$_2$ [M+1]$^+$ 269.02.

6-chloro-8-(2-hydroxyphenoxy)indolizine-2-carbonitrile (34e)

(41%) $^1$H NMR (400 MHz, Acetone-d$_6$) δ 7.60-7.57 (m, 1H), 7.59 (d, J=1.7 Hz, 1H), 7.02-6.91 (m, 4H), 6.82 (d, J=1.0 Hz, 1H), 5.83 (s, 1H), 5.53 (br, 1H). LC-MS (ES) for C$_{15}$H$_9$ClN$_2$O$_2$ [M+1]$^+$ 285.25.

8-(4-fluoro-2-hydroxyphenoxy)indolizine-2-carbonitrile (34f)

(52%) $^1$H NMR (400 MHz, CDCl$_3$) δ 7.67 (d, J=1.6 Hz, 1H), 7.61 (d, J=7.0 Hz, 1H), 6.93 (dd, J=9.0, 5.3 Hz, 1H), 6.86-6.82 (m, 1H), 6.77 (dd, J=9.4, 2.9 Hz, 1H), 6.71 (dd, J=8.8, 5.2 Hz, 1H), 6.20 (t, J=7.2 Hz, 1H), 5.98 (d, J=7.4 Hz, 1H), 5.41 (s, 1H). LC-MS (ES) for C$_{15}$H$_9$FN$_2$O$_2$ [M+1]$^+$ 269.00.

8-(4-fluoro-2-hydroxyphenoxy)-6-methylindolizine-2-carbonitrile (34g)

(45%) $^1$H NMR (400 MHz, CDCl$_3$) δ 7.58 (d, J=1.6 Hz, 1H), 7.35-7.30 (m, 1H), 7.05 (dd, J=8.8, 5.7 Hz, 1H), 6.83-6.78 (m, 1H), 6.60-6.56 (m, 2H), 5.81 (s, 1H), 5.43 (s, 1H), 2.05 (s, 3H). LC-MS (ES) for C$_{16}$H$_{11}$FN$_2$O$_2$ [M+1]$^+$ 283.09.

6-fluoro-8-(4-fluoro-2-hydroxyphenoxy)indolizine-2-carbonitrile (34h)

(52%) $^1$H NMR (400 MHz, CDCl$_3$) δ 7.78 (d, J=1.6 Hz, 1H), 7.60 (ddd, J=4.0, 1.6, 0.9 Hz, 1H), 7.11 (dd, J=8.8, 5.7 Hz, 1H), 6.91 (dd, J=1.6, 0.9 Hz, 1H), 6.70 (dd, J=10.0, 2.9 Hz, 1H), 6.64 (ddd, J=8.8, 7.8, 2.9 Hz, 1H), 5.72 (dd, J=10.0, 1.7 Hz, 1H), 5.42 (s, 1H). LC-MS (ES) for C$_{15}$H$_8$F$_2$N$_2$O$_2$ [M+1]$^+$ 287.03.

6-chloro-8-(4-fluoro-2-hydroxyphenoxy)indolizine-2-carbonitrile (34i)

(49%) $^1$H NMR (400 MHz, CDCl$_3$) δ 7.59-7.57 (m, 1H), 7.52 (d, J=1.6 Hz, 1H), 6.89 (dd, J=8.9, 5.4 Hz, 1H), 6.82 (d, J=1.0 Hz, 1H), 6.70 (dt, J=9.3, 2.6 Hz, 1H), 6.53 (ddt, J=8.9, 7.9, 2.9 Hz, 1H), 5.83 (d, J=1.3 Hz, 1H), 5.53 (br, 1H). LC-MS (ES) calcd for C$_{15}$H$_8$ClFN$_2$O$_2$ [M+1]$^+$ 303.29.

8-(5-fluoro-2-hydroxyphenoxy)indolizine-2-carbonitrile (34j)

(61%) $^1$H NMR (400 MHz, CDCl$_3$) δ 7.68 (d, J=1.6 Hz, 1H), 7.65 (d, J=7.2 Hz, 1H), 6.98 (q, J=4.4 Hz, 1H), 6.80-6.76 (m, 2H), 6.69 (dd, J=8.7, 2.9 Hz, 1H), 6.49 (t, J=7.4 Hz, 1H), 6.13 (d, J=7.4 Hz, 1H), 5.19 (s, 1H). LC-MS (ES) for C$_{15}$H$_9$FN$_2$O$_2$ [M+1]$^+$ 269.08.

8-(4,5-difluoro-2-hydroxyphenoxy)indolizine-2-carbonitrile (34k)

(68%) $^1$H NMR (500 MHz, CDCl$_3$) δ 7.61 (d, J=1.4 Hz, 1H), 7.56 (s, 1H), 6.85-6.69 (m, 3H), 6.40 (t, J=7.3 Hz, 1H), 5.96 (d, J=7.4 Hz, 1H), 5.63 (s, 1H). LC-MS (ES) for C$_{16}$H$_{10}$F$_2$N$_2$O$_2$ [M+1]$^+$ 301.09.

8-(4,5-difluoro-2-hydroxyphenoxy)-6-fluoroindolizine-2-carbonitrile (34l)

(76%) $^1$H NMR (400 MHz, CDCl$_3$) δ 7.67 (d, J=1.6 Hz, 1H), 7.62 (d, J=3.2 Hz, 1H), 6.96-6.84 (m, 3H), 5.98 (dd, J=9.4, 1.7 Hz, 1H), 5.23 (S, 1H). LC-MS (ES) for C$_{15}$H$_7$F$_3$N$_2$O$_2$ [M+1]$^+$ 305.05.

8-(4-chloro-2-hydroxyphenoxy)indolizine-2-carbonitrile (34m)

(33%) $^1$H NMR (400 MHz, CDCl$_3$) δ 7.68 (d, J=1.6 Hz, 1H), 7.62 (d, J=7.0 Hz, 1H), 7.05 (d, J=2.4 Hz, 1H), 6.87 (s, 1H), 6.84-6.79 (m, 2H), 6.47 (t, J=7.2 Hz, 1H), 6.05 (d, J=7.4 Hz, 1H), 5.39 (s, 1H). LC-MS (ES) for C$_{14}$H$_7$ClN$_2$O$_2$ [M+1]$^+$ 271.57.

6-chloro-8-(4-chloro-2-hydroxyphenoxy)indolizine-2-carbonitrile (34n)

(39%) $^1$H NMR (400 MHz, CDCl$_3$) δ 7.61 (d, J=1.6 Hz, 1H), 7.38 (dd, J=1.4, 1.0 Hz, 1H), 7.06 (dd, J=1.8, 0.9 Hz, 1H), 6.89-6.83 (m, 2H), 6.67 (d, J=1.5 Hz, 1H), 5.74 (d, J=1.5 Hz, 1H), 5.23 (s, 1H). LC-MS (ES) for C$_{15}$H$_8$Cl$_2$N$_2$O$_2$ [M+1]$^+$ 320.09.

Step 6

17 (1.2 equiv) and K$_2$CO$_3$ (2.0 equiv) were added to a solution of the corresponding catechol aryl ether intermediate (1.0 equiv) in anhydrous DMF (1.0 mL per mmol catechol aryl ether intermediate) and the mixture was stirred for 3 h at 60° C. to complete the reaction. The reaction mixture was poured into brine and extracted with ethyl acetate. The organic layer was sequentially washed with brine, dried over anhydrous Na$_2$SO$_4$, and concentration by rotary evaporation. The crude product was dissolved in DCM (0.5 mL per mmol catechol diether intermediate) and NH$_4$OH (0.5 mL per mmol catechol aryl ether intermediate) were added. The reaction mixture was stirred at room temperature for 16 h. After completion, the reaction mixture was concentrated by rotary evaporation and purified by column chromatography to give 10a-n.

1-(2-(2-((2-methylindolizin-8-yl)oxy)phenoxy)ethyl)pyrimidine-2,4(1H,3H)-dione (10a)

(36%) $^1$H NMR (400 MHz, Acetone-d$_6$) δ 9.89-9.70 (m, 1H), 7.80 (d, J=6.8 Hz, 1H), 7.38 (d, J=0.7 Hz, 1H), 7.31-7.11 (m, 3H), 7.09-7.01 (m, 1H), 6.83 (d, J=7.9 Hz, 1H), 6.45 (s, 1H), 6.26 (s, 1H), 5.69-5.56 (m, 1H), 4.84-4.64 (m, 1H), 4.30-4.17 (m, 2H), 4.04-3.87 (m, 2H), 2.34 (s, 3H). $^{13}$C NMR (126 MHz, CDCl$_3$) δ 164.29, 158.44, 150.60, 149.95, 145.73, 143.75, 140.21, 134.36, 125.50, 122.62, 122.25, 119.35, 115.10, 111.53, 101.12, 96.83, 66.26, 47.98, 21.24. HRMS (ES) calcd for C$_{21}$H$_{19}$N$_3$O$_4$ [M+1]$^+$ 378.1271. found 378.1270.

8-(2-(2-(2,4-dioxo-3,4-dihydropyrimidin-1(2H)-yl)ethoxy)phenoxy)indolizine-2-carbonitrile (10b)

(51%) $^1$H NMR (400 MHz, Acetone-d$_6$) δ 9.81 (s, 1H), 8.19 (d, J=1.7 Hz, 1H), 7.96 (d, J=7.0 Hz, 1H), 7.40-7.02 (m, 4H), 7.02-6.78 (m, 2H), 6.56 (t, J=7.2 Hz, 1H), 5.78 (d, J=7.4 Hz, 1H), 4.71 (d, J=7.9 Hz, 1H), 4.33-4.19 (m, 2H), 4.07-3.95 (m, 2H). $^{13}$C NMR (126 MHz, Acetone-d$_6$) δ 163.67, 151.51, 150.91, 146.29, 143.16, 128.41, 127.75, 123.89, 122.75, 120.99, 120.49, 116.66, 115.16, 113.59, 101.06, 100.68, 99.57, 97.52, 67.16, 48.58. HR-MS (ES) calcd for C$_{21}$H$_{16}$N$_4$O$_4$ [M+1]$^+$ 389.1245. found 389.1247.

8-(2-(2-(2,4-dioxo-3,4-dihydropyrimidin-1(2H)-yl)ethoxy)phenoxy)-6-methylindolizine-2-carbonitrile (10c)

(36%) $^1$H NMR (400 MHz, DMSO-d$_6$) δ 11.21 (s, 1H), 8.27 (d, J=1.7 Hz, 1H), 7.83-7.76 (m, 1H), 7.39-7.24 (m, 3H), 7.12 (td, J=7.9, 1.7 Hz, 1H), 7.04-6.95 (m, 2H), 5.58 (s, 1H), 4.70 (dd, J=7.8, 2.2 Hz, 1H), 4.24 (t, J=4.9 Hz, 2H), 3.95 (t, J=4.8 Hz, 2H), 2.06 (s, 3H). $^{13}$C NMR (126 MHz, DMSO-d$_6$) 163.27, 150.65, 150.08, 148.71, 145.56, 141.48, 126.90, 125.68, 122.82, 122.03, 121.86, 119.63, 117.58, 116.54, 114.50, 101.68, 100.04, 99.46, 95.02, 65.86, 47.26, 17.91. HR-MS (ES) calcd for C$_{22}$H$_{18}$N$_4$O$_4$ [M+1]$^+$ 403.1406. found 403.1368.

8-(2-(2-(2,4-dioxo-3,4-dihydropyrimidin-1(2H)-yl)ethoxy)phenoxy)-6-fluoroindolizine-2-carbonitrile (10d)

(65%) $^1$H NMR (400 MHz, DMSO-d$_6$) δ 11.21 (s, 1H), 8.37 (d, J=1.6 Hz, 1H), 8.26 (d, J=3.9 Hz, 1H), 7.44-7.28 (m, 3H), 7.21-7.09 (m, 2H), 7.04 (d, J=7.8 Hz, 1H), 5.75 (dd, J=10.1, 1.6 Hz, 1H), 4.71 (d, J=7.8 Hz, 1H), 4.25 (t, J=4.8 Hz, 2H), 3.97 (t, J=4.7 Hz, 2H). $^{13}$C NMR (126 MHz, DMSO-d$_6$) δ 163.62, 154.69, 152.84, 151.02, 150.24, 146.01, 141.29, 127.91, 125.01, 123.23, 122.29, 116.43, 114.89, 107.42, 107.07, 102.12, 99.76, 96.43, 93.04, 66.20, 47.55. HR-MS (ES) calcd for C$_{21}$H$_{15}$FN$_4$O$_4$ [M+1]$^+$ 407.1156. found 407.1114.

8-(4-chloro-2-(2-(2,4-dioxo-3,4-dihydropyrimidin-1 (2H)-yl)ethoxy)phenoxy)indolizine-2-carbonitrile (10e)

(41%) $^1$H NMR (400 MHz, CDCl$_3$) δ 8.49 (s, 1H), 7.67 (d, J=1.6 Hz, 1H), 7.61 (d, J=1.0 Hz, 1H), 7.06-7.00 (m, 3H), 6.97 (d, J=2.1 Hz, 1H), 6.92 (s, 1H), 6.61 (d, J=7.9 Hz, 1H), 5.53 (d, J=1.3 Hz, 1H), 4.63 (dd, J=7.9, 2.2 Hz, 1H), 4.15 (t, J=4.7 Hz, 2H), 3.92 (t, J=4.7 Hz, 2H). $^{13}$C NMR (126 MHz, CDCl$_3$) δ 163.11, 150.82, 150.65, 150.09, 145.33, 140.59, 133.02, 125.91, 124.53, 123.08, 121.85, 119.71, 118.03, 115.80, 115.42, 110.54, 102.68, 101.10, 98.40, 66.76, 48.85. HR-MS (ES) calcd for C$_{21}$H$_{15}$ClN$_4$O$_4$ [M+1]$^+$ 423.0860. found 423.0862.

8-(2-(2-(2,4-dioxo-3,4-dihydropyrimidin-1(2H)-yl) ethoxy)-4-fluorophenoxy)indolizine-2-carbonitrile (10f)

(33%) $^1$H NMR (400 MHz, DMSO-d$_6$) δ 11.16 (s, 1H), 8.34 (d, J=1.5 Hz, 1H), 7.98 (d, J=6.9 Hz, 1H), 7.26 (ddd, J=26.6, 9.7, 4.3 Hz, 2H), 7.01 (s, 1H), 6.97-6.84 (m, 2H), 6.54 (t, J=7.2 Hz, 1H), 5.73 (d, J=7.4 Hz, 1H), 4.66 (dd, J=7.8, 1.6 Hz, 1H), 4.20 (t, J=4.8 Hz, 2H), 3.90 (t, J=4.7 Hz, 2H). $^{13}$C NMR (101 MHz, DMSO-d$_6$) δ 163.25, 158.88, 150.95, 150.64, 149.32, 145.55, 137.78, 126.64, 123.84, 120.32, 120.22, 116.40, 112.63, 107.67, 102.72, 100.11, 99.52, 98.58, 95.57, 66.31, 46.83. HR-MS (ES) calcd for C$_{21}$H$_{15}$FN$_4$O$_4$ [M+1]$^+$ 407.1156. found 407.1139.

8-(2-(2-(2,4-dioxo-3,4-dihydropyrimidin-1(2H)-yl) ethoxy)-4-fluorophenoxy)-6-methylindolizine-2-carbonitrile (10g)

(50%) $^1$H NMR (400 MHz, DMSO-d$_6$) δ 11.21 (s, 1H), 8.26 (d, J=1.7 Hz, 1H), 7.82-7.75 (m, 1H), 7.30 (ddd, J=19.4, 9.7, 4.4 Hz, 2H), 7.04-6.86 (m, 3H), 5.60 (s, 1H), 4.66 (dd, J=7.8, 2.2 Hz, 1H), 4.25 (t, J=4.8 Hz, 2H), 3.95 (t, J=4.8 Hz, 2H), 2.06 (s, 3H). $^{13}$C NMR (126 MHz, DMSO-d$_6$) δ 163.64, 161.43, 159.50, 151.51, 151.02, 149.13, 145.84, 138.09, 125.95, 124.18, 122.43, 120.02, 116.91, 108.11, 103.18, 101.87, 100.42, 99.86, 95.43, 66.68, 47.43, 18.28. HR-MS (ES) calcd for C$_{22}$H$_{17}$FN$_4$O$_4$ [M+1]$^+$ 421.1312. found 421.1277.

8-(2-(2-(2,4-dioxo-3,4-dihydropyrimidin-1(2H)-yl) ethoxy)-4-fluorophenoxy)-6-fluoroindolizine-2-carbonitrile (10h)

(46%) $^1$H NMR (500 MHz, Acetone-d$_6$) δ 9.82 (s, 1H), 8.21 (d, J=1.7 Hz, 1H), 8.08 (ddd, J=4.6, 1.8, 0.9 Hz, 1H), 7.38 (ddd, J=8.2, 7.5, 1.6 Hz, 1H), 7.31 (ddd, J=10.1, 8.1, 1.5 Hz, 1H), 7.14 (td, J=7.7, 1.5 Hz, 1H), 7.10 (dd, J=1.6, 0.9 Hz, 1H), 6.97 (d, J=7.9 Hz, 1H), 5.76 (dd, J=10.2, 1.8 Hz, 1H), 4.72 (dd, J=7.9, 2.1 Hz, 1H), 4.32 (t, J=4.9 Hz, 2H), 4.04 (t, J=4.9 Hz, 2H). $^{13}$C NMR (126 MHz, Acetone-d$_6$) δ 163.19, 153.59, 151.05, 150.87, 145.84, 141.98, 127.94, 125.75, 123.44, 122.40, 121.48, 115.84, 114.77, 107.17, 106.83, 102.09, 100.09, 93.08, 92.86, 66.58, 48.17. HR-MS (ES) calcd for C$_{21}$H$_{14}$F$_2$N$_4$O$_4$ [M+1]$^+$ 425.1061. found 425.1058.

6-chloro-8-(2-(2-(2,4-dioxo-3,4-dihydropyrimidin-1 (2H)-yl)ethoxy)-4-fluorophenoxy)indolizine-2-carbonitrile (10i)

(41%) $^1$H NMR (500 MHz, CDCl$_3$) δ 8.10 (s, 1H), 7.67 (d, J=1.6 Hz, 1H), 7.60 (s, 1H), 7.08 (dd, J=8.6, 5.6 Hz, 1H), 6.93 (s, 1H), 6.72 (ddt, J=12.3, 6.5, 2.8 Hz, 3H), 6.61 (d, J=7.9 Hz, 1H), 5.52 (d, J=1.2 Hz, 1H), 4.60 (dd, J=7.9, 2.1 Hz, 1H), 4.14 (t, J=4.7 Hz, 2H), 3.92 (t, J=4.7 Hz, 2H). $^{13}$C NMR (126 MHz, CDCl$_3$) δ 162.55, 162.00, 150.70, 150.17, 150.00, 144.98, 137.46, 125.63, 124.00, 121.52, 119.26, 117.50, 115.48, 108.92, 102.58, 102.27, 100.64, 100.44, 97.94, 66.23, 48.45. HR-MS (ES) calcd for C$_{21}$H$_{14}$ClFN$_4$O$_4$ [M+1]$^+$ 441.0766. found 441.0755.

8-(2-(2-(2,4-dioxo-3,4-dihydropyrimidin-1(2H)-yl) ethoxy)-5-fluorophenoxy)indolizine-2-carbonitrile (10j)

(37%) $^1$H NMR (500 MHz, CDCl$_3$) δ 8.90 (s, 1H), 7.70 (d, J=1.6 Hz, 1H), 7.57 (d, J=6.9 Hz, 1H), 6.89 (dd, J=6.3, 1.4 Hz, 2H), 6.86-6.80 (m, 2H), 6.66 (d, J=7.9 Hz, 1H), 6.34 (t, J=7.2 Hz, 1H), 5.66 (d, J=7.4 Hz, 1H), 4.70 (d, J=7.9 Hz, 1H), 4.11 (t, J=4.7 Hz, 2H), 3.91 (t, J=4.6 Hz, 2H). $^{13}$C NMR (126 MHz, CDCl$_3$) δ 163.15, 158.39, 156.42, 150.56, 149.47, 146.46, 145.21, 127.08, 120.03, 119.00, 115.91, 115.15, 112.94, 112.62, 111.03, 100.96, 100.77, 99.16, 97.37, 67.05, 48.42. HR-MS (ES) calcd for C$_{21}$H$_{15}$FN$_4$O$_4$ [M+1]$^+$ 407.1156. found 407.1134.

8-(2-(2-(2,4-dioxo-3,4-dihydropyrimidin-1(2H)-yl) ethoxy)-4,5-difluorophenoxy)indolizine-2-carbonitrile (10k)

(48%) $^1$H NMR (500 MHz, DMSO-d$_6$) δ 11.20 (s, 1H), 8.39 (d, J=1.7 Hz, 1H), 8.05 (d, J=7.0 Hz, 1H), 7.58 (ddd, J=28.5, 11.6, 8.0 Hz, 2H), 7.04 (s, 1H), 6.99 (d, J=7.8 Hz, 1H), 6.60 (t, J=7.2 Hz, 1H), 5.89 (d, J=7.4 Hz, 1H), 4.75 (d, J=7.8 Hz, 1H), 4.23 (t, J=4.9 Hz, 2H), 3.94 (t, J=4.9 Hz, 2H). $^{13}$C NMR (126 MHz, DMSO-d$_6$) δ 163.25, 150.63, 148.90, 146.83, 146.76, 145.53, 126.44, 120.68, 120.31, 116.35, 112.55, 112.48, 112.32, 104.30, 104.12, 100.09, 99.57, 99.13, 95.64, 66.83, 46.83. HR-MS (ES) calcd for C$_{21}$H$_{15}$FN$_4$O$_4$ [M+1]$^+$ 425.1061. found 425.1044.

8-(2-(2-(2,4-dioxo-3,4-dihydropyrimidin-1(2H)-yl) ethoxy)-4,5-difluorophenoxy)-6-fluoroindolizine-2-carbonitrile (10l)

(48%) $^1$H NMR (400 MHz, CDCl$_3$) δ 8.70 (s, 1H), 7.77 (d, J=1.8 Hz, 1H), 7.64 (d, J=7.9 Hz, 1H), 7.11-7.07 (m, 1H), 6.99 (s, 1H), 6.92-6.91 (m, 1H), 6.69 (d, J=7.7 Hz, 1H), 5.58 (dd, J=9.4, 1.8 Hz, 1H), 4.75 (d, J=7.6 Hz, 1H), 4.19 (t, J=4.3 Hz, 2H), 3.99 (t J=4.3 Hz, 2H). $^{13}$C NMR (126 MHz, CDCl$_3$) 162.70, 154.94, 153.05, 150.28, 144.91, 124.82, 120.32, 115.43, 112.80, 112.65, 106.77, 106.44, 104.35, 104.17, 102.34, 100.79, 97.89, 93.16, 92.91, 67.09, 48.39. HR-MS (ES) calcd for C$_{21}$H$_{13}$F$_3$N$_4$O$_4$ [M+1]$^+$ 443.0967. found 443.0935.

8-(4-chloro-2-(2-(2,4-dioxo-3,4-dihydropyrimidin-1 (2H)-yl)ethoxy)phenoxy)indolizine-2-carbonitrile (10m)

(39%) $^1$H NMR (500 MHz, DMSO-d$_6$) δ 10.96 (s, 1H), 8.14 (d, J=1.6 Hz, 1H), 7.79 (d, J=6.9 Hz, 1H), 7.18 (d, J=2.3 Hz, 1H), 7.07 (d, J=8.5 Hz, 1H), 6.91 (dd, J=8.5, 2.3 Hz, 1H), 6.83-6.72 (m, 2H), 6.34 (t, J=7.2 Hz, 1H), 5.58 (d, J=7.4 Hz, 1H), 4.51 (dd, J=7.8, 2.2 Hz, 1H), 4.02 (t, J=4.9 Hz, 2H), 3.69 (t, J=4.8 Hz, 2H). $^{13}$C NMR (126 MHz, DMSO-d$_6$) δ 163.27, 150.71, 150.65, 148.91, 145.55, 140.64, 130.50, 126.60, 123.98, 121.46, 120.56, 120.28, 116.36, 114.82, 112.60, 100.13, 99.59, 99.19, 95.62, 66.35, 46.83. HR-MS (ES) calcd for $C_{21}H_{15}ClN_4O_4$ [M+1]$^+$ 423.0860. found 423.0838.

6-chloro-8-(4-chloro-2-(2-(2,4-dioxo-3,4-dihydropyrimidin-1(2H)-yl)ethoxy)phenoxy)indolizine-2-carbonitrile (10n)

(38%) $^1$H NMR (400 MHz, DMSO-$d_6$) δ 11.22 (s, 1H), 8.37 (d, J=1.7 Hz, 1H), 8.27 (d, J=4.0 Hz, 1H), 7.40 (dd, J=8.8, 5.8 Hz, 1H), 7.35-7.27 (m, 1H), 7.18 (s, 1H), 7.02 (d, J=7.9 Hz, 1H), 7.01-6.92 m, 1H), 5.90-5.78 (m, 1H), 4.69 (d, J=7.5 Hz, 1H), 4.27 (t, J=4.6 Hz, 2H), 3.97 (t, J=4.6 Hz, 2H). $^{13}$C NMR (126 MHz, DMSO-$d_6$) δ 164.08, 151.31, 150.51, 146.90, 146.68, 130.19, 125.72, 124.02, 123.65, 122.11, 120.45, 119.70, 115.88, 115.79, 113.13, 113.01, 105.32, 100.81, 97.71, 67.17, 47.31. HR-MS (ES) calcd for $C_{21}H_{14}Cl_2N_4O_4$ [M+1]$^+$ 458.0470. found 458.0438.

Example 6

Synthesis of Compound 35

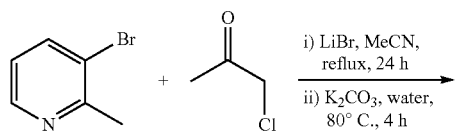

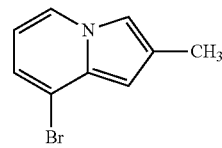

8-bromo-2-methylindolizine (35)

A mixture of cloroacetone (17 mmol), LiBr (17 mmol) in acetonitrile (10 mL) was stirred at room temperature for 15 min. Then, a solution of 2-bromo-3-methylpyridine (19 mmol) in acetonitrile (10 mL) was added and the resulting mixture was heated at reflux for 24 h. The mixture was cooled to room temperature and the solvent was removed under reduce pressure. The residue was diluted with water extracted with diethylether. The aqueous was treated with $K_2CO_3$ (96 mmol) and heated at 80° C. for 2 h. The mixture was cooled to room temperature and extracted with ethyl acetate (3×50 mL). The combined organic layer was washed with brine, dried over anhydrous $Na_2SO_4$, concentrated by rotary evaporation, and purified by column chromatography to give 35. (34%) $^1$H NMR (400 MHz, CDCl$_3$) δ 7.76 (dt, J=6.9, 0.8 Hz, 1H), 7.20-7.07 (m, 1H), 6.83 (dd, J=7.1, 0.7 Hz, 1H), 6.40 (s, 1H), 6.25 (t, J=7.0 Hz, 1H), 2.39 (s, 3H). LC-MS (ES) for $C_9H_8BrN$ [M+1]$^+$ 209.11.

Example 7

5. Synthesis of Compound 11a

Scheme 2.2

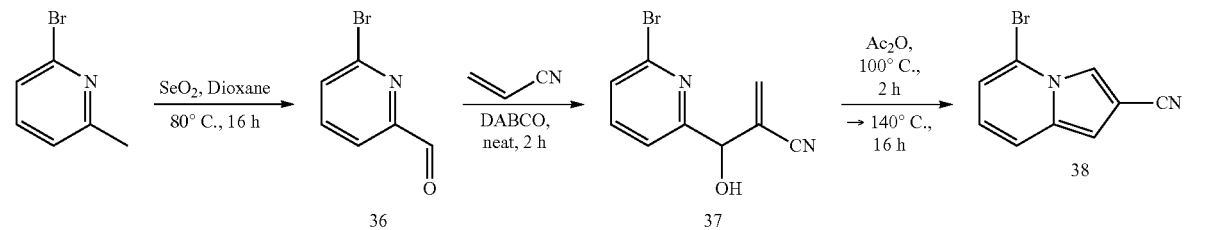

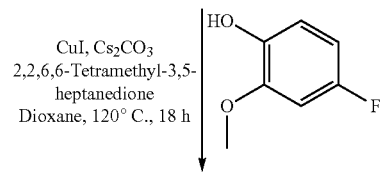

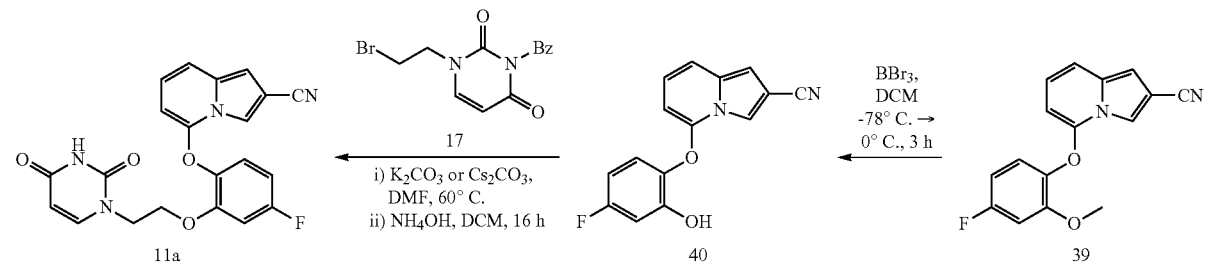

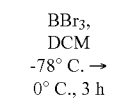

Step 1

6-bromopicolinaldehyde (36)

Following step A1 in the synthetic scheme 2.1 from 2-bromo-6-methylpyridine was obtained 36 after column chromatography. (71%) 1H NMR (400 MHz, CDCl$_3$) δ 9.77 (s, 1H), 7.84 (dd, J=7.8, 1.5 Hz, 1H), 7.76 (t, J=7.7 Hz, 1H), 7.70 (dd, J=7.7, 1.4 Hz, 1H). LC-MS (ES) for C$_6$H$_4$BrNO [M+1]$^+$ 187.37.

Step 2

2-((6-bromopyridin-2-yl)(hydroxy)methyl)acrylonitrile (37)

Following step 2 in the synthetic scheme 2.1 from 36 was obtained 37 after column chromatography. (84%) $^1$H NMR (400 MHz, CDCl$_3$) δ 7.57 (t, J=7.7 Hz, 1H), 7.44 (d, J=7.8 Hz, 1H), 7.33 (d, J=7.6 Hz, 1H), 6.20 (d, J=1.4 Hz, 2H), 5.22 (s, 1H), 4.37 (s, 1H). LC-MS (ES) for C$_9$H$_7$BrN$_2$O [M+1]$^+$ 240.04.

Step 3

5-bromoindolizine-2-carbonitrile (38)

Following step 2 in the synthetic scheme 2.1 from 37 was obtained 38 after column chromatography. (84%) $^1$H NMR (400 MHz, CDCl$_3$) δ 7.57 (t, J=7.7 Hz, 1H), 7.44 (d, J=7.8 Hz, 1H), 7.33 (d, J=7.6 Hz, 1H), 6.20 (d, J=1.4 Hz, 2H), 5.22 (s, 1H), 4.37 (s, 1H). LC-MS (ES) for C$_9$H$_7$BrN$_2$O [M+1]$^+$ 240.04.

Step 4

5-(4-fluoro-2-methoxyphenoxy)indolizine-2-carbonitrile (39)

Following step 3 in the synthetic scheme 2.1 from 38 was obtained 39 after column chromatography. (30%) $^1$H NMR (400 MHz, CDCl$_3$) δ 7.81 (dd, J=7.1, 1.0 Hz, 1H), 7.62-7.56 (m, 1H), 7.30 (d, J=9.2 Hz, 1H), 6.75-6.69 (m, 2H), 6.69-6.63 (m, 1H), 6.61 (s, 1H), 6.56 (td, J=7.0, 1.2 Hz, 1H), 3.70 (s, 3H). LC-MS (ES) for C$_{16}$H$_{11}$FN$_2$O$_2$ [M+1]$^+$ 283.01.

Step 5

5-(4-fluoro-2-hydroxyphenoxy)indolizine-2-carbonitrile (40)

Following step 4 in the synthetic scheme 2.1 from 39 was obtained 40 after column chromatography. (37%) $^1$H NMR (400 MHz, CDCl$_3$) δ 7.90 (dd, J=1.6, 0.7 Hz, 1H), 7.62-7.56 (m, 1H), 7.09 (d, J=9.1 Hz, 1H), 7.01 (dd, J=9.0, 5.3 Hz, 1H), 6.79 (dd, J=9.3, 2.9 Hz, 1H), 6.71-6.66 (m, 2H), 6.56 (td, J=7.0, 1.2 Hz, 1H), 5.62 (s, 1H). LC-MS (ES) for C$_{15}$H$_9$FN$_2$O$_2$ [M+1]$^+$ 269.07.

Step 6

5-(2-(2-(2,4-dioxo-3,4-dihydropyrimidin-1(2H)-yl)ethoxy)-4-fluorophenoxy)indolizine-2-carbonitrile (11a)

Following step 6 in the synthetic scheme 2.1 from 40 was obtained 11a after column chromatography. (29%) $^1$H NMR (500 MHz, CDCl$_3$) δ 7.94 (d, J=1.3 Hz, 1H), 7.78 (s, 1H), 7.16 (dd, J=8.8, 5.5 Hz, 1H), 7.07 (d, J=9.0 Hz, 1H), 6.77-6.67 (m, 3H), 6.66-6.56 (m, 1H), 6.24 (d, J=7.9 Hz, 1H), 5.46 (d, J=6.8 Hz, 1H), 4.69 (dd, J=7.9, 2.4 Hz, 1H), 4.10 (t, J=4.6 Hz, 2H), 3.85 (t, J=4.6 Hz, 2H). $^{13}$C NMR (126 MHz, CDCl$_3$) δ 163.85, 159.79, 157.87, 156.65, 151.38, 151.15, 146.46, 144.08, 142.41, 139.81, 134.98, 128.86, 121.44, 120.34, 116.37, 116.09, 106.46, 101.82, 101.10, 68.89, 48.72. HR-MS (ES) calcd for C$_{21}$H$_{15}$FN$_4$O$_4$ [M+1]$^+$ 407.1156. found 407.1129.

Example 8

6. Synthesis of Compounds 12 a-h

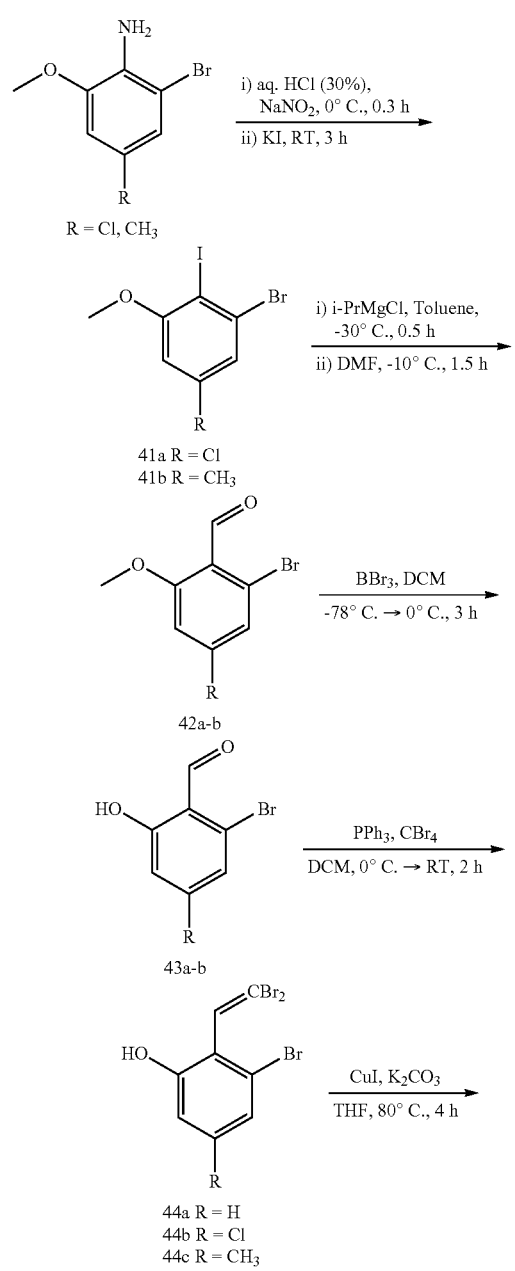

Scheme 3.1

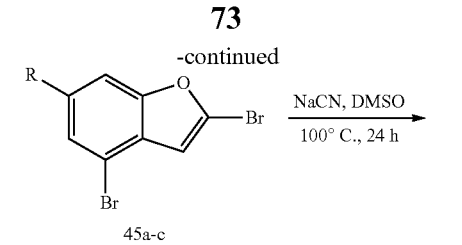

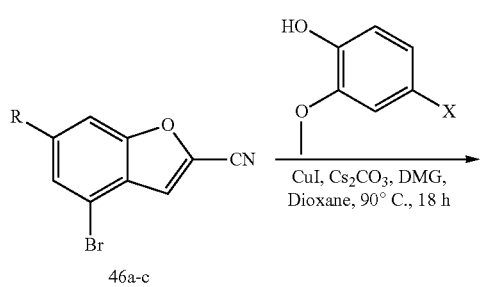

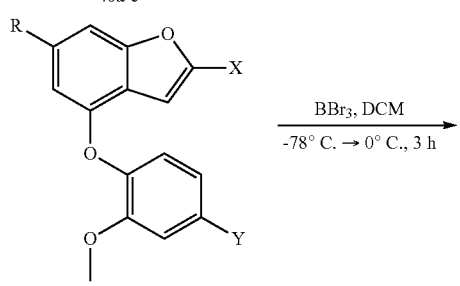

47a R = H, X = CN, Y = H
47b R = CH₃, X = CN, Y = H
47c R = Cl, X = CN, Y = F
47d R = H, X = CN, Y = F
47e R = CH₃, X = CN, Y = F
47g R = H, X = CH₃, Y = Cl
47h R = H, X = CN, Y = Cl

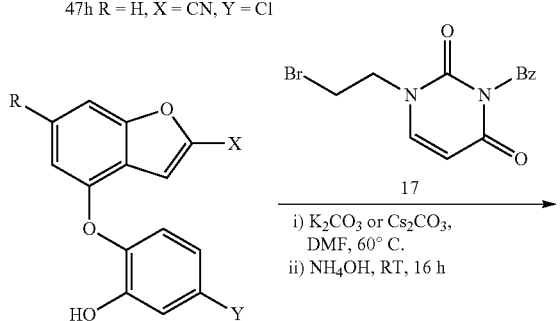

48a R = H, X = CN, Y = H
48b R = CH₃, X = CN, Y = H
48c R = Cl, X = CN, Y = F
48d R = H, X = CN, Y = F
48e R = CH₃, X = CN, Y = F
48f R = H, X = H, Y = Cl
48g R = H, X = CH₃, Y = Cl
48h R = H, X = CN, Y = Cl

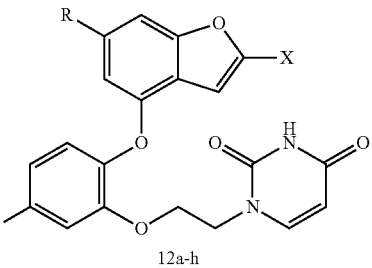

12a-h

Step 1

The mixture of the corresponding aniline (1.0 equiv), and 50% aq. HCl (30%) in acetonitrile was cooled to 0° C., then a solution of NaNO₂ (1.5 equiv) in H₂O (5.0 mL per mmol aniline) was added and stirred for 20 min. Then, a solution of KI (2.0 equiv) in H₂O (2.0 mL per mmol KI) was added dropwise to the above solution. After addition, the dark brown solid was started to precipitate and the mixture was allowed to warm to room temperature and stirred for an additional 3 h. The result solid was filtered, washed with 1N aq. HCl solution, and dried to give the corresponding iodobenzene intermediate 41a-b.

1-bromo-5-chloro-2-iodo-3-methoxybenzene (41a)

(91%) ¹H NMR (400 MHz, CDCl₃) δ 7.23 (d, J=2.1 Hz, 1H), 6.65 (d, J=2.1 Hz, 1H), 3.81 (s, 3H). LC-MS (ES) for $C_7H_5BrClIO$ [M+1]⁺ 348.06.

1-bromo-2-iodo-3-methoxy-5-methylbenzene (41b)

(83%) ¹H NMR (400 MHz, CDCl₃) δ 7.80 (s, 1H), 6.62 (s, 1H), 3.78 (s, 3H), 2.29 (s, 3H). LC-MS (ES) for $C_8H_8BrIO$ [M+1]⁺ 327.44.

Step 2

A solution of the corresponding iodobenzene intermediate (1.0 equiv) in toluene (5.0 mL per iodoaryl intermediate) was cooled to a temperature of −30° C. Then, a solution of isopropyl magnesium chloride (1.5 equiv, 2.0 M in THF) was added slowly over 0.5 h. A clear brown solution was obtained. Stirring was continued for 1 h. Anhydrous DMF (4.0 equiv) was added slowly over 5 min, the temperature of the reaction mixture increased to −19° C. The reaction mixture was warmed to 0° C. over 1 h. The reaction was quenched into saturated aqueous NH₄Cl, and allowed to warm to room temperature. Ethyl acetate and water were added and the layers were separated. The organic layer was washed with brine, concentrated by rotary evaporator, and purified by column chromatography to give 42a-b.

2-bromo-4-chloro-6-methoxybenzaldehyde (42a)

(91%) ¹H NMR (400 MHz, CDCl₃) δ 12.05 (s, 1H), 10.19 (d, J=0.5 Hz, 1H), 7.11 (d, J=1.9 Hz, 1H), 6.91 (dd, J=1.9, 0.6 Hz, 2H). LC-MS (ES) for $C_7H_4BrClO_2$ [M+1]⁺ 235.98.

2-bromo-6-hydroxy-4-methylbenzaldehyde (42b)

(86%) ¹H NMR (400 MHz, CDCl₃) δ 10.80 (s, 1H), 9.72 (s, 1H), 7.61 (s, 1H), 6.84 (s, 1H), 2.35 (s, 4H). LC-MS (ES) for $C_8H_7BrO_2$ [M+1]⁺ 215.83.

Step 3

A solution of BBr₃ (2.5 equiv, 1.0M in DCM) was added dropwise to a solution of the corresponding benzaldehyde intermediate (1.0 equiv) in DCM (5.0 mL per mmol bezaldehyde intermediate) under N₂ at −78° C. The reaction mixture was stirred for an additional 3 h at 0° C. After this period, the solution was quenched with ice water, and the organic layer was washed with water. The organic solvent was concentrated by rotary evaporation and purified by column chromatography to give 43a-b.

2-bromo-4-chloro-6-hydroxybenzaldehyde (43a)

(73%) ¹H NMR (400 MHz, CDCl₃) 12.05 (s, 1H), 10.19 (d, J=0.5 Hz, 1H), 7.11 (d, J=1.9 Hz, 1H), 6.91 (dd, J=1.9, 0.6 Hz, 2H). LC-MS (ES) for $C_7H_4BrClO_2$ [M+1]⁺ 235.98.

2-bromo-6-hydroxy-4-methylbenzaldehyde (43b)

(88%) $^1$H NMR (400 MHz, CDCl$_3$) δ 10.80 (s, 1H), 9.72 (s, 1H), 7.61 (s, 1H), 6.84 (s, 1H), 2.35 (s, 4H). LC-MS (ES) for C$_8$H$_7$BrO$_2$ [M+1]$^+$ 215.83.

Step 4[8]

The mixture of the corresponding aldehyde intermediate (1.0 equiv) and CBr$_4$ (3.0 equiv) in DCM (5.0 mL per mmol aldehyde intermediate) was cooled to 0° C. After 20 min, PPh$_3$ (3.0 equiv) in DCM (5.0 mL per PPh$_3$) was added dropwise over 30 min and stirred for an additional 1 h at 0° C. After which it was allowed to warm to room temperature and stirred for an additional 2 h. The reaction was quenched by addition of saturated aqueous NH$_4$Cl solution. The phases were then separated, and the aqueous layer was extracted with DCM. The combined organic layer was concentrated by rotary evaporation and purified by column chromatography to give 44a-c.

3-bromo-2-(2,2-dibromovinyl)phenol (44a)

(62%) $^1$H NMR (400 MHz, CDCl$_3$) δ 7.19 (s, 1H), 7.09-7.03 (m, 2H), 6.83 (d, J=1.2 Hz, 1H), 5.04 (s, 1H). LC-MS (ES) for C$_8$H$_5$Br$_3$O [M+1]$^+$ 357.27

3-bromo-5-chloro-2-(2,2-dibromovinyl)phenol (44b)

(43%) $^1$H NMR (400 MHz, CDCl$_3$) δ 7.16 (s, 1H), 7.14 (d, J=1.9 Hz, 1H), 6.86 (d, J=1.9 Hz, 1H), 5.15 (s, 1H). LC-MS (ES) for C$_8$H$_4$Br$_3$ClO [M+1]$^+$ 392.00.

3-bromo-2-(2,2-dibromovinyl)-5-methylphenol (44c)

(46%) $^1$H NMR (400 MHz, CDCl$_3$) δ 7.63 (s, 1H), 7.39 (s, 1H), 6.66 (s, 1H), 4.89 (s, 1H), 2.26 (s, 3H). LC-MS (ES) for C$_9$H$_7$Br$_3$O [M+1]$^+$ 371.46.

Step 5[8]

K$_3$PO$_4$ (2.0 equiv) and CuI (0.1 equiv) were added to a solution of the corresponding gem-dibromoolefin (1.0 equiv) in THF (3.0 mL per mmol of gem-dibromoolefin intermediate). The flask was flushed with nitrogen for 5 min and the vial sealed and placed in a pre-heated oil bath at 80° C. The vial was stirred for 4 h, after which it was allowed to cool to room temperature. The contents were filtered over a pad of silica gel, washing with ethyl acetate. The resulting solution was concentrated by rotary evaporation and purified by column chromatography to give 45a-c.

2,4-dibromobenzofuran (45a) (85%)

$^1$H NMR (400 MHz, CDCl$_3$) δ 7.35-7.28 (m, 2H), 7.06 (t, J=8.1 Hz, 1H), 6.72 (d, J=0.9 Hz, 1H). LC-MS (ES) for C$_8$H$_4$Br$_2$O [M+1]$^+$ 276.71.

2,4-dibromo-6-chlorobenzofuran (45b)

(90%) $^1$H NMR (400 MHz, CDCl$_3$) δ 7.33-7.28 (m, 2H), 6.69 (s, 1H). LC-MS (ES) for C$_8$H$_3$Br$_2$ClO [M+1]$^+$ 311.12.

2,4-dibromo-6-methylbenzofuran (45c)

(85%) $^1$H NMR (400 MHz, CDCl$_3$) δ 7.71 (s, 1H), 7.36 (s, 1H), 6.66 (d, J=0.9 Hz, 1H), 2.50 (s, 3H). LC-MS (ES) for C$_9$H$_6$Br$_2$O [M+1]$^+$ 290.64.

Step 6[9]

Sodium cyanide (1.5 equiv) was added to a solution of the corresponding dibromobenzofuran intermediate (1.0 equiv) in dry DMSO (3.0 mL per mmol of Benzofuran intermediate) under N$_2$ at 100° C. for 24 h, quenched with saturated NH$_4$Cl solution and diluted with ethyl acetate. The organic layer was separated and washed with water, dried by rotary evaporation, and purified by column chromatography to give 46a-c.

4-bromobenzofuran-2-carbonitrile (46a)

(35%) $^1$H NMR (400 MHz, CDCl$_3$) δ 7.48-7.41 (m, 3H), 7.32 (dd, J=8.4, 7.7 Hz, 1H). LC-MS (ES) for C$_9$H$_4$BrNO [M+1]$^+$ 222.90.

4-bromo-6-chlorobenzofuran-2-carbonitrile (46b)

(29%) $^1$H NMR (400 MHz, CDCl$_3$) δ 7.54 (s, 1H), 7.39 (d, J=0.9 Hz, 1H), 7.28 (d, J=1.8 Hz, 1H). LC-MS (ES) for C$_9$H$_3$BrClNO [M+1]$^+$ 257.31.

4-bromo-6-methylbenzofuran-2-carbonitrile (46c)

(38%) $^1$H NMR (400 MHz, CDCl$_3$) δ 7.80 (s, 1H), 7.38 (s, 1H), 7.30 (d, J=0.9 Hz, 1H), 2.47 (s, 3H). LC-MS (ES) for C$_{10}$H$_6$BrNO [M+1]$^+$ 236.88.

Step 7

A mixture of the corresponding benzofuran intermediate (1.0 equiv), the corresponding catechol (2.5 equiv), Cs$_2$CO$_3$ (2.2 equiv), CuI (0.2 equiv), N,N-dimethyl glycine hydrochloride (0.4 equiv) in dioxane (5.0 mL per mmol benzofuran intermediate) in a sealed tube was heated to 90° C. under N$_2$ atmosphere for 18 h. The cooled mixture was partitioned between ethyl acetate and water. The organic layer was separated, and the aqueous layer was extracted with ethyl acetate. The combined organic layers were washed with brine, dried over Na$_2$SO$_4$, concentrated by rotary evaporation, and purified by column chromatography to give 47a-e and 47g-h.

4-(2-methoxyphenoxy)benzofuran-2-carbonitrile (47a)

(53%) $^1$H NMR (400 MHz, CDCl$_3$) δ 7.37 (d, J=0.9 Hz, 1H), 7.27 (t, J=8.2 Hz, 1H), 7.18-7.12 (m, 2H), 6.99 (td, J=7.9, 1.5 Hz, 2H), 6.91 (td, J=7.7, 1.5 Hz, 1H), 6.53 (dd, J=8.0, 0.6 Hz, 1H), 3.73 (s, 3H). LC-MS (ES) for C$_{16}$H$_{11}$NO$_3$ [M+1]$^+$ 266.08.

4-(2-methoxyphenoxy)-6-methylbenzofuran-2-carbonitrile (47b)

(71%) $^1$H NMR (400 MHz, CDCl$_3$) δ 7.31 (s, 1H), 7.23 (d, J=0.9 Hz, 1H), 7.05-7.01 (m, 1H), 6.75 (dd, 8.1, 1.4 Hz, 1H), 6.66 (s, 1H) 6.64-6.59 (m, 2H), 3.69 (s, 3H), 2.39 (s, 3H). LC-MS (ES) for C$_{17}$H$_{13}$NO$_3$ [M+1]$^+$ 280.07.

6-chloro-4-(2-methoxyphenoxy)benzofuran-2-carbonitrile (47c)

(59%) $^1$H NMR (400 MHz, CDCl$_3$) δ 7.52 (d, J=1.5 Hz, 1H), 7.36 (d, J=0.9 Hz, 1H), 7.24-7.13 (m, 2H), 7.06-6.95 (m, 2H), 6.45 (d, J=1.5 Hz, 1H), 3.72 (s, 3H). LC-MS (ES) for C$_{16}$H$_{10}$ClNO$_3$ [M+1]$^+$300.52.

4-(4-fluoro-2-methoxyphenoxy)benzofuran-2-carbonitrile (47d)

(67%) $^1$H NMR (400 MHz, CDCl$_3$) δ 7.52 (d, J=0.9 Hz, 1H), 7.37 (t, J=8.2 Hz, 1H), 7.33 (s, 1H), 7.30-7.27 (m, 2H), 7.02 (dd, J=8.5, 2.4 Hz, 1H), 6.64 (dd, J=8.0, 0.6 Hz, 1H), 3.77 (s, 3H). LC-MS (ES) for $C_{16}H_{10}FNO_3$ [M+1]$^+$ 284.10.

4-(4-fluoro-2-methoxyphenoxy)-6-methylbenzofuran-2-carbonitrile (47e)

(34%) $^1$H NMR (400 MHz, CDCl$_3$) δ 7.33 (s, 1H), 7.20 (d, J=0.8 Hz, 1H), 6.81-6.74 (m, 2H), 6.69 (dd, J=10.1, 2.8 Hz, 1H), 6.56 (ddd, J=8.7, 7.9, 2.9 Hz, 1H), 3.74 (s, 3H), 2.40 (s, 3H). LC-MS (ES) for $C_{17}H_{12}FNO_3$ [M+1]$^+$ 297.74.

4-(4-chloro-2-methoxyphenoxy)-2-methylbenzofuran (47g)

(48%) $^1$H NMR (400 MHz, CDCl$_3$) δ 7.36 (d, J=8.4 Hz, 1H), 7.20-7.04 (m, 1H), 6.99 (dd, J=5.2, 2.2 Hz, 1H), 6.91-6.77 (m, 2H), 6.63 (dd, J=7.9, 0.8 Hz, 1H), 6.39-6.18 (m, 1H), 3.85 (s, 3H), 2.42 (s, 3H). LC-MS (ES) for $C_{16}H_{13}ClO_3$ [M+1]$^+$ 289.21.

4-(4-chloro-2-methoxyphenoxy)benzofuran-2-carbonitrile (47h)

(52%) $^1$H NMR (400 MHz, CDCl$_3$) δ 7.43 (d, J=0.9 Hz, 1H), 7.26 (t, J=8.2 Hz, 1H), 7.14 (dt, J=8.4, 0.8 Hz, 1H), 6.98 (dd, J=8.8, 5.7 Hz, 1H), 6.71 (dd, J=10.1, 2.8 Hz, 1H), 6.62 (ddd, J=8.8, 7.8, 2.9 Hz, 1H), 6.44 (dd, J=8.0, 0.6 Hz, 1H), 3.70 (s, 3H). LC-MS (ES) for $C_{16}H_{10}ClNO_3$ [M+1]$^+$ 390.12.

Step 8

A solution of BBr$_3$ (2.5 equiv, 1.0M in DCM) was added dropwise to a solution of the corresponding diether intermediate (1.0 equiv) in DCM (3.0 mL per mmol diether intermediate) under N$_2$ at −78° C. The reaction mixture was stirred for an additional 3 h or overnight at 0° C. After this period, the solution was quenched with ice water, the organic layer washed with water and dried over Na$_2$SO$_4$. The organic solvent was concentrated by rotary evaporation and purified by column chromatography to give 48a-h.

4-(2-hydroxyphenoxyl)benzofuran-2-carbonitrile (48a)

(87%) $^1$H NMR (400 MHz, CDCl$_3$) δ 7.39-7.30 (m, 2H), 7.24 (dt, J=8.4, 0.7 Hz, 1H), 7.11-7.00 (m, 2H), 6.88-6.79 (m, 2H), 6.73 (dd, J=8.0, 0.6 Hz, 1H), 5.43 (s, 1H). LC-MS (ES) for $C_{15}H_9NO_3$ [M+1]$^+$ 252.02.

4-(2-hydroxyphenoxy)-6-methylbenzofuran-2-carbonitrile (48b)

(61%) $^1$H NMR (400 MHz, CDCl$_3$) δ 7.39 (s, 1H), 7.26 (d, J=0.9 Hz, 1H), 7.05 (s, 1H), 7.02-6.94 (m, 2H), 6.75 (ddd, J=8.1, 7.1, 2.0 Hz, 1H), 6.60 (dd, J=8.1, 1.3 Hz, 1H), 5.50 (s, 1H), 2.36 (s, 3H). LC-MS (ES) for $C_{16}H_{11}NO_3$ [M+1]$^+$ 265.82.

6-chloro-4-(2-hydroxyphenoxyl)benzofuran-2-carbonitrile (48c)

(60%) $^1$H NMR (400 MHz, CDCl$_3$) δ 7.30 (d, J=0.9 Hz, 1H), 7.27-7.25 (m, 1H), 7.15-7.09 (m, 1H), 7.04 (dd, J=8.1, 1.5 Hz, 1H), 6.91 (td, J=8.4, 1.7 Hz, 2H), 6.69 (d, J=1.5 Hz, 1H), 5.25 (s, 1H). LC-MS (ES) for $C_{15}H_8ClNO_3$ [M+1]$^+$ 286.29.

4-(4-fluoro-2-hydroxyphenoxy)benzofuran-2-carbonitrile (48d)

(69%) $^1$H NMR (400 MHz, CDCl$_3$) δ 7.81 (d, J=1.0 Hz, 1H), 7.39 (t, J=8.0 Hz, 1H), 7.34 (s, 1H), 7.02-6.94 (m, 3H), 6.66 (dd, J=8.0, 0.8 Hz, 1H), 5.33 (s, 1H). LC-MS (ES) for $C_{15}H_8FNO_3$ [M+1]$^+$ 270.08.

4-(4-fluoro-2-hydroxyphenoxy)-6-methylbenzofuran-2-carbonitrile (48e)

(72%) $^1$H NMR (400 MHz, CDCl$_3$) δ 7.37 (s, 1H), 7.24 (d, J=0.9 Hz, 1H), 6.97 (s, 1H), 6.74 (dd, J=9.3, 2.9 Hz, 1H), 6.59 (dd, J=8.9, 5.3 Hz, 1H), 6.47 (ddd, J=8.9, 8.1, 3.0 Hz, 1H), 5.60 (s, 1H), 2.35 (s, 3H). LC-MS (ES) for $C_{16}H_{10}FNO_3$ [M+1]$^+$ 283.96.

2-(benzofuran-4-yloxy)-5-chlorophenol (48f)

(43%) $^1$H NMR (500 MHz, CDCl$_3$) δ 7.58 (d, J=2.0 Hz, 1H), 7.33 (d, J=8.5 Hz, 1H), 7.23 (t, J=8.0 Hz, 1H), 7.09 (s, 1H), 6.79-6.78 (m, 2H), 6.66 (s, 1H), 5.74 (s, 1H). GC-MS (ES) for $C_{14}H_9ClO_3$ [M]$^+$=260.

5-chloro-2-((2-methylbenzofuran-4-yl)oxy)phenol (48g)

(82%) $^1$H NMR (400 MHz, CDCl$_3$) δ 7.31 (s, 1H), 7.15 (t, J=8.1 Hz, 1H), 7.06 (dd, J=8.1, 2.3 Hz, 1H), 6.85-6.64 (m, 3H), 6.21 (d, J=0.8 Hz, 1H), 5.76 (d, J=13.8 Hz, 1H), 2.55-2.29 (m, 3H). LC-MS (ES) for $C_{15}H_{11}ClO_3$ [M+1]$^+$ 275.11.

4-(4-chloro-2-hydroxyphenoxy)benzofuran-2-carbonitrile (48h)

(64%) $^1$H NMR (400 MHz, CDCl$_3$) δ 7.37-7.34 (m, 2H), 7.27 (dt, J=8.5, 0.8 Hz, 1H), 7.05 (dd, J=2.1, 0.5 Hz, 1H), 6.80-6.78 (m, 2H), 6.73 (dd, J=8.0, 0.6 Hz, 1H), 5.44 (s, 1H). LC-MS (ES) for $C_{15}H_{18}ClNO_3$ [M+1]$^+$ 285.73.

Step 9

17 (1.5 equiv) and K$_2$CO$_3$ (2.0 equiv) were added to a solution of the corresponding catechol aryl ether intermediate (1.0 equiv) in DMF (1.0 mL per mmol aryl ether intermediate) and the mixture was stirred for 3 h at 60° C. to complete the reaction. The reaction mixture was poured into brine and extracted with ethyl acetate. The organic layer was sequentially washed with brine, dried over Na$_2$SO$_4$, and concentrated by rotary evaporation. The crude product was dissolved in DCM (1.0 mL per mmol catechol diether intermediate) and aq. NH$_4$OH (30%) (0.5 mL per mmol catechol aryl ether intermediate) were added. The reaction mixture was stirred at room temperature for 16 h. After completion, the reaction mixture was concentrated by rotary evaporation and purified by column chromatography to give 12a-h.

4-(2-(2-(2,4-dioxo-3,4-dihydropyrimidin-1(2H)-yl)ethoxy)phenoxy)benzofuran-2-carbonitrile (12a)

(41%) $^1$H NMR (400 MHz, Acetone-d$_6$) δ 9.80 (s, 1H), 7.87 (d, J=0.9 Hz, 1H), 7.44 (t, J=8.2 Hz, 1H), 7.35-7.21 (m, 4H), 7.11 (ddd, J=7.9, 7.3, 1.7 Hz, 1H), 6.93 (d, J=7.9 Hz, 1H), 6.51 (dd, J=8.0, 0.5 Hz, 1H), 4.99 (d, J=7.9 Hz, 1H), 4.31-4.23 (m, 2H), 3.99-3.93 (m, 2H). $^{13}$C NMR (101 MHz, CDCl$_3$) δ 163.30, 160.57, 156.62, 152.69, 150.69, 150.01, 145.27, 143.78, 127.22, 126.14, 122.60, 122.52, 118.49, 114.19, 108.06, 106.09, 104.81, 101.36, 99.99, 66.69, 48.21. HR-MS (ES) calcd for $C_{21}H_{15}N_3O_5$ [M+1]$^+$ 390.1090. found 390.1093.

4-(2-(2-(2,4-dioxo-3,4-dihydropyrimidin-1(2H)-yl)ethoxy)phenoxy)-6-methylbenzofuran-2-carbonitrile (12b)

(47%) $^1$H NMR (400 MHz, CDCl$_3$) δ 8.11 (s, 1H), 7.37 (s, 1H), 7.18 (d, J=0.8 Hz, 1H), 7.11-7.03 (m, 1H), 6.96-6.87 (m, 3H), 6.82 (dd, J=8.3, 1.6 Hz, 1H), 6.72 (s, 1H), 5.22 (dd, J=7.9, 2.1 Hz, 1H), 4.17 (t, J=4.6 Hz, 2H), 3.95 (t, J=4.6 Hz, 2H), 2.38 (s, 3H). $^{13}$C NMR (101 MHz, CDCl$_3$) δ 162.81, 153.42, 151.79, 150.46, 149.38, 145.37, 130.51, 127.55, 125.09, 124.02, 122.76, 120.75, 118.14, 114.82, 113.66, 111.79, 107.64, 106.33, 101.35, 66.92, 48.31, 17.37. HR-MS (ES) calcd for $C_{22}H_{17}N_3O_5$ [M+1]$^+$ 404.1168. found 404.1163.

6-chloro-4-(2-(2-(2,4-dioxo-3,4-dihydropyrimidin-1(2H)-yl)ethoxy)phenoxy)benzofuran-2-carbonitrile (12c)

(53%) $^1$H NMR (400 MHz, CDCl$_3$) δ 7.81 (s, 1H), 7.33 (d, J=0.9 Hz, 1H), 7.21 (d, J=1.5 Hz, 1H), 7.10-6.94 (m, 4H), 6.60 (d, J=7.9 Hz, 1H), 6.36 (d, J=1.5 Hz, 1H), 5.05 (dd, J=7.9, 2.4 Hz, 1H), 4.16 (t, J=4.7 Hz, 2H), 3.89 (t, J=4.7 Hz, 2H). $^{13}$C NMR (126 MHz, CDCl$_3$) δ 162.44, 153.86, 149.72, 149.39, 145.20, 144.95, 134.16, 127.27, 127.15, 126.43, 125.21, 119.45, 117.12, 114.71, 114.44, 111.72, 110.79, 109.79, 100.56, 66.79, 47.15. HR-MS (ES) calcd for $C_{21}H_{14}ClN_3O_5$ [M+1]$^+$ 424.0700. found 424.0682.

4-(2-(2-(2,4-dioxo-3,4-dihydropyrimidin-1(2H)-yl)ethoxy)-4-fluorophenoxy)benzofuran-2-carbonitrile (12d)

(52%) $^1$H NMR (500 MHz, Acetone-d$_6$) δ 9.81 (br, 1H), 7.92 (d, J=0.9 Hz, 1H), 7.46 (t, J=8.2 Hz, 1H), 7.37 (s, 1H), 7.38-7.32 (m, 2H), 7.13 (dd, J=8.5, 2.4 Hz, 1H), 6.94 (d, J=7.9 Hz, 1H), 6.60-6.56 (m, 1H), 5.01 (d, J=7.9 Hz, 1H), 4.34 (t, J=4.0 Hz, 2H), 3.99 (t, J=4.0 Hz, 2H). $^{13}$C NMR (126 MHz, Acetone-d$_6$) δ 163.07, 157.41, 152.91, 151.70, 150.99, 145.48, 142.50, 131.39, 130.00, 126.90, 124.12, 122.17, 116.82, 116.62, 115.50, 110.56, 108.63, 106.46, 100.70, 67.26, 47.78. HR-MS (ES) calcd for $C_{21}H_{14}FN_3O_5$ [M+1]$^+$ 408.0996. found 408.0977.

4-(2-(2-(2,4-dioxo-3,4-dihydropyrimidin-1(2H)-yl)ethoxy)-4-fluorophenoxy)-6-methylbenzofuran-2-carbonitrile (12e)

(63%) $^1$H NMR (400 MHz, CDCl$_3$) δ 7.95 (s, 1H), 7.37 (s, 1H), 7.17 (d, J=0.8 Hz, 1H), 6.84 (dd, J=8.7, 5.6 Hz, 1H), 6.78 (d, J=7.9 Hz, 1H), 6.70-6.61 (m, 3H), 5.16 (dd, J=7.9, 2.4 Hz, 1H), 4.13 (t, J=4.7 Hz, 2H), 3.92 (t, J=4.7 Hz, 2H), 2.39 (s, 3H). $^{13}$C NMR (126 MHz, CDCl$_3$) δ 168.24, 161.84, 152.75, 150.56, 149.43, 149.23, 143.99, 131.00, 127.60, 126.32, 124.60, 122.91, 121.03, 117.04, 112.66, 110.74, 107.61, 105.32, 100.43, 65.80, 47.12, 16.35. HR-MS (ES) calcd for $C_{22}H_{16}FN_3O_5$ [M+1]$^+$ 422.1074. found 422.1066.

1-(2-(2-(benzofuran-4-yloxy)-5-chlorophenoxy)ethyl)pyrimidine-2,4(1H,3H)-dione (12f)

(10%) $^1$H NMR (500 MHz, CD$_3$OD) δ 7.66 (d, J=2.0 Hz, 1H), 7.14 (d, J=2.5 Hz, 1H), 7.13 (s, 1H), 7.06 (t, J=8.5 Hz, 1H), 7.02 (d, J=8.5 Hz, 1H), 6.97 (dd, J=8.5, 2.5 Hz, 1H), 6.76 (d, J=8.0 Hz, 1H), 6.70 (dd, J=2.3, 0.5 Hz, 1H), 6.34 (d, J=8.0 Hz, 1H), 4.88 (d, J=8.0 Hz, 1H), 4.14 (t, J=5.0 Hz, 2H), 3.87 (t, J=5.0 Hz, 2H). $^{13}$C NMR (125 MHz, CD$_3$OD) δ 158.12, 153.53, 152.8, 152.44, 147.41, 145.89, 131.78, 125.94, 124.38, 123.05, 116.21, 108.49, 107.07, 104.59, 101.41, 67.98. HR-MS (ES) calcd for $C_{20}H_{15}ClN_2O_5$ [M+1]$^+$ 399.0669. found 399.0630.

1-(2-(5-chloro-2-((2-methylbenzofuran-4-yl)oxy)phenoxy)ethyl)pyrimidine-2,4(1H,3H)-dione (12g)

(78%) $^1$H NMR (400 MHz, Acetone-d$_6$) δ 9.90 (m, 1H), 7.63-7.39 (m, 1H), 7.27 (dd, J=4.3, 2.3 Hz, 1H), 7.22-7.02 (m, 3H), 7.02-6.85 (m, 2H), 6.63-6.32 (m, 2H), 5.06 (d, J=8.1 Hz, 1H), 4.32 (dd, J=8.7, 4.7 Hz, 2H), 4.16-3.89 (m, 2H), 2.45 (2, 3H). $^{13}$C NMR (126 MHz, CDCl$_3$) δ 163.40, 149.95, 145.27, 140.79, 126.13, 122.71, 122.68, 122.25, 119.17, 114.54, 111.33, 101.30, 97.12, 77.29, 77.03, 76.78, 66.70, 48.27, 21.34. HR-MS (ES) calcd for $C_{21}H_{17}ClN_2O_5$ [M+1]$^+$ 413.0826. found 413.0808.

4-(4-chloro-2-(2-(2,4-dioxo-3,4-dihydropyrimidin-1(2H)-yl)ethoxy)phenoxy)benzofuran-2-carbonitrile (12h)

(47%) $^1$H NMR (500 MHz, Acetone-d$_6$) δ 9.80 (br, 1H), 7.92 (s, 1H), 7.44 (t, J=8.2 Hz, 1H), 7.36-7.32 (m, 1H), 7.29 (dd, J=8.8, 5.8 Hz, 1H), 7.14 (dd, J=10.4, 2.9 Hz, 1H), 6.91 (d, J=7.9 Hz, 1H), 6.88 (ddd, J=8.8, 8.2, 2.9 Hz, 1H), 6.52 (d, J=8.0 Hz, 1H), 4.98 (d, J=7.9 Hz, 1H), 4.32 (t, J=4.0 Hz, 2H), 3.99 (t, J=4.0 Hz, 2H). $^{13}$C NMR (126 MHz, Acetone-d$_6$) δ 157.42, 153.28, 145.45, 129.99, 128.05, 126.81, 126.78, 124.07, 123.69, 116.65, 115.67, 108.16, 107.42, 106.19, 104.96, 103.09, 101.14, 100.67, 99.94, 67.17, 47.76. HR-MS (ES) calcd for $C_{21}H_{14}ClN_3O_5$ [M+1]$^+$ 424.0700. found 424.0696.

Example 9

Synthesis of Compounds 46g and 47f

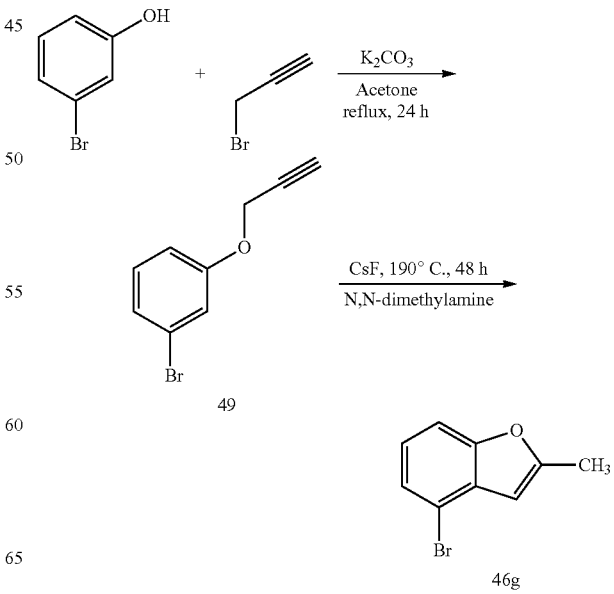

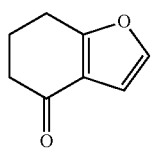

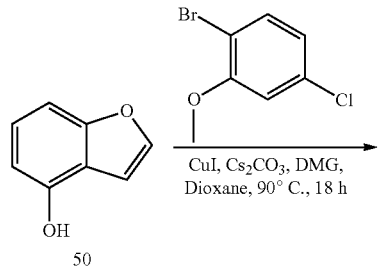

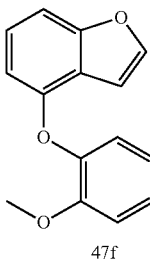

Step A1

To a solution of 3-bromophenol (23 mmol), propargyl bromide (27 mmol) in acetone (40 mL), K₂CO₃ (27 mmol) was added and the mixture was stirred at reflux for 24 h. After this period, the mixture was allowed to cool to room temperature, the solid was filtered, the acetone was concentrated by rotary evaporation, and purified by column chromatography to give 49.

Synthesis of 1-bromo-3-(prop-2-yn-1-yloxy)benzene (49)

(92%) $^1$H NMR (500 MHz, CDCl$_3$) δ 3.40 (t, J=5 Hz, 1H), 4.80 (s, 2H), 6.89 (d, J=8.0 Hz, 1H), 7.16-7.29 (m, 2H), 7.33 (s, 1H). LC-MS (ES) for C$_9$H$_7$BrO [M+1]$^+$ 212.93.

Step A2

To a solution of 49 (21 mmol) in N, N-diethylaniline (30 mL), cesium fluoride (11 mmol) was added and the mixture was heated at 190° C. for 24 h. After cooling, the suspension was diluted with ethyl acetate (100 mL) and washed with dil HCl (3×50 mL). The combined organic layer was washed with brine, dried over anhydrous Na$_2$SO$_4$ and concentrated by rotary evaporation and purified column chromatography to give 4-bromo-2-methylbenzofuran (46g, 87%) and 6-bromo-2-methylbenzofuran (13%). The resulting mixture was purified by reverse phase HPLC using 10:1 acetonitrile: water with 0.1% TFA (B) for 22 min followed by 3 min at 100% B, to give compound 46g (26%).

4-bromo-2-methylbenzofuran (46g)

$^1$H NMR (500 MHz, CDCl$_3$) δ 2.30 (s, 3H), 6.80 (s, 1H), 7.22 (d, J=8.2 Hz, 1H), 7.33 (dd, J=8.2, 1.2 Hz, 1H), 7.44 (d, J=8.2 Hz, 1H). LC-MS (ES) for C$_9$H$_7$BrO [M+1]$^+$ 212.33.

Step B1

To a solution of 6,7-Dihydro-4(5H)-benzofuranone (11 mmol), 1-dodecene (14 mmol), Pd/C (1.0 g) in dry decalin (20 mL) was stirred at reflux under N$_2$ atmosphere for 24 h. The reaction was cooled down, quenched with EtOH (15 mL), filtered, and concentrated in vacuo. The product was purified by column chromatography to give 50.

benzofuran-4-ol (50)

(32%) $^1$H NMR (400 MHz, CDCl$_3$) δ 7.54 (d, J=2.4 Hz, 1H), 7.13 (d, J=8.4 Hz, 1H), 7.12 (s, 1H), 6.86 (dd, J=2.4, 0.8 Hz, 1H), 6.64 (dd, J=6.8, 1.6 Hz, 1H), 5.64 (s, 1H). GC-MS (ES) for C$_8$H$_6$O$_2$ [M]$^+$ 134.

Step B2

To a solution of benzofuran-4-ol (2.0 mmol), 2-bromo-5-chloroanisole (2.6 mmol), Cs$_2$CO$_3$ (3.0 mmol), CuI (0.2 mmol) and N,N-dimethylglycine hydrochloride (0.6 mmol) in dry dioxane were stirred at 90-100° C. under N$_2$ atmosphere for 24 h. The reaction was cooled down, quenched with brine, and extracted with ethyl acetate (3×10 mL). The combined organic layer was dried over anhydrous Na$_2$SO$_4$ and concentrated in vacuo. The product was purified by column chromatography to give 47f.

4-(4-chloro-2-methoxyphenoxy)Benzofuran (47f)

(33%) $^1$H NMR (400 MHz, CDCl$_3$) δ 7.54 (d, J=2.0 Hz, 1H), 7.24 (s, 1H), 7.17 (t, J=8.0 Hz, 1H), 7.08 (t, J=1.2 Hz, 1H), 6.89-6.88 (m, 2H), 6.72-6.71 (m, 1H), 6.62 (d, J=7.6 Hz, 1H), 3.84 (s, 3H). GC-MS (ES) for C$_{15}$H$_{11}$ClO$_3$ [M]$^+$=274.

Example 10

7. Synthesis of Compound 13a

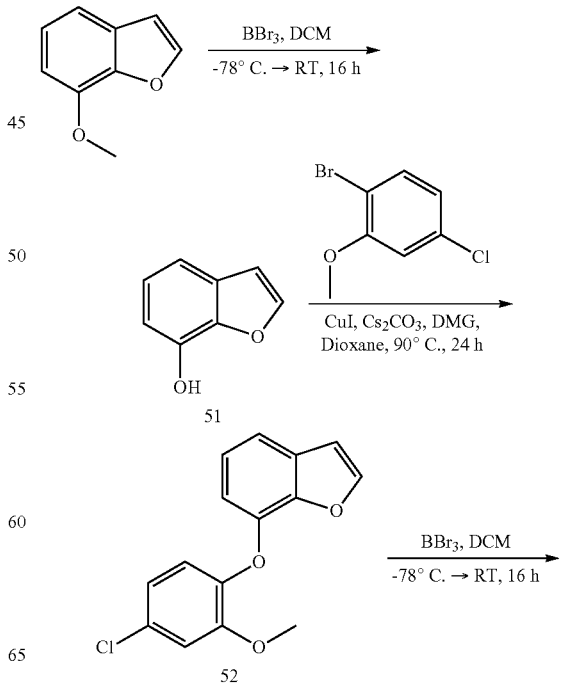

83

-continued

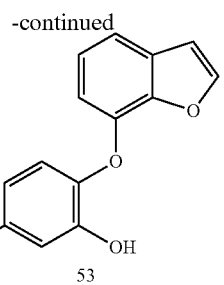

i) K₂CO₃, DMF, 60° C., 2 h
ii) NH₄OH, RT, 25 h

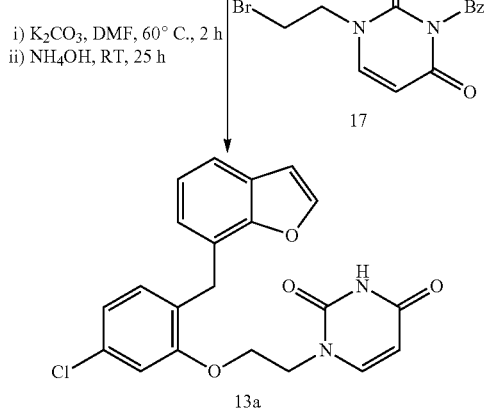

Step 1

To a stirred solution of 7-methoxybenzofuran (3.3 mmol)) in dry DCM (5.0 mL) at −78° C. under N₂ atmosphere was added BBr₃ (3.0 mmol) (1.0M solution in DCM) and then the reaction was allowed to stir overnight at room temperature. The crude reaction was quenched with ice water and extracted with DCM (3×5.0 mL). The combined organic layer was dried over anhydrous Na₂SO₄ and concentrated in vacuo. The product was purified by column chromatography to give 51.

benzofuran-7-ol (51)

(42%) $^1$H NMR (500 MHz, CDCl₃) δ 7.60 (d, J=2.0 Hz, 1H), 7.16 (d, J=7 Hz, 1H), 7.10 (t, J=7.5 Hz, 1H), 6.83 (d, J=7.5 Hz, 1H), 6.77 (d, J=2.0 Hz, 1H), 5.43 (s, 1H). GC-MS (ES) for C₈H₆O₂ [M]⁺ 134.

Step 2

Synthesis of
7-(4-chloro-2-methoxyphenoxy)Benzofuran (52)

Following step A2 in the synthetic scheme 1.2 from 51 to give 52 (20%). $^1$H NMR (500 MHz, CDCl₃) δ 7.62 (d, J=2.0 Hz, 1H), 7.32 (dd, J=8.0, 1.0 Hz, 1H), 7.12 (t, J=8.0 Hz, 1H), 7.00 (d, J=2.0 Hz, 1H), 6.88-6.85 (m, 2H), 6.80 (d, J=2.0 Hz, 1H), 6.74 (d, J=8.0 Hz, 1H), 3.85 (s, 3H). GC-MS (ES) for C₁₅H₁₁ClO₃ [M]⁺=274.

Step 3

To a stirred solution of 7-(4-chloro-2-methoxyphenoxy) benzofuran (52, 0.2 mmol) in dry DCM (5.0 mL) at −78° C. under N₂ atmosphere was added BBr₃ (3.0 mmol, 1.0M solution in DCM) and then the reaction was allowed to stir overnight at room temperature. The crude reaction was quenched with ice water and extracted with DCM (3×5.0 mL). The combined organic layer was dried over anhydrous Na₂SO₄ and concentrated in vacuo. The product was purified by column chromatography to give 53.

84

2-(benzofuran-7-yloxy)-5-chlorophenol (53)

(100%). $^1$H NMR (500 MHz, CDCl₃) δ 7.62 (d, J=2.0 Hz, 1H), 7.40 (d, J=8.0 Hz, 1H), 7.18 (t, J=8.0 Hz, 1H), 7.08 (s, 1H), 6.91 (d, J=8.0 Hz, 1H), 6.82 (d, J=2.0 Hz, 1H), 6.78-6.77 (m, 2H), 5.86 (s, 1H). GC-MS (ES) for C₁₄H₉ClO₃ [M]⁺ =260.

Step 4

A solution of 2-(benzofuran-7-yloxy)-5-chlorophenol (53, 1.0 mmol) and K₂CO₃ (1.1 mmol) in dry DMF (2.0 mL) were stirred at room temperature for 1 h. Then, a solution of 1-(2-bromoethyl)pyrimidine-2,4(1H,3H)-dione (17, 1.1 mol) in dry DMF (2.0 mL) was added and the reaction mixture was stirred at 60° C. for 2 h and then at room temperature for overnight. The crude reaction was quenched with brine and extracted with ethyl acetate (3×10 mL). The combined organic layer was dried over anhydrous Na₂SO₄ and concentrated in vacuo. The crude product was dissolved in dry MeOH (3.0 mL) and then 3.0 mL of NH₄OH was added. The crude reaction was stirred at room temperature until completion. Then, the crude reaction was concentrated in vacuo and the product purified by column chromatography to give 13a. Further purification was performed by HPLC (5-100% of water with 0.1% trifluoroacetic acid (TFA) (A) and 10:1 acetonitrile:water with 0.1% TFA(B)).

1-(2-(2-(benzofuran-7-yloxy)-5-chlorophenoxy)
ethyl)pyrimidine-2,4(1H,3H)-dione (13a)

(10%) $^1$H NMR (800 MHz, CD₃OD) δ 7.75 (d, J=2.4 Hz, 1H), 7.27 (dd, J=8.0, 0.8 Hz, 1H), 7.17 (d, J=2.4 Hz, 1H), 7.04 (t, J=7.2 Hz, 1H), 7.01 (d, J=8.0 Hz, 1H), 6.98 (dd, J=8.8, 2.4 Hz, 1H), 6.87-6.86 (m, 2H), 6.52 (d, J=8.0 Hz, 1H), 4.97 (d, J=7.2 Hz, 1H), 4.20 (t, J=4.8 Hz, 2H), 3.92 (t, J=4.8 Hz, 2H). $^{13}$C NMR (200 MHz, CD₃OD) δ 166.48, 152.52, 152.18, 147.98, 146.9, 144.26, 131.6, 131.5, 124.49, 123.6, 122.97, 116.73, 116.29, 111.55, 108.14, 101.39, 68.10. HR-MS (ES) calcd for C₂₀H₁₅ClN₂O₅ [M+1]⁺ 399.0785. found 399.0663.

REFERENCES FOR EXAMPLES 1-10

1. Ma, D.; Cai, Q. *Org. Lett.*, 2003, 5, 3799-3802.
2. Jacquemard, U.; Benetau, V.; Lefoix, M.; Routier, S.; Merour, J-Y.; Coudert, G. *Tetrahedron* 2004, 60, 10039-10047.
3. Bollini, M.; Domaoal, R. A.; Thakur, V. V.; Gallardo-Macias, R.; Spasov, K. A.; Anderson, K. S.; Jorgensen, W. L. *J. Med. Chem.* 2011, 54, 8582-8591.
4. PCT Int. Appl. 2008055808.
5. Zheng, C.; Lu, Y.; Zhang, J.; Chen, X.; Chai, Z.; Ma, W.; Zhao, G. *Chem. Eur. J.* 2010, 16, 5853.
6. a) Ryabova, S. Y.; Alekseeva, L. M.; Lisitsa, E. A.; Granik, V. G. *Russ. Chem. Bull., Int. Ed.* 2006, 55, 1248. b) Attanasi, O.; Palma, P.; Serra-Zanetti, F. *Synthesis* 1983, 9, 741-742.
7. Bode, M. L.; Kaye, P. T. *J. Chem. Soc. Perkin Trans.* 1 1993, 1809-1813.
8. Newman, S. G.; Aureggi, V.; Bryan, C. S.; Lautens, M. *Chem. Commun.* 2009, 5236-5238.

9. Zhou, W.; Chen, W.; Wang, L. *Org. Biomol. Chem.* 2012, 10 4172-4178.

Example 11

1. Synthesis of Compound 1c[1]

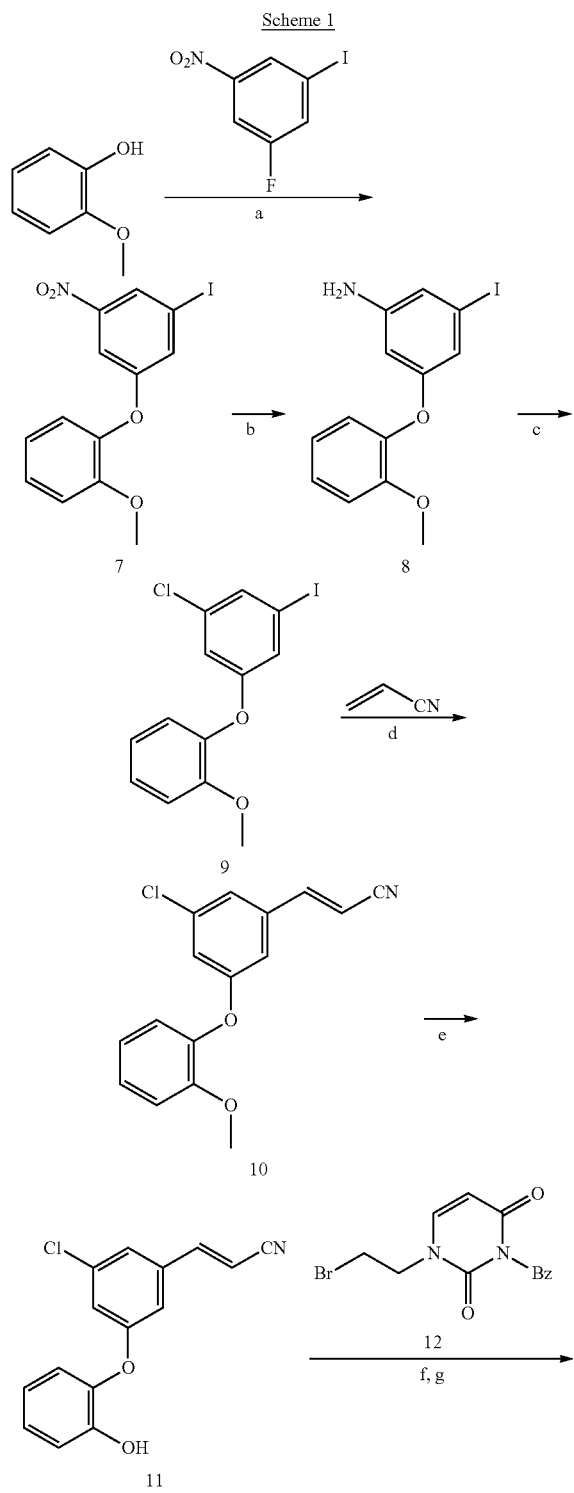

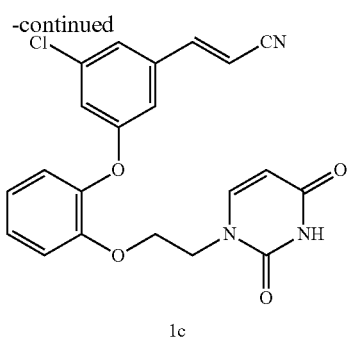

Step a

A mixture of 1-fluoro-3-iodo-5-nitrobenzene (5.0 g, 18.0 mmol), 2-methoxyphenol (2.3 g, 18.0 mmol) in dry DMSO (10.0 mL) and anhydrous $K_2CO_3$ (3.8 g, 27.5 mmol) was heated at 110° C. for 16 h. The mixture was poured into ice water and extracted with EtOAc (3×50 mL). The organic layer was sequentially washed with brine (2×75 mL), dried over anhydrous $Na_2SO_4$, concentrated by rotary evaporation, and purified by column chromatography to give 1-iodo-3-(2-methoxyphenoxy)-5-nitrobenzene (7) (4.7g, 70%). $^1$H NMR (400 MHz, $CDCl_3$) δ 8.23-8.13 (m, 1H), 7.69-7.48 (m, 2H), 7.30-7.25 (m, 1H), 7.12-6.93 (m, 3H), 3.80 (d, J=1.9 Hz, 3H).

Step b 7 (4.9 g, 13 mmol), Fe (5.9 g, 100 mmol) and a solution of $NH_4Cl$ (2.3 g in 23 mL $H_2O$, 42 mmol) were suspended in 67 mL of EtOH and heated at 75° C. for 6 h. The mixture was allowed to cool to room temperature, filtered over celite, and concentrated by rotary evaporation. The residue was partitioned between EtOAc and water; combined organic extracts were dried over anhydrous $Na_2SO_4$, concentrated by rotary evaporation, and purified by column chromatography to give 3-iodo-5-(2-methoxyphenoxy)aniline (8) (3.4 g, 77%). $^1$H NMR (600 MHz, $CDCl_3$) δ 7.18-7.13 (m, 1H), 7.00 (ddd, J=7.7, 5.7, 1.5 Hz, 2H), 6.94 (td, J=7.7, 1.4 Hz, 1H), 6.83-6.79 (m, 1H), 6.71-6.68 (m, 1H), 6.30 (t, J=2.0 Hz, 1H), 3.82 (s, 3H).

Step c 8 (3.4 g, 9.9 mmol) was suspended in concentrated HCl (17 mL) at 0° C. and stirred for 30 min. After this period, a solution of $NaNO_2$ in $H_2O$ (0.6 g in 9.2 mL, 19 mmol) was added dropwise. Then the resulting mixture was stirred for 1 h at room temperature. This solution was added over 30 min to a solution of CuCl (16.6 g, 40 mmol) in concentrated HCl (17.0 mL) at 65° C. After addition, the mixture was heated at 80° C. for 30 minutes. The mixture was allowed to cool to room temperature before addition of brine. The solution was extracted with ethyl acetate, dried over anhydrous $MgSO_4$, evaporated by rotary evaporation, and purified by column chromatography to give 1-chloro-3-iodo-5-(2-methoxyphenoxy)benzene (9) (1.5 g, 42%). $^1$H NMR (400 MHz, $CDCl_3$) δ 7.35 (t, J=1.6 Hz, 1H), 7.23-7.15 (m, 1H), 7.13 (dd, J=2.2, 1.4 Hz, 1H), 7.06-6.94 (m, 3H), 6.83 (t, J=2.0 Hz, 1H), 3.82 (d, J=4.5 Hz, 3H).

Step d

Acrylonitrile (1.6 mL, 41 mmol) was added to a mixture of 9 (1.5 g, 4.1 mmol), $Et_3N$ (1.1 mL, 13 mmol), $PdCl_2(PPh_3)_2$ (0.16 g 0.23 mmol), and dry DMF (15.0 mL) under a nitrogen atmosphere at room temperature. The mixture was heated at 140° C. for 3 h. The reaction mixture was quenched with water and extracted with EtOAc (3×50 mL). The organic layer was sequentially washed with brine (2×75 mL), dried over anhydrous $Na_2SO_4$, concentrated by rotary evaporation, and purified by column chromatography to give (Z)-3-(3-chloro-5-(2-methoxyphenoxy)phenyl)acrylonitrile (0.17 g, 16%) and (E)-3-(3-chloro-5-(2-methoxyphenoxy)phenyl)acrylonitrile (10) (0.52 g, 45%). $^1$H NMR (400 MHz, CDCl$_3$) δ 7.27 (s, 1H), 7.19-7.08 (m, 2H), 7.06-6.97 (m, 2H), 6.91 (ddt, J=15.9, 14.2, 4.6 Hz, 3H), 5.80 (dd, J=16.6, 5.2 Hz, 1H), 3.79 (s, 3H).

Step e

A solution of BBr$_3$ (9.0 mmol, 1M in CH$_2$Cl$_2$) was added dropwise to a solution of 10 (1.8 mmol) in dry CH$_2$Cl$_2$ (4.0 mL) under N$_2$ at −78° C. The reaction mixture was stirred at this temperature for 1 h. After this period, the reaction was allowed to warm to room temperature and stirred for 12 h. After reaction completion, the solution was quenched with methanol, and concentrated in vacuo. The residue was extracted with CH$_2$Cl$_2$ and washed with a solution of NaHCO$_3$. The combined organic layer was washed with brine, dried over anhydrous Na$_2$SO$_4$, concentrated by rotary evaporation, and purified by column chromatography to give (E)-3-(3-chloro-5-(2-hydroxyphenoxy)phenyl)acrylonitrile (11) (0.14 g, 51%) $^1$H NMR (400 MHz, CDCl$_3$) δ 7.29 (s, 1H), 7.21-7.10 (m, 2H), 7.11-7.01 (m, 2H), 6.92 (ddt, J=16.0, 14.5, 4.9 Hz, 3H), 5.85 (dd, J=16.6, 5.2 Hz, 1H), 5.51 (s, 1H).

Step f and g$^2$

12$^2$ (0.37 mmol) and K$_2$CO$_3$ (0.62 mmol) were added to a solution of 11 (85 mg, 0.31 mmol) in dry DMF (3.0 mL) and the mixture was stirred for 3 h at 60° C. to complete the reaction. The reaction mixture was poured into brine and extracted with ethyl acetate. The organic layer was sequentially washed with brine, dried over anhydrous Na$_2$SO$_4$, and concentration by rotary evaporation. The crude product was dissolved in DCM (2.0 mL) and NH$_4$OH (2.0 mL) were added. The reaction mixture was stirred at room temperature for 16 h. After completion, the reaction mixture was concentrated by rotary evaporation and purified by column chromatography to give 1c.

(E)-3-(3-chloro-5-(2-(2-(2,4-dioxo-3,4-dihydropyrimidin-1(2H)-yl)ethoxy)phenoxy)phenyl)acrylonitrile (1c)

(36%) $^1$H NMR (500 MHz, Acetone-d$_6$) δ 7.39 (d, J=16.7 Hz, 1H), 7.24 (s, 1H), 7.19-7.13 (m, 1H), 7.11 (d, J=1.5 Hz, 1H), 7.04 (s, 1H), 6.96 (dd, J=4.7, 3.2 Hz, 3H), 6.73 (s, 1H), 6.23 (d, J=16.7 Hz, 1H), 5.05 (d, J=7.9 Hz, 1H), 4.21-4.08 (m, 2H), 3.96-3.84 (m, 2H). $^{13}$C NMR (126 MHz, Acetone-d$_6$) δ 163.67, 151.51, 150.91, 146.29, 143.16, 128.41, 127.75, 123.89, 122.75, 120.99, 120.49, 116.66, 115.16, 113.59, 101.06, 100.68, 99.57, 97.52, 67.16, 48.58. HRMS (ESI-TOF) calcd for C$_{21}$H$_{16}$ClN$_3$O$_4$ [M+H]$^+$ 410.0865. found 410.0863.

Example 12

3. Representative Synthesis of Compounds 14a-m

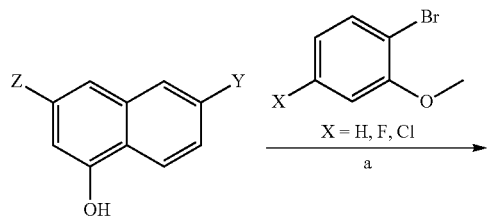

13a) Y = Z = H
13b) Y = CH$_3$, Z = H
13c) Y = Cl, Z = H
24b) Y = CN, Z = Cl

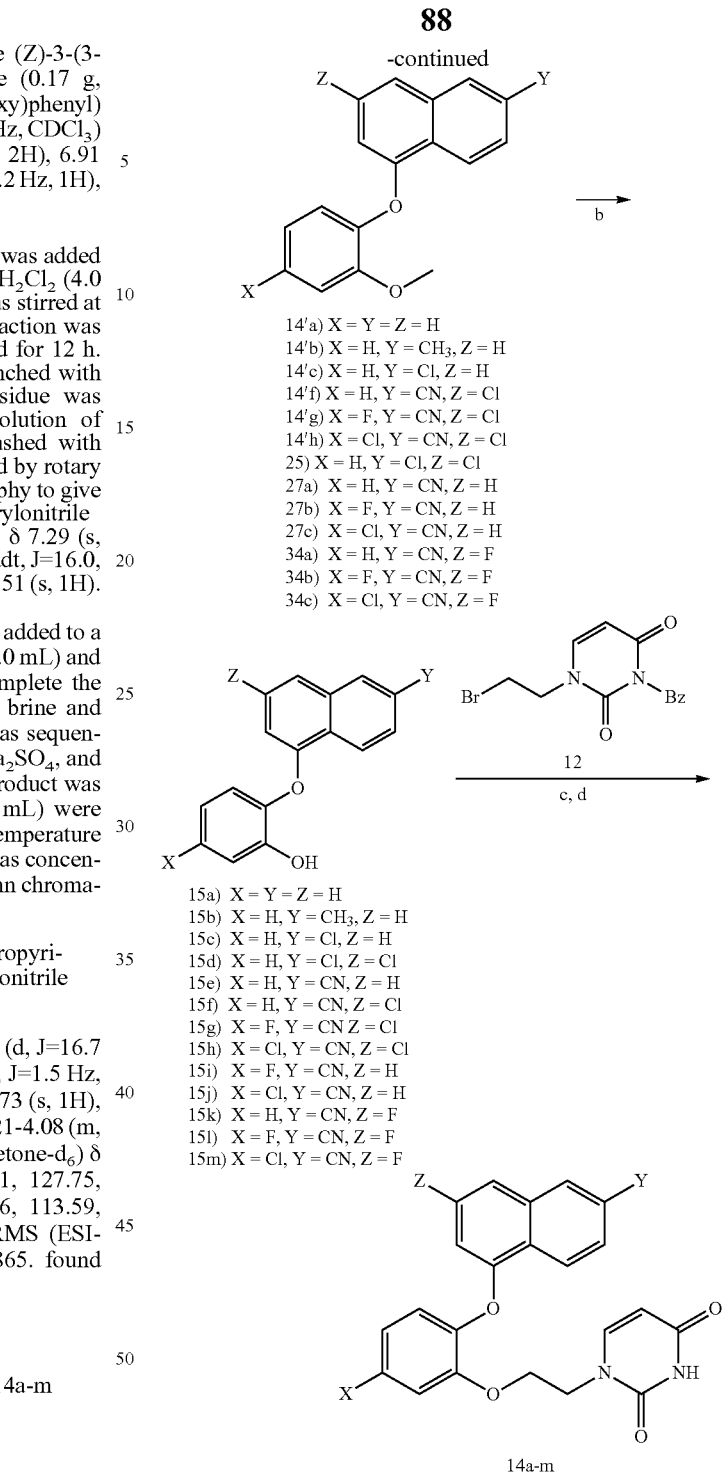

14'a) X = Y = Z = H
14'b) X = H, Y = CH$_3$, Z = H
14'c) X = H, Y = Cl, Z = H
14'f) X = H, Y = CN, Z = Cl
14'g) X = F, Y = CN, Z = Cl
14'h) X = Cl, Y = CN, Z = Cl
25) X = H, Y = Cl, Z = Cl
27a) X = H, Y = CN, Z = H
27b) X = F, Y = CN, Z = H
27c) X = Cl, Y = CN, Z = H
34a) X = H, Y = CN, Z = F
34b) X = F, Y = CN, Z = F
34c) X = Cl, Y = CN, Z = F

15a) X = Y = Z = H
15b) X = H, Y = CH$_3$, Z = H
15c) X = H, Y = Cl, Z = H
15d) X = H, Y = Cl, Z = Cl
15e) X = H, Y = CN, Z = H
15f) X = H, Y = CN, Z = Cl
15g) X = F, Y = CN Z = Cl
15h) X = Cl, Y = CN, Z = Cl
15i) X = F, Y = CN, Z = H
15j) X = Cl, Y = CN, Z = H
15k) X = H, Y = CN, Z = F
15l) X = F, Y = CN, Z = F
15m) X = Cl, Y = CN, Z = F 14a-m

Step a$^2$

A solution of naphthalenol (1.0 equiv), anisole (1.3 equiv), Cs$_2$CO$_3$ (1.5 equiv), CuI (0.1 equiv) and N,N-dimethylglycine hydrochloride (0.3 equiv) or 2,2,6,6-tetramethyl-3,5-heptanedione (0.4 equiv) in anhydrous dioxane (5.0 mL per 1.0 mmol of naphthalenol) was stirred at 90-100° C. under N$_2$ atmosphere in a sealed tube for 48 h. The reaction was cooled down, quenched with brine, and extracted with ethyl acetate (3×10 mL). The combined organic layer was dried over anhydrous Na$_2$SO$_4$, concentrated by rotary evaporation, and purified by column chromatography to give 14a-c and f-h.

1-(2-methoxyphenoxy)naphthalene (14'a)

(27%) ¹H NMR (600 MHz, CDCl$_3$) δ 8.33 (d, J=12.0 Hz, 1H), 7.86 (d, J=12.0 Hz, 1H), 7.57-7.51 (m, 3H), 7.33 (d, J=6.0 Hz, 1H), 7.17-7.13 (m, 1H), 7.06 (d, J=6.0 Hz, 1H), 6.96-6.93 (m, 2H), 6.75 (d, J=12.0 Hz, 1H), 3.86 (s, 3H). GC-MS (ES) for C$_{17}$H$_{14}$O$_2$ [M]$^+$ 250.

1-(2-methoxyphenoxy)-6-methylnaphthalene (14'b)[3]

(80%) ¹H NMR (400 MHz, CDCl$_3$) δ 8.20 (d, J=12.0 Hz, 1H), 7.63 (s, 1H), 7.47 (d, J=12.0 Hz, 1H), 7.34 (s, 1H), 7.31 (d, J=6.4 Hz, 2H), 7.15-7.11 (m, 1H), 7.04 (d, J=8.0 Hz, 1H), 6.91 (s, 1H), 6.70 (d, J=12.0 Hz, 1H), 3.86 (s, 3H), 2.52 (s, 3H). GC-MS (ES) for C$_{18}$H$_{16}$O$_2$ [M]$^+$ 264.

6-chloro-1-(2-methoxyphenoxy)naphthalene (14'c)

(46%) ¹H NMR (600 MHz, CDCl$_3$) δ 8.30 (d, J=12.0 Hz, 1H), 7.84 (d, J=6.0 Hz, 1H), 7.46-7.43 (m, 2H), 7.33 (t, J=12.0 Hz, 1H), 7.18 (td, J=12.0, 2.0 Hz, 1H), 7.05 (d, J=6.0 Hz, 1H), 6.97-6.94 (m, 2H), 6.69 (d, J=12.0 Hz, 1H), 3.83 (s, 3H). GC-MS (ES) for C$_{17}$H$_{13}$ClO$_2$ [M]$^+$ 284.

7-chloro-5-(2-methoxyphenoxy)-2-naphthonitrile (14'f)

(27%) ¹H NMR (400 MHz, Acetone-d$_6$) δ 8.52 (d, J=8.7 Hz, 1H), 8.48-8.42 (m, 1H), 7.83 (dd, J=8.7, 1.6 Hz, 1H), 7.78 (dd, J=1.3, 0.6 Hz, 1H), 7.35 (ddd, J=8.1, 7.5, 1.7 Hz, 1H), 7.26 (td, J=7.9, 1.5 Hz, 2H), 7.09 (td, J=7.7, 1.6 Hz, 1H), 6.62 (d, J=1.9 Hz, 1H), 3.77 (s, 3H). LC-MS (ES) for C$_{18}$H$_{12}$ClNO$_2$ [M+1]$^+$ 310.06.

7-chloro-5-(4-fluoro-2-methoxyphenoxy)-2-naphthonitrile (14'g)

(27%) ¹H NMR (400 MHz, Acetone-d$_6$) δ 8.53-8.46 (m, 1H), 8.45-8.38 (m, 1H), 7.81 (dd, J=8.7, 1.5 Hz, 1H), 7.78-7.72 (m, 1H), 7.32 (dd, J=8.8, 5.8 Hz, 1H), 7.09 (dd, J=10.5, 2.9 Hz, 1H), 6.84 (td, J=8.4, 2.9 Hz, 1H), 6.64 (d, J=1.8 Hz, 1H), 3.79 (s, 3H). LC-MS (ES) for C$_{18}$H$_{11}$ClFNO$_2$ [M+1]$^+$ 328.10.

7-chloro-5-(4-chloro-2-methoxyphenoxy)-2-naphthonitrile (14'h)

(30%) ¹H NMR (500 MHz, Acetone-d$_6$) δ 8.36 (d, J=8.7 Hz, 1H), 8.34-8.31 (m, 1H), 7.73-7.65 (m, 2H), 7.17 (d, J=1.2 Hz, 1H), 7.00-6.93 (m, 2H), 6.60 (d, J=1.8 Hz, 1H), 3.70 (s, 3H). LC-MS (ES) for C$_{18}$H$_{11}$Cl$_2$NO$_2$ [M+1]$^+$ 344.06.

Step b

A solution of BBr$_3$ (2.5 equiv, 1.0M in DCM) was added dropwise to a solution of the corresponding catechol diether intermediate (1.0 equiv) in anhydrous DCM (1.0 mL per 1.0 mmol of catechol diether intermediate) under N$_2$ atmosphere at −78° C. The reaction mixture was stirred for an additional 3h at 0° C. After this period, the solution was quenched with ice water, and the organic layer washed with water. The organic layer was dried over anhydrous Na$_2$SO$_4$, concentrated by rotary evaporation, and purified by column chromatography to give 15a-m.

2-(naphthalen-1-yloxy)phenol (15a)

(75%) ¹H NMR (600 MHz, CDCl$_3$) δ 8.25-8.23 (m, 1H), 7.91-7.88 (m, 1H), 7.64 (d, J=12.0 Hz, 1H), 7.56-7.54 (m, 2H), 7.37 (t, J=12.0 Hz, 2H), 7.12-7.07 (m, 2H), 6.92 (d, J=12.0 Hz, 1H), 6.85 (s, 1H), 5.67 (s, 1H).

2-((6-methylnaphthalen-1-yl)oxy)phenol (15b)

(10%) ¹H NMR (600 MHz, CDCl$_3$) 8.11 (d, J=12.0 Hz, 1H), 7.66 (s, 1H), 7.55 (d, J=8.0 Hz, 1H), 7.38-7.31 (m, 2H), 7.09-7.06 (m, 2H), 6.85 (d, J=8.0 Hz, 1H), 6.83-6.81 (m, 2H), 5.68 (s, 1H), 2.54 (s, 3H). GC-MS (ES) for C$_{17}$H$_{14}$O$_2$ [M]$^+$ 250.

2-((6-chloronaphthalen-1-yl)oxy)phenol (15c)

(75%) ¹H NMR (600 MHz, CDCl$_3$) 8.21 (d, J=6.0 Hz, 1H), 7.87 (d, J=1.0 Hz, 1H), 7.53 (d, J=12.0 Hz, 1H), 7.48 (s, 1H), 7.39 (t, J=6.0 Hz, 1H), 7.11-7.09 (m, 2H), 6.88 (d, J=12.0 Hz, 1H), 6.86-6.83 (m, 2H), 5.61 (s, 1H).

2-((3,6-dichloronaphthalen-1-yl)oxy)phenol (15d)

(44%) ¹H NMR (600 MHz, CDCl$_3$) δ 8.21 (d, J=12.0 Hz, 1H), 7.77 (s, 1H), 7.49 (s, 1H), 7.17-7.12 (m, 2H), 7.06-7.05 (m, 1H), 6.96-6.92 (m, 2H), 6.77 (s, 1H), 5.43 (s, 1H)

5-(2-hydroxyphenoxy)-2-naphthonitrile (15e)

(51%) ¹H NMR (400 MHz, Acetone-d$_6$) δ 8.42 (s, 1H), 8.37-8.33 (m, 2H), 7.65 (dd, J=8.7, 1.6 Hz, 1H), 7.61 (d, J=8.3 Hz, 1H), 7.41 (t, J=8.0 Hz, 1H), 7.03 (ddd, J=8.1, 7.2, 1.6 Hz, 1H), 6.96 (ddd, J=8.0, 3.3, 1.6 Hz, 2H), 6.80 (ddd, =8.0, 7.2, 1.7 Hz, 1H), 6.72 (dd, J=7.8, 0.9 Hz, 1H). LC-MS (ES) for C$_{17}$H$_{11}$NO$_2$ [M+1]$^+$ 262.09.

7-chloro-5-(2-hydroxyphenoxy)-2-naphthonitrile (15f)

(31%) ¹H NMR (500 MHz, CDCl$_3$) δ 8.40 (d, J=8.7 Hz, 1H), 8.17-8.10 (m, 1H), 7.69-7.60 (m, 2H), 7.21-7.16 (m, 1H), 7.16-7.11 (m, 1H), 7.01-6.93 (m, 2H), 6.90-6.88 (m, 1H), 5.47 (s, 1H). LC-MS (ES) for C$_{17}$H$_{10}$ClNO$_2$ [M+1]$^+$ 296.20.

7-chloro-5-(4-fluoro-2-hydroxyphenoxy)-2-naphthonitrile (15g)

(79%) ¹H NMR (500 MHz, Acetone-d$_6$) δ 8.64 (d, J=8.7 Hz, 1H), 8.59 (s, 1H), 7.96 (dd, J=8.7, 1.6 Hz, 1H), 7.93 (d, J=1.6 Hz, 1H), 7.40 (dd, J=8.9, 5.7 Hz, 1H), 7.02 (dd, J=10.0, 3.0 Hz, 1H), 6.90 (td, J=8.7, 3.0 Hz, 1H), 6.86 (d, J=1.8 Hz, 1H). LC-MS (ES) for C$_{17}$H$_9$ClFNO$_2$ [M+1]$^+$ 314.06.

7-chloro-5-(4-chloro-2-hydroxyphenoxy)-2-naphthonitrile (15h)

(87%) ¹H NMR (500 MHz, Acetone-d$_6$) δ 8.42 (d, J=8.7 Hz, 1H), 8.39 (d, J=1.3 Hz, 1H), 7.78-7.73 (m, 2H), 7.18 (d, J=8.6 Hz, 1H), 7.08 (d, J=2.5 Hz, 1H), 6.94 (dd, J=8.6, 2.5 Hz, 1H), 6.72 (d, J=1.8 Hz, 1H). LC-MS (ES) for C$_{18}$H$_{12}$ClNO$_2$ [M+1]$^+$ 331.38.

5-(4-fluoro-2-hydroxyphenoxy)-2-naphthonitrile (15i)

(26%) ¹H NMR (400 MHz, Acetone-d$_6$) δ 8.91 (s, 1H), 8.41-8.34 (m, 2H), 7.67 (dd, J=8.7, 1.7 Hz, 1H), 7.62 (d, J=8.4 Hz, 1H), 7.42 (t, J=8.0 Hz, 1H), 7.03 (dd, J=8.9, 5.7 Hz, 1H), 6.78-6.69 (m, 2H), 6.59 (ddd, J=8.9, 8.2, 3.0 Hz, 1H). LC-MS (ES) for $C_{17}H_{10}FNO_2$ [M+1]$^+$ 280.08.

5-(4-chloro-2-hydroxyphenoxy)-2-naphthonitrile (15j)

(31%) $^1$H NMR (400 MHz, Acetone-d$_6$) δ 8.52 (d, J=8.7 Hz, 1H), 8.47-8.43 (m, 1H), 7.83 (dd, J=8.7, 1.6 Hz, 1H), 7.78 (dd, J=1.3, 0.6 Hz, 1H), 7.35 (ddd, J=8.1, 7.5, 1.7 Hz, 1H), 7.26 (td, J=7.9, 1.5 Hz, 2H), 7.09 (td, J=7.7, 1.6 Hz, 1H), 6.62 (d, J=1.9 Hz, 1H), 6.47 (s, 1H). LC-MS (ES) for $C_{17}H_{10}FNO_2$ [M+1]$^+$ 280.08.

7-fluoro-5-(2-hydroxyphenoxy)-2-naphthonitrile (15k)

(53%) $^1$H NMR (400 MHz, Acetone-d$_6$) δ 8.71 (s, 1H), 8.51 (d, J=8.7 Hz, 1H), 8.44 (s, 1H), 7.76 (dd, J=8.7, 1.4 Hz, 1H), 7.43 (dd, J=9.3, 2.2 Hz, 1H), 7.26-7.16 (m, 2H), 7.13 (dd, J=8.5, 1.4 Hz, 1H), 6.98 (td, J=7.6, 1.6 Hz, 1H), 6.58 (dd, J=10.5, 2.2 Hz, 1H). LC-MS (ES) for $C_{17}H_{10}FNO_2$ [M+1]$^+$ 280.22.

7-fluoro-5-(4-fluoro-2-hydroxyphenoxy)-2-naphthonitrile (15l)

(38%) $^1$H NMR (400 MHz, Acetone-d$_6$) δ 9.23 (s, 1H), 8.51 (d, J=8.7 Hz, 1H), 8.46 (s, 1H), 8.04-7.99 (m, 1H), 7.78 (dd, J=8.7, 1.3 Hz, 1H), 7.28 (dd, J=8.9, 5.7 Hz, 1H), 6.90 (dd, J=10.0, 3.0 Hz, 1H), 6.77 (td, J=8.5, 3.0 Hz, 1H), 6.63 (dd, J=10.5, 2.3 Hz, 1H). LC-MS (ES) for $C_{17}H_9F_2NO_2$ [M+1]+ 297.92.

5-(4-chloro-2-hydroxyphenoxy)-7-fluoro-2-naphthonitrile (15m)

(52%) $^1$H NMR (400 MHz, Acetone-d$_6$) δ 9.22 (s, 1H), 8.49 (d, J=8.7 Hz, 1H), 8.46 (s, 1H), 8.04-7.97 (m, 1H), 7.78 (dd, J=8.7, 1.4 Hz, 1H), 7.25 (d, J=8.6 Hz, 1H), 7.15 (d, J=2.4 Hz, 1H), 7.01 (dd, J=8.6, 2.5 Hz, 1H), 6.70 (dd, J=10.4, 2.3 Hz, 1H). LC-MS (ES) for $C_{17}H_9ClFNO_2$ [M+1]$^+$ 314.02.

Step d and e 12 (1.2 equiv) and K$_2$CO$_3$ (2.0 equiv) were added to a solution of the corresponding catechol aryl ether intermediate (1.0 equiv) in anhydrous DMF (1.0 mL per 1.0 mmol catechol aryl ether intermediate) and the mixture was stirred for 3 h at 60° C. to complete the reaction. The reaction mixture was poured into brine and extracted with ethyl acetate. The organic layer was sequentially washed with brine, dried over anhydrous Na$_2$SO$_4$, and concentrated by rotary evaporation. The crude product was dissolved in DCM (0.5 mL per 1.0 mmol catechol diether intermediate) and NH$_4$OH (0.5 mL per 1.0 mmol catechol aryl ether intermediate) were added. The reaction mixture was stirred at room temperature for 16 h. After completion, the reaction mixture was concentrated by rotary evaporation and purified by column chromatography to give 14a-m.

1-(2-(2-(naphthalen-1-yloxy)phenoxy)ethyl)pyrimidine-2,4(1H,3H)-dione (14a)

(10%) $^1$H NMR (400 MHz, Acetone-d$_6$) δ 9.86 (s, br, 1H), 8.39-8.37 (m, 1H), 7.98-7.96 (m, 1H), 7.63-7.58 (m, 3H), 7.32 (t, J=12.0 Hz, 1H), 7.26-7.18 (m, 3H), 7.09-7.05 (m, J=12.0, 2.0 Hz, 1H), 6.57 (d, J=12.0 Hz, 1H), 6.52 (d, J=12.0 Hz, 1H), 4.66 (d, J=12.0 Hz, 1H), 4.23 (t, J=6.0 Hz, 2H), 3.87 (t, J=6.0 Hz, 2H). $^{13}$C NMR (150 MHz, Acetone-d$_6$) δ 155.06, 151.42, 146.19, 144.99, 135.79, 128.64, 127.53, 126.76, 126.59, 126.22, 123.40, 122.76, 122.64, 122.60, 115.20, 109.24, 101.05, 67.40, 48.46. HR-MS (ES) calcd for $C_{22}H_{18}N_2O_4$ [M+1]$^+$ 375.1346 found 375.1370.

1-(2-(2-((6-methylnaphthalen-1-yl)oxy)phenoxy)ethyl)pyrimidine-2,4(1H,3H)-dione (14b)

(10%) $^1$H NMR (400 MHz, CD$_2$Cl$_2$) δ 8.49 (s, br, 1H), 8.25 (d, J=10.0 Hz, 1H), 7.68 (s, 1H), 7.46-7.41 (m, 2H), 7.24-7.19 (m, 2H), 7.15 (d, J=10.0 Hz, 1H), 7.06-7.01 (m, 2H), 6.47 (d, J=10.0 Hz, 1H), 6.30 (d, J=10.0 Hz, 1H), 4.76 (d, J=10.0 Hz, 1H), 4.15 (t, J=5.0 Hz, 2H), 3.80 (t, J=6.0 Hz, 2H), 2.55 (s, 3H). $^{13}$C NMR (100 MHz, CD$_2$Cl$_2$) δ 163.88, 154.69, 150.97, 150.71, 146.18, 144.82, 137.20, 135.60, 128.58, 127.25, 126.36, 126.19, 123.25, 122.74, 122.10, 121.80, 114.59, 108.20, 101.23, 67.13, 21.98. HR-MS (ES) calcd for $C_{23}H_{20}N_2O_4$ [M+1]$^+$ 389.1502 found 389.1505.

1-(2-(2-((6-chloronaphthalen-1-yl)oxy)phenoxy)ethyl)pyrimidine-2,4(1H,3H)-dione (14c)

(10%) $^1$H NMR (400 MHz, Acetone-d$_6$) δ 9.83 (s, br, 1H), 8.40 (d, J=12.0 Hz, 1H), 8.03 (s, 1H), 7.61-7.56 (m, 2H), 7.38 (t, J=12.0 Hz, 1H), 7.28-7.20 (m, 3H), 7.09 (d, J=12.0 Hz, 1H), 6.62 (d, J=12.0 Hz, 1H), 6.57 (d, J=12.0 Hz, 1H), 4.72 (d, J=12.0 Hz, 1H), 4.24 (t, J=6.0 Hz, 2H), 3.89 (t, J=6.0 Hz, 2H). $^{13}$C NMR (150 MHz, Acetone-d$_6$) δ 155.23, 151.45, 146.11, 144.60, 136.49, 132.97, 128.36, 127.27, 127.13, 127.07, 124.90, 124.46, 123.55, 122.83, 121.81, 115.26, 109.49, 101.07, 67.34, 48.44. HR-MS (ES) calcd for $C_{22}H_{17}ClN_2O_4$ [M+1]$^+$ 409.0956 found 409.0940.

1-(2-(2-((3,6-dichloronaphthalen-1-yl)oxy)phenoxy)ethyl)pyrimidine-2,4(1H,3H)-dione (14d)

(10%) $^1$H NMR (500 MHz, Acetone-d$_6$) δ 8.39 (d, J=10.0 Hz, 1H), 8.01 (s, 1H), 7.68 (s, 1H), 7.65-7.61 (m, 2H), 7.33 (d, J=5.0 Hz, 1H), 7.30-7.28 (m, 2H), 7.20-7.17 (m, 1H), 7.14 (d, J=5.0 Hz, 2H), 6.70 (d, J=10.0 Hz, 1H), 6.43 (s, 1H), 4.73 (d, J=10.0 Hz, 1H), 4.28 (t, J=5.0 Hz, 2H), 3.93 (t, J=5.0 Hz, 2H). $^{13}$C NMR (125 MHz, Acetone-d$_6$) δ 163.60, 156.29, 151.38, 146.00, 136.61, 127.89, 127.57, 126.67, 125.01, 123.90, 122.98, 120.42, 115.32, 109.63, 101.02, 67.24, 48.47. HR-MS (ES) calcd for $C_{22}H_{16}Cl_2N_2O_4$ [M+1]$^+$ 443.0566 found 443.0560.

5-(2-(2-(2,4-dioxo-3,4-dihydropyrimidin-1(2H)-yl)ethoxy)phenoxy)-2-naphthonitrile (14e)

(24%) $^1$H NMR (500 MHz, CDCl$_3$) δ 8.49 (d, J=8.7 Hz, 1H), 8.31-8.28 (m, 2H), 7.85-7.80 (m, 1H), 7.71 (dd, J=8.7, 1.5 Hz, 1H), 7.58 (d, J=8.2 Hz, 1H), 7.38 (t, J=8.0 Hz, 1H), 7.15 (dd, J=7.9, 1.6 Hz, 1H), 7.07 (td, J=7.8, 1.3 Hz, 1H), 7.02 (d, J=8.2 Hz, 1H), 6.65 (d, J=7.7 Hz, 1H), 6.40 (d, J=7.9 Hz, 1H), 4.75 (d, J=7.9 Hz, 1H), 4.22-4.17 (m, 2H), 3.91-3.86 (m, 3H). $^{13}$C NMR (126 MHz, CDCl$_3$) δ 164.10, 154.18, 150.93, 145.08, 139.31, 134.12, 133.58, 127.94, 126.38, 123.83, 123.43, 122.33, 119.05, 110.63, 110.38, 108.69, 108.51, 102.54, 102.32, 101.27, 100.18, 66.67, 48.15. HR-MS (ES) calcd for $C_{23}H_{17}N_3O_4$ [M+1]$^+$ 400.1311. found 400.1307.

7-chloro-5-(2-(2-(2,4-dioxo-3,4-dihydropyrimidin-1(2H)-yl)ethoxy)phenoxy)-2-naphthonitrile (14f)

$^1$H NMR (500 MHz, CDCl$_3$) δ 8.49 (d, J=8.7 Hz, 1H), 8.46 (s, 1H), 8.21 (s, 1H), 7.74 (dd, J=8.7, 1.4 Hz, 1H), 7.59 (s,

1H), 7.36-7.30 (m, 1H), 7.21 (dd, J=7.9, 1.5 Hz, 1H), 7.14 (t, J=7.7 Hz, 1H), 7.09 (d, J=7.4 Hz, 1H), 6.57 (d, J=1.7 Hz, 1H), 6.47 (d, 7.9 Hz, 1H), 4.83 (dd, J=7.9, 1.8 Hz, 1H), 4.25 (t, J=4.6 Hz, 2H), 3.94 (t, J=4.6 Hz, 2H). $^{13}$C NMR (101 MHz, DMSO-D$_6$) δ 157.98, 150.04, 145.59, 145.16, 139.94, 137.78, 128.97, 128.81, 128.07, 122.40, 121.75, 119.97, 118.77, 118.42, 118.14, 115.92, 113.75, 109.65, 106.96, 106.79, 96.43, 61.65, 43.50. HR-MS (ES) calcd for C$_{23}$H$_{16}$ClN$_3$O$_4$ [M+1]$^+$ 433.8438. found 433.8487.

7-chloro-5-(2-(2-(2,4-dioxo-3,4-dihydropyrimidin-1(2H)-yl)ethoxy)-4-fluorophenoxy)-2-naphthonitrile (14g)

(30%) $^1$H NMR (400 MHz, DMSO-D$_6$) δ 11.10 (s, 1H), 8.58 (s, 1H), 8.37 (d, J=8.7 Hz, 1H), 7.92-7.77 (m, 2H), 7.34 (dd, J=8.8, 5.8 Hz, 1H), 7.26 (dd, J=10.6, 2.7 Hz, 1H), 6.91 (td, J=8.5, 2.8 Hz, 1H), 6.79 (d, J=7.8 Hz, 1H), 6.49 (d, J=1.7 Hz, 1H), 4.65 (d, J=7.8 Hz, 1H), 4.19 (t, J=4.7 Hz, 2H), 3.81 (t, J=4.7 Hz, 2H). $^{13}$C NMR (101 MHz, DMSO-D$_6$) δ 163.63, 159.48, 155.02, 151.27, 151.05, 145.60, 138.55, 133.85, 132.56, 128.63, 127.87, 127.30, 124.73, 124.22, 123.69, 121.25, 119.18, 111.09, 108.48, 103.29, 100.29, 66.77, 47.18. HR-MS (ES) calcd for C$_{23}$H$_{15}$ClFN$_3$O$_4$ [M+1]$^+$ 452.0813. found 452.0842.

7-chloro-5-(4-chloro-2-(2-(2,4-dioxo-3,4-dihydropyrimidin-1(2H)-yl)ethoxy)phenoxy)-2-naphthonitrile (14h) (26%)

$^1$H NMR (600 MHz, CDCl$_3$) δ 8.95 (s, 1H), 8.45 (d, J=8.5 Hz, 1H), 8.17 (s, 1H), 7.82 (d, J=7.4 Hz, 1H), 7.71-7.68 (m, 1H), 7.57-7.52 (m, 1H), 7.45 (t, J=7.7 Hz, 1H), 7.32-7.27 (m, 1H), 7.11 (t, J=7.7 Hz, 1H), 6.45 (d, J=7.8 Hz, 1H), 4.82 (d, J=6.6 Hz, 1H), 4.24-4.20 (m, 2H), 3.90 (t, J=4.6 Hz, 2H). $^{13}$C NMR (101 MHz, DMSO-D$_6$) δ 159.00, 151.42, 145.37, 144.20, 139.90, 135.13, 128.99, 128.47, 128.01, 121.88, 121.05, 120.15, 119.02, 118.19, 118.10, 114.68, 112.81, 108.15, 106.89, 106.66, 97.10, 63.94, 46.38. HR-MS (ES) calcd for C$_{23}$H$_{15}$ClFN$_3$O$_4$ [M+1]$^+$ 468.0440. found 468.0442.

5-(2-(2-(2,4-dioxo-3,4-dihydropyrimidin-1(2H)-yl)ethoxy)-4-fluorophenoxy)-2-naphthonitrile (14i)

(25%) $^1$H NMR (500 MHz, CDCl$_3$) δ 8.49 (d, J=8.6 Hz, 1H), 8.31 (s, 1H), 7.72 (d, J=8.7 Hz, 1H), 7.60 (d, J=8.1 Hz, 1H), 7.39 (t, J=7.3 Hz, 1H), 7.20-7.08 (m, 1H), 6.79 (t, J=8.3 Hz, 2H), 6.62 (d, J=7.7 Hz, 1H), 6.40-6.30 (m, 1H), 4.76-4.64 (m, 1H), 4.21-4.12 (m, 2H), 3.84-3.76 (m, J=2H). $^{13}$C NMR (126 MHz, CDCl$_3$) δ 164.10, 154.18, 150.93, 145.08, 139.31, 134.12, 133.58, 127.94, 126.38, 123.83, 123.43, 122.33, 119.05, 110.63, 110.38, 108.69, 108.51, 102.54, 102.32, 101.27, 100.18, 66.67, 48.15. HR-MS (ES) calcd for C$_{23}$H$_{16}$FN$_3$O$_4$ [M+1]$^+$ 418.1215. found 418.1254.

5-(4-chloro-2-(2-(2,4-dioxo-3,4-dihydropyrimidin-1(2H)-yl)ethoxy)phenoxy)-2-naphthonitrile (14j)

(27%) $^1$H NMR (500 MHz, DMSO-d$_6$) δ 11.18 (s, 1H), 8.69 (d, J=1.2 Hz, 1H), 8.41 (d, J=8.7 Hz, 1H), 7.91 (dd, J=8.7, 1.6 Hz, 1H), 7.79 (d, J=8.4 Hz, 1H), 7.54 (t, J=8.0 Hz, 1H), 7.45 (d, J=2.4 Hz, 1H), 7.27 (d, J=8.5 Hz, 1H), 7.16 (dd, J=8.5, 2.4 Hz, 1H), 6.89 (d, J=7.8 Hz, 1H), 6.84-6.77 (m, 1H), 4.82 (d, J=7.8 Hz, 1H), 4.28 (t, J=5.0 Hz, 2H), 3.88 (t, J=5.0 Hz, 2H). $^{13}$C NMR (126 MHz, DMSO-D$_6$) δ 163.63, 153.37, 151.02, 150.97, 145.64, 142.51, 134.63, 133.54, 130.30, 128.31, 126.76, 126.16, 123.81, 123.35, 122.96, 121.96, 119.40, 115.40, 112.03, 109.67, 100.39, 66.75, 47.06. HR-MS (ES) calcd for C$_{23}$H$_{16}$ClN$_3$O$_4$ [M+1]$^+$ 434.0908. found 434.0953.

5-(2-(2-(2,4-dioxo-3,4-dihydropyrimidin-1(2H)-yl)ethoxy)phenoxy)-7-fluoro-2-naphthonitrile (14k)

(27%) $^1$H NMR (400 MHz, DMSO-d$_6$) δ 11.06 (s, 1H), 8.57 (s, 1H), 8.38 (d, J=8.7 Hz, 1H), 7.83 (d, J=8.7 Hz, 1H), 7.50-7.44 (m, 1H), 7.33-7.21 (m, 2H), 7.08 (t, J=7.4 Hz, 1H), 6.80 (d, J=7.9 Hz, 1H), 6.39 (dd, J=10.3, 2.1 Hz, 1H), 4.64 (d, J=7.8 Hz, 1H), 4.17 (t, J=4.7 Hz, 2H), 3.81 (t, J=4.6 Hz, 2H). $^{13}$C NMR (151 MHz, DMSO-d$_6$) δ 163.70, 161.83, 160.20, 155.90, 151.09, 150.28, 145.72, 142.44, 134.06, 127.64, 126.23, 123.77, 123.57, 123.17, 122.55, 119.26, 115.20, 111.03, 105.59, 101.79, 100.22, 66.30, 47.44. HR-MS (ES) calcd for C$_{23}$H$_{16}$FN$_3$O$_4$ [M+1]$^+$ 418.1203 found 418.1211.

5-(2-(2-(2,4-dioxo-3,4-dihydropyrimidin-1(2H)-yl)ethoxy)-4-fluorophenoxy)-7-fluoro-2-naphthonitrile (14l)

(28%) $^1$H NMR (500 MHz, DMSO) δ 11.08 (s, 1H), 8.57 (s, 1H), 8.38 (d, J=8.7 Hz, 1H), 7.83 (d, J=8.6 Hz, 1H), 7.51-7.44 (m, 1H), 7.33 (dd, J=8.7, 5.8 Hz, 1H), 7.25 (dd, J=10.6, 2.7 Hz, 1H), 6.91 (td, J=8.5, 2.6 Hz, 1H), 6.79 (d, J=7.8 Hz, 1H), 6.46 (dd, J=10.3, 1.9 Hz, 1H), 4.64 (d, J=7.8 Hz, 1H), 4.19 (t, J=4.8 Hz, 2H), 3.82 (t, J=4.7 Hz, 2H). $^{13}$C NMR (126 MHz, DMSO) δ 163.62, 162.05, 161.67, 160.10, 159.75, 156.03, 151.31, 151.06, 145.65, 138.66, 134.00, 126.24, 123.76, 123.49, 119.25, 111.05, 108.25, 105.78, 103.53, 101.49, 100.27, 66.75, 47.20. HR-MS (ES) calcd for C$_{23}$H$_{15}$F$_2$N$_3$O$_4$ [M+1]$^+$ 436.1122 found 436.1129.

5-(4-chloro-2-(2-(2,4-dioxo-3,4-dihydropyrimidin-1(2H)-yl)ethoxy)phenoxy)-7-fluoro-2-naphthonitrile (14m)

(30%) $^1$H NMR (400 MHz, DMSO) δ 11.11-11.06 (m, 1H), 8.56 (s, 1H), 8.34 (d, J=8.7 Hz, 1H), 7.82 (dd, J=8.7, 1.4 Hz, 1H), 7.49 (dd, J=9.4, 2.1 Hz, 1H), 7.40 (d, J=2.3 Hz, 1H), 7.29 (d, J=8.5 Hz, 1H), 7.11 (dd, J=8.5, 2.3 Hz, 1H), 6.82 (d, J=7.8 Hz, 1H), 6.54 (dd, J=10.3, 2.3 Hz, 1H), 4.67 (dd, J=7.8, 2.2 Hz, 1H), 4.21 (t, J=4.9 Hz, 2H), 3.81 (t, J=4.8 Hz, 2H). $^{13}$C NMR (101 MHz, CDCl$_3$) δ 168.40, 166.99, 164.54, 160.23, 155.80, 150.42, 146.26, 138.77, 138.45, 135.95, 131.05, 129.09, 128.47, 128.27, 126.91, 123.98, 120.32, 115.79, 110.82, 107.07, 105.04, 71.49, 51.93. HR-MS (ES) calcd for C$_{23}$H$_{15}$ClFN$_3$O$_4$ [M+1]$^+$ 452.0777 found 452.0825.

Example 13

Synthesis of Compounds 13b and 13c

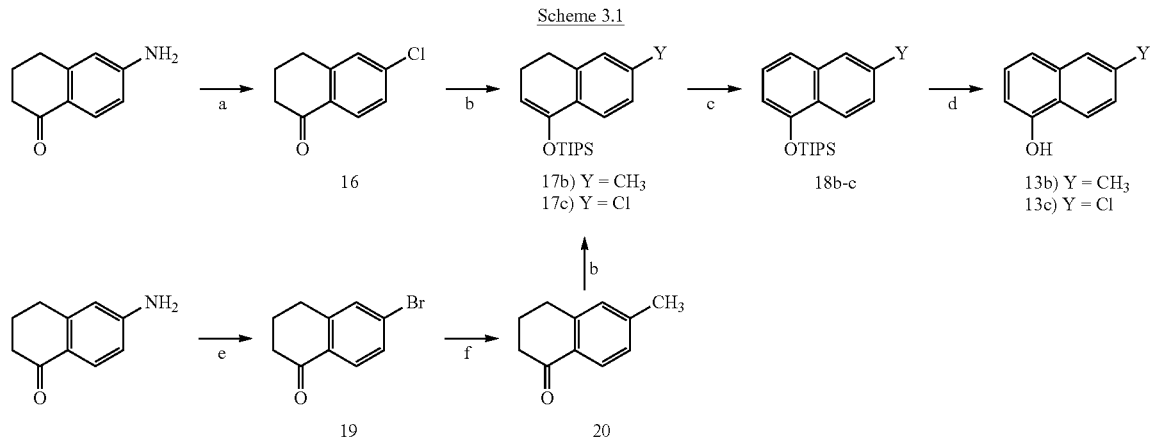

Scheme 3.1

Step a[4]

CuCl$_2$ (2.0 g, 15.0 mmol) and t-butyl nitrite (2.2 mL, 15.0 mmol) in dry CH$_3$CN were heated at 60° C., followed by the addition of 6-aminotetralone (2.0 g, 12.0 mmol). The reaction mixture was heated for 45 min, then cooled down at room temperature, quenched with 2N HCl (200 mL) and Et$_2$O (200 mL). The aqueous layer was extracted with Et$_2$O and the combined organic layer was washed with water, brine, dried over anhydrous Na$_2$SO$_4$, concentrated by rotary evaporation, and purified by column chromatography to give 6-chloro-3,4-dihydronaphthalen-1(2H)-one (16) (88%). 1H NMR (600 MHz, CDCl$_3$) δ 7.96 (d, J=6.0 Hz, 1H), 7.28-7.26 (m, 2H), 2.94 (t, J=6.0 Hz, 2H), 2.65 (t, J=6.0 Hz, 2H), 2.16-2.11 (m, 2H), 7.12-7.07 (m, 2H), 6.92 (d, J=12.0 Hz, 1H), 6.85 (s, 1H), 5.67 (s, 1H). GC-MS (ES) for C$_{10}$H$_9$ClO [M]$^+$ 180.

Step b[5]

To a solution of 6-chloro-3,4-dihydronaphthalen-1(2H)-one (1.0 g, 5.6 mmol) in dry DCM (15 mL) under N$_2$ atm was added TEA (1.3 mL, 9.4 mmol), followed by triisopropyl triflate (1.7 mL, 6.4 mmol). The reaction was stirred at room temperature for 2h, and washed with cold saturated aqueous NaHCO$_3$ (2×10 mL). The combined organic layer was dried over anhydrous Na$_2$SO$_4$, concentrated by rotary evaporation, and purified by column chromatography to give ((6-chloro-3,4-dihydronaphthalen-1-yl)oxy)triisopropylsilane (17c) (88%). 1H NMR (600 MHz, CDCl$_3$) δ 7.45 (d, J=6.0 Hz, 1H), 7.17-7.15 (m, 1H), 7.10 (s, 1H), 5.17 (t, J=6.0 Hz, 1H), 2.72 (t, J=12.0 Hz, 2H), 2.32-2.27 (m, 2H), 1.30-1.24 (m, 3H), 1.12 (d, J=12.0 Hz, 18H). GC-MS (ES) for C$_{19}$H$_{29}$ClOSi [M]$^+$ =336.

Step c[5]

To a solution of 17b-c (2.0 g, 5.9 mmol) and DDQ (2.7 g, 12 mmol) were dissolved in dry CH$_3$CN and heated at 80° C. for 30 min, cooled to room temperature, and diluted with heptane (10 mL). The crude was filtered, concentrated by rotary evaporation, and purified by column chromatography to give 18b-c.

triisopropyl((6-methylnaphthalen-1-yl)oxy)silane (18b)

(42%) 1H NMR (600 MHz, CDCl$_3$) δ 8.15 (d, J=12.0 Hz, 1H), 7.56 (s, 1H), 7.33 (d, J=12.0 Hz, 1H), 7.30-7.28 (m, 1H), 7.24 (d, J=12.0 Hz, 1H), 6.80 (d, J=6.0 Hz, 1H), 3.18 (s, 3H), 1.41-1.37 (m, 3H), 1.15 (d, J=12.0 Hz, 18H). GC-MS (ES) for C$_{20}$H$_{30}$OSi [M]$^+$ =314.

((6-chloronaphthalen-1-yl)oxy)triisopropylsilane (18c)

(70%) 1H NMR (600 MHz, CDCl$_3$) δ 8.19 (d, J=6.0 Hz, 1H), 7.77 (s, 1H), 7.38 (dd, J=6.0, 2.0 Hz, 1H), 7.33-7.32 (m, 2H), 6.86 (dd, J=6.0, 2.0 Hz, 1H), 1.43-1.38 (m, 3H), 1.16 (d, J=6.0 Hz, 18H). GC-MS (ES) for C$_{19}$H$_{27}$ClOSi [M]$^+$ =334.

Step d[5]

18 b-c (1.4 g, 4.2 mmol) was dissolved in NMP (2.0 mL), then a solution of NaOH (1.0 g) in water (1.0 mL) and MeOH (2.8 mL) was added and heated at 60° C. for 1.5 h. The crude was diluted with water (10.0 mL) and washed with hexane (10 mL). The aqueous layer was acidified with 6N HCl (6.0 mL) and extracted with EtOAc (3×10 mL). The combined organic layer was washed with water, dried over anhydrous Na$_2$SO$_4$, concentrated by rotary evaporation, and purified by column chromatography to give 13b-c.

6-methylnaphthalen-1-ol (13b)

(83%) 1H NMR (600 MHz, CDCl$_3$) δ 8.07 (d, J=12.0 Hz, 1H), 7.58 (s, 1H), 7.36-7.29 (m, 2H), 7.26 (d, J=12.0 Hz, 1H), 6.75 (d, J=12.0 Hz, 1H), 5.27 (s, 1H), 2.51 (s, 3H). GC-MS (ES) for C$_1$H$_{10}$O [M]$^+$=158.

6-chloronaphthalen-1-ol (13c)

(85%) 1H NMR (600 MHz, CDCl$_3$) δ 8.14 (d, J=12.0 Hz, 1H), 7.79 (s, 1H), 7.41 (dd, J=6.0, 1.0 Hz, 1H), 7.34-7.33 (m, 2H), 6.80 (d, J=6.0 Hz, 1H), 5.28 (s, 1H).

Step e[5]

6-aminotetralone (2.0 g, 12 mmol) was dissolved in 25% HBr (4.0 mL) at 0° C. and then, a solution of NaNO$_2$ (1.0 g, 15 mmol) in water (4.0 mL) was added slowly. Afterwards, a solution of CuBr (1.8 g, 4.0 mmol) in 48% HBr (4.0 mL) was added and the reaction was stirred at room temperature for 1.5 h. The solution was quenched by adding water and extracted with EtOAc (3×10 mL). The combined organic layer was dried over anhydrous Na$_2$SO$_4$, concentrated by rotary evaporation, and purified by column chromatography to give 6-bromo-3,4-dihydronaphthalen-1(2H)-one (19) (66%). NMR was according to reference 5.

Step f[6]

A solution of 19 (1.4 g, 6.1 mmol), methyl boronic acid (0.6 g, 9.3 mmol), Pd(OAc)$_2$ (0.07 g, 0.31 mmol), PPh$_3$ (0.16 g, 0.61 mmol), and K$_3$PO$_4$ (5.2 g, 24 mmol) in dry THF were stirred at reflux under N$_2$ atm overnight. After cooling at room temperature, crude was filtered through celite, concentrated by rotary evaporation, and purified by column chromatography to give 6-methyl-3,4-dihydronaphthalen-1(2H)-one (20) (88%). $^1$H NMR (600 MHz, CDCl$_3$) δ 7.93 (d, J=12.0 Hz, 1H), 7.11 (d, J=12.0 Hz, 1H), 7.06 (s, 1H), 2.92 (t, J=6.0 Hz, 2H), 2.63 (t, J=12.0 Hz, 2H), 2.37 (s, 3H), 2.13-2.10 (m, 2H). GC-MS (ES) for C$_{11}$H$_{12}$O [M]$^+$ 160.

Step g

To a solution of 20 (0.9 g, 5.3 mmol) in dry DCM (15 mL) under N$_2$ atm was added TEA (1.3 mL, 9.0 mmol), followed by triisopropyl triflate (1.7 mL, 6.4 mmol). The reaction was stirred at room temperature for 2h, washed with cold saturated aqueous NaHCO$_3$ (2×10 mL), dried over anhydrous Na$_2$SO$_4$, concentrated by rotary evaporation, and purified by column chromatography to give triisopropyl((6-methyl-3,4-dihydronaphthalen-1-yl)oxy)silane (17b) (84%). $^1$H NMR (600 MHz, CDCl$_3$) δ 7.41 (d, J=12.0 Hz, 1H), 7.01 (d, J=6.0 Hz, 1H), 6.94 (s, 1H), 5.11 (t, J=6.0 Hz, 1H), 2.71 (t, J=12.0 Hz, 2H), 2.32 (s, 3H), 2.29-2.26 (m, 2H), 1.30-1.24 (m, 3H), 1.12 (d, J=12.0 Hz, 18H). GC-MS (ES) for C$_{20}$H$_{32}$OSi [M]$^+$ = 316.

Example 14

Synthesis of Compounds 24a and 24b

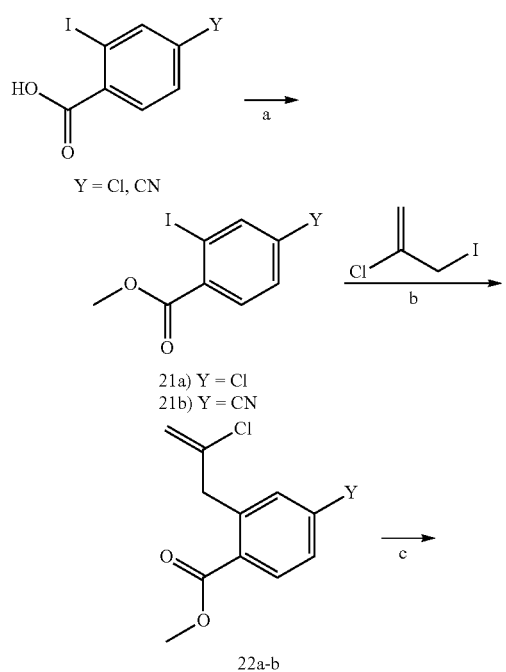

21a) Y = Cl
21b) Y = CN 22a-b

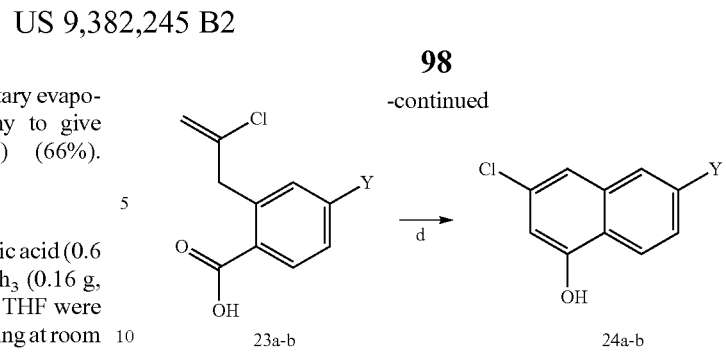

23a-b → 24a-b

Step a

To a stirred solution of the corresponding benzoic acid (1.0 equiv) in dry MeOH (2.0 mL per 1.0 mmol of benzoic acid) at 0° C. was added SOCl$_2$ (2.0 equiv) dropwise. After addition, the reaction was allowed to stir at room temperature overnight. The crude reaction was concentrated in vacuo, quenched with water, and extracted with EtOAc. The combined organic layer was washed with saturated aqueous NaHCO$_3$, dried over anhydrous Na$_2$SO$_4$, concentrated by rotary evaporation, and purified by column chromatography to give 21a-b.

methyl 4-chloro-2-iodobenzoate (21a)

(74%) $^1$H NMR (600 MHz, CDCl$_3$) δ 8.01 (s, 1H), 7.77 (d, J=12.0 Hz, 1H), 7.39 (d, J=12.0 Hz, 1H), 3.93 (s, 3H).

methyl 4-cyano-2-iodobenzoate (21b)

(84%) $^1$H NMR (400 MHz, CDCl$_3$) δ 8.24 (d, J=1.1 Hz, 1H), 7.83 (d, J=8.0 Hz, 1H), 7.71-7.64 (m, 1H), 3.95 (s, 3H). LC-MS (ES) for C$_9$H$_6$INO$_2$ [M+1]$^+$ 287.95.

Step b[7]

To a solution of the corresponding benzoate (1.0 equiv) in dry THF (2.0 mL per 1.0 mmol of benzoate) under N$_2$ atm was cooled to −40° C. Then, i-PrMgCl (2.0 equiv, 2M in THF) was added dropwise and stirred for 0.5 h at the same temperature. Afterwards CuCN.2LiCl (0.1 equiv) was added and after 5 minutes 2-chloro-3-iodo-propene (2.0 equiv) were added slowly. Then, the reaction was allowed to warm up at room temperature for 1.5 h. The reaction was quenched with saturated aqueous NH$_4$Cl and extracted with diethyl ether. The combined organic layer was washed with brine, dried over anhydrous Na$_2$SO$_4$, concentrated by rotary evaporation, and purified by column chromatography to give 22a and 22b.

methyl 4-chloro-2-(2-chloroallyl)benzoate (22a)

$^1$H NMR (600 MHz, CDCl$_3$) δ 7.89 (d, J=6.0 Hz, 1H), 7.34-7.31 (m, 2H), 5.27 (s, 1H), 5.04 (s, 1H), 4.06 (s, 2H), 3.89 (s, 3H). GC-MS (ES) for C$_{11}$H$_{10}$Cl$_2$O$_2$ [M]$^+$ 244.

methyl 2-(2-chloroallyl)-4-cyanobenzoate (22b)

(62%) $^1$H NMR (500 MHz, CDCl$_3$) δ 8.00 (d, J=8.0 Hz, 1H), 7.69-7.61 (m, 2H), 5.38-5.07 (m, 2H), 4.10 (s, 2H), 3.93 (s, 3H). LC-MS (ES) for C$_{12}$H$_{10}$ClNO$_2$ [M+1]$^+$ 236.05.

Step c[7]

To a solution of the corresponding allyl benzoate (1.0 equiv) dissolved in MeOH (20 mL) was added a solution of 2N NaOH (20 mL) and stirred at room temperature for 48 h. Then, the reaction was acidified with concentrated HCl to pH 2. After the solvent removed by rotary evaporation, the crude was extracted with EtOAc, washed with brine, and dried over anhydrous Na$_2$SO$_4$. The crude product was recrystallized from a 1:1 mixture of hexanes and EtOAc to afford benzoic acid intermediate 23a and 23b.

4-chloro-2-(2-chloroallyl)benzoic acid (23a)

(21%) $^1$H NMR (600 MHz, DMSO-$d_6$) δ 13.32 (s, 1H), 7.87 (d, J=12.0 Hz, 1H), 7.48-7.47 (m, 2H), 5.29 (s, 1H), 5.15 (s, 1H), 4.11 (s, 2H).

2-(2-chloroallyl)-4-cyanobenzoic acid (23b)

(63%) $^1$H NMR (400 MHz, Acetone-$d_6$) δ 8.12 (d, J=8.5 Hz, 1H), 7.84 (td, J=4.2, 1.7 Hz, 2H), 5.31-5.28 (m, 1H), 5.20 (q, J=1.3 Hz, 1H), 4.23 (s, 2H). LC-MS (ES) for $C_{11}H_8ClNO_2$ [M+1]$^+$ 222.02.

Step d[7]

To a solution of the corresponding benzoic acid (1.0 equiv) in dry DCM (2.0 mL per 1.0 mmol of benzoic acid) was added five drops of DMF and oxalyl chloride (2.0 equiv) dropwise. After stirring for 10 min, AlCl$_3$ (2.0 equiv) was added and the reaction was further stirred for 15 min. The reaction was quenched with 1N HCl and EtOAc. Afterwards, the organic layer was concentrated to half volume and heptane (17 mL) was added. The organic layer was washed with 10% aqueous NaOH (3×20 mL). The combined aqueous layer was acidified to pH 2 and extracted with EtOAc (3×10 mL). The combined organic layer was washed with water, brine, dried over anhydrous Na$_2$SO$_4$, concentrated by rotary evaporation, and purified by column chromatography to give 24a and 24b.

3,6-dichloronaphthalen-1-ol (24a)

(18%) $^1$H NMR (600 MHz, DMSO-$d_6$) δ 8.09 (d, J=12.0 Hz, 1H), 7.69 (d, J=4.0 Hz, 1H), 7.40 (dd, J=12.0, 4.0 Hz, 1H), 7.34 (s, 1H), 6.80 (d, J=4.0 Hz, 1H).

7-chloro-5-hydroxy-2-naphthonitrile (24b)

(62%) $^1$H NMR (500 MHz, Acetone-$d_6$) δ 8.41-8.35 (m, 2H), 7.73 (dd, J=8.8, 1.5 Hz, 1H), 7.64 (d, J=1.8 Hz, 1H), 7.13 (d, J=1.9 Hz, 1H). LC-MS (ES) for $C_{18}H_{12}ClNO_2$ [M+1]$^+$ 204.17.

Example 15

Synthesis of Compound 25[3]

Scheme 3.3

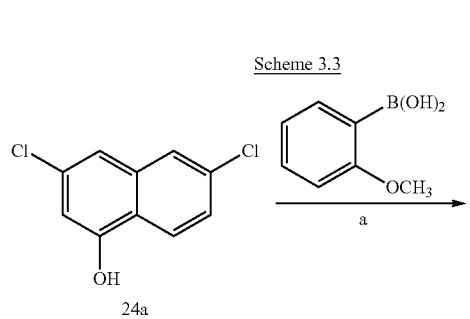

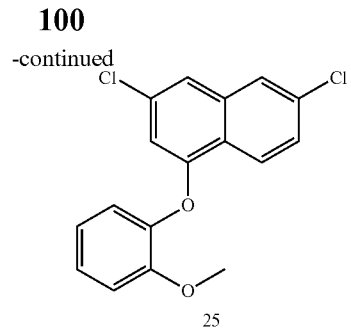

Step a

A solution of 3,6-dichloronaphthalen-1-ol (1.0 equiv), 2-methoxyphenylboronic acid (1.5 equiv), Cu(OAc)$_2$ (1.3 equiv), pyridine (5.0 equiv), and 4 Å MS in dry DCM (3.0 mL) was stirred at room temperature for 48 h. The reaction was filtered, concentrated by rotary evaporation, and purified by column chromatography to give 3,6-dichloro-1-(2-methoxyphenoxy)naphthalene (25) (38%). $^1$H NMR (400 MHz, CDCl$_3$) δ 8.30 (d, J=12.0 Hz, 1H), 7.73 (d, J=4.0 Hz, 1H), 7.44 (dd, J=12.0, 4.0 Hz, 1H), 7.40 (s, 1H), 7.10-7.06 (m, 2H), 7.02 (dd, J=3.4, 1.2 Hz, 1H), 6.96 (d, J=1.2 Hz, 1H), 6.54 (d, J=4.0 Hz, 1H), 3.80 (s, 3H), GC-MS (ES) for $C_{17}H_{12}Cl_2O_2$ [M]$^+$ 318.

Example 16

Synthesis Compounds 27a-c

Scheme 3.4

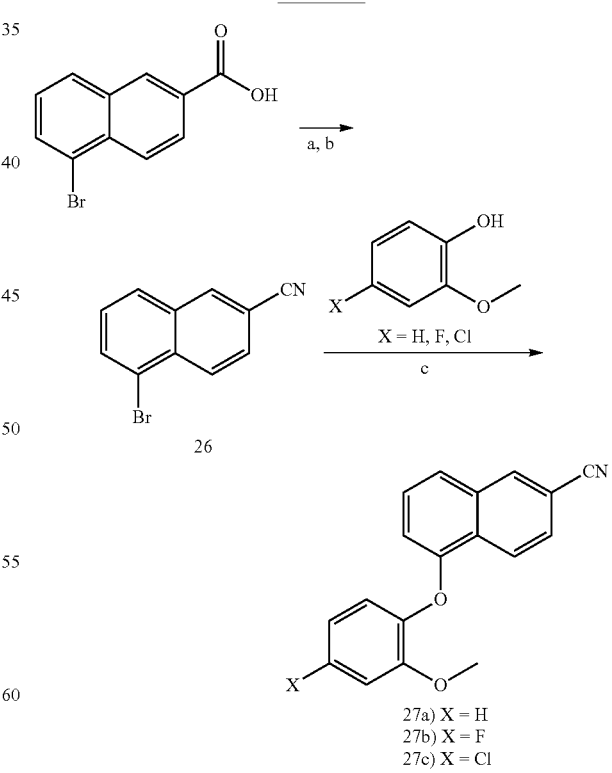

27a) X = H
27b) X = F
27c) X = Cl

Step a and b

DMF (3 drops) were added to a solution of 5-bromo-2-naphthoic acid (1.0 equiv) in SOCl$_2$ (4.0 mL) and the mixture was stirred for 3 h at 60° C. to complete the reaction. The reaction mixture was cooled to room temperature and dried by rotary evaporation. The crude product was dissolved in aq. NH$_4$OH (30%) (5.0 mL) and the mixture was stirred for overnight at room temperature. The mixture was diluted with DCM (20 mL) and washed twice with saturated NaHCO$_3$ aqueous solution (15 mL). The organic layer was dried over anhydrous Na$_2$SO$_4$, concentrated by rotary evaporation, and purified by column chromatography to give amide intermediate. Amide intermediate was dissolved in SOCl$_2$ (4.0 mL) and the mixture was refluxed for overnight. After cooling the solution was evaporated and dissolved in DCM, then it was washed with twice with saturated NaHCO$_3$ aqueous solution (15 mL). The organic layer was dried over anhydrous Na$_2$SO$_4$, concentrated by rotary evaporation, and purified by column chromatography to give 5-bromo-2-naphthonitrile (26) (52%). $^1$H NMR (400 MHz, Acetone-d$_6$) δ 8.58 (d, J=1.6 Hz, 1H), 8.40 (d, J=8.8 Hz, 1H), 8.17 (d, J=8.3 Hz, 1H), 8.11 (dd, J=7.5, 1.0 Hz, 1H), 7.94 (dd, J=8.8, 1.7 Hz, 1H), 7.68-7.60 (m, 1H). LC-MS (ES) for C$_{11}$H$_6$BrN [M+1]$^+$ 232.91.

Step c

A mixture of the 26 (1.0 equiv), the corresponding catechol (2.5 equiv), Cs$_2$CO$_3$ (2.2 equiv), CuI (0.2 equiv), and 2,2,6,6-tetramethyl-3,5-heptanedione (0.4 equiv) in dioxane (1.0 mL per mmol naphthalenol) in a sealed tube was heated at 110° C. under nitrogen atmosphere for 16 h. The cooled mixture was partitioned between ethyl acetate and water. The organic layer was separated, and the aqueous layer was extracted with ethyl acetate. The combined organic layers were washed with brine, dried over anhydrous Na$_2$SO$_4$, concentrated by rotary evaporation, and purified by column chromatography to give 27a-c.

5-(2-methoxyphenoxy)-2-naphthonitrile (27a)

(30%) $^1$H NMR (500 MHz, Acetone-d$_6$) δ 8.39 (d, J=8.7 Hz, 1H), 8.36 (d, J=1.4 Hz, 1H), 7.66 (dd, J=8.7, 1.6 Hz, 1H), 7.60 (d, J=8.3 Hz, 1H), 7.39 (t, J=8.0 Hz, 1H), 7.17 (ddd, J=8.2, 7.5, 1.6 Hz, 1H), 7.10 (dd, J=8.2, 1.5 Hz, 1H), 7.05 (dd, J=7.9, 1.6 Hz, 1H), 6.92 (td, J=7.7, 1.5 Hz, 1H), 6.64 (dd, J=7.8, 0.7 Hz, 1H), 3.63 (s, 3H). LC-MS (ES) for C$_{18}$H$_{13}$NO$_2$ [M+1]$^+$ 275.09.

5-(4-fluoro-2-methoxyphenoxy)-2-naphthonitrile (27b)

(38%) $^1$H NMR (400 MHz, CDCl$_3$) δ 8.40 (d, J=8.8 Hz, 1H), 8.17 (d, J=8.3 Hz, 1H), 8.11 (dd, J=7.5, 1.0 Hz, 1H), 7.94 (dd, J=8.8, 1.7 Hz, 1H), 7.82 (dd, J=8.7, 1.6 Hz, 1H), 7.75 (d, J=8.5 Hz, 1H), 7.68-7.61 (m, 1H), 7.12-7.06 (m, 1H), 6.57 (d, J=2.9 Hz, 1H). LC-MS (ES) for C$_{18}$H$_{12}$FNO$_2$ [M+1]$^+$ 294.07.

5-(4-chloro-2-methoxyphenoxy)-2-naphthonitrile (27c)

(85%) $^1$H NMR (400 MHz, CDCl$_3$) δ 8.42 (d, J=8.7 Hz, 1H), 8.23 (d, J=1.4 Hz, 1H), 7.63 (dd, J=8.7, 1.6 Hz, 1H), 7.57 (d, J=8.3 Hz, 1H), 7.41 (t, J=8.0 Hz, 1H), 7.02 (d, J=1.6 Hz, 1H), 6.94 (s, 1H), 6.80-6.76 (m, 2H), 3.78 (s, 3H). LC-MS (ES) for C$_{18}$H$_{12}$ClNO$_2$ [M+1]$^+$ 310.08.

Example 17

Synthesis Compounds 34a-c[8,9]

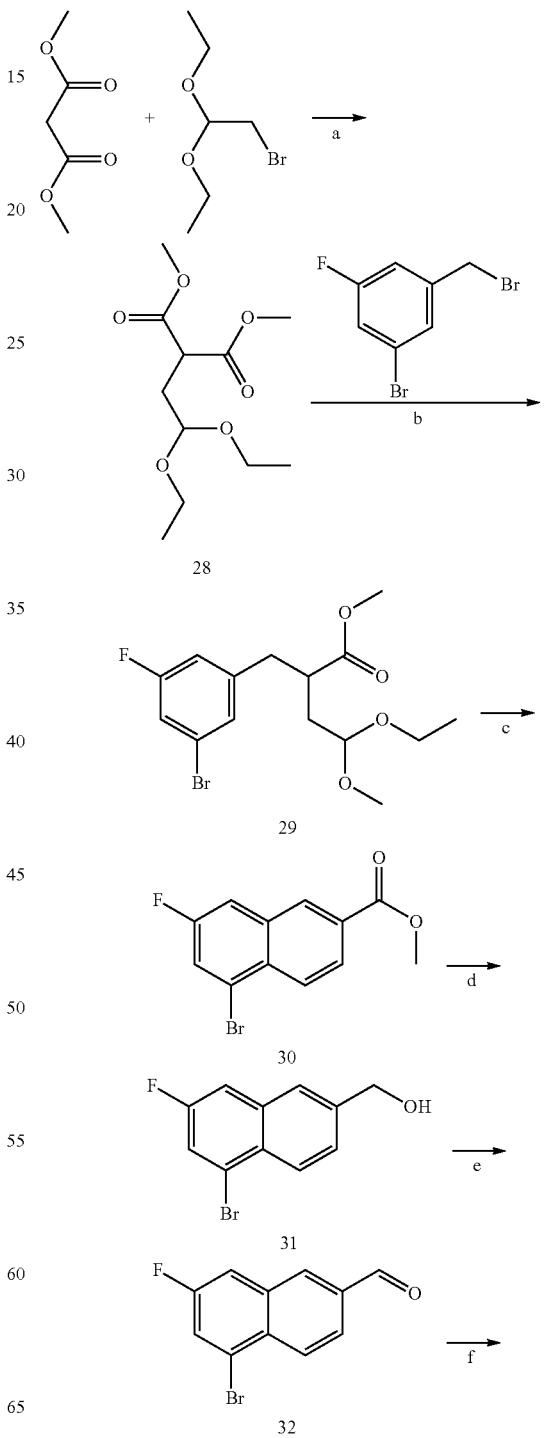

Scheme 3.5

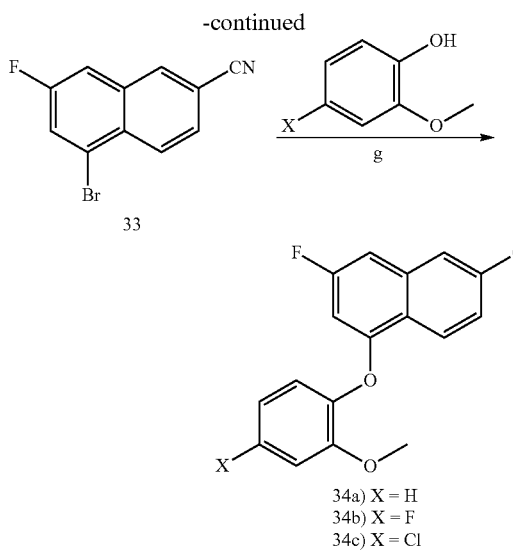

34a) X = H
34b) X = F
34c) X = Cl

Step a

A solution of dimethyl malonate (5.0 g, 47.8 mmol) in DMF (10 mL) was added dropwise to a suspension of NaH (1.9 g, 45.4 mmol; 60 wt % in mineral oil) in DMF (15 mL) at 0° C., and the mixture was stirred for 1 h at 40° C. Bromoacetaldehyde diethyl acetal (6.9 mL, 45.4 mmol) in DMF (10 mL) was added to the mixture, and the resulting solution was stirred for 16 h at 130° C. After cooling to room temperature, the mixture was poured saturated $NH_4Cl$ aqueous solution and extracted with ethyl acetate (2×100 mL). The combined organic was dried over anhydrous $Na_2SO_4$, filtered, concentrated by rotary evaporation, and purified by column chromatography to give dimethyl diethoxyethyl)malonate (28) (60%). $^1H$ NMR (400 MHz, $CDCl_3$) δ 4.66 (t, J=5.5 Hz, 1H), 3.70 (dq, J=9.3, 7.1 Hz, 2H), 3.58 (dq, J=9.3, 7.1 Hz, 2H), 3.37 (d, J=5.5 Hz, 2H), 1.23 (t, J=7.1 Hz, 6H). GC-MS (ES) for $C_{11}H_{20}O_6$ $[M+1]^+$ 249.

Step b.

A solution of 1-bromo-3-(bromomethyl)-5-fluorobenzene (4.5 g, 16.8 mmol) in DMF (10 mL) was added dropwise to a suspension of NaH (1.1 g, 45.4 mmol; 60 wt % in mineral oil) in DMF (15 mL), and the mixture was stirred for 1 h. 28 (6.3 mL, 25.2 mmol) in DMF (10 mL) was added to the mixture, and the resulting solution was stirred for 4 h. LiCl (0.8 g, 18.5 mmol) was added to the mixture, and was stirred for 2 h at 165° C. After cooling to room temperature, the mixture was poured saturated aqueous $NH_4Cl$ aqueous solution and extracted with ethyl acetate (2×100 mL). The combined organic was dried over anhydrous $Na_2SO_4$, filtered, concentrated by rotary evaporation, and purified by column chromatography to give methyl 2-(3-bromo-5-fluorobenzyl)-4,4-diethoxybutanoate (29) (83%). $^1H$ NMR (400 MHz, $CDCl_3$) δ 7.11-7.05 (m, 2H), 6.82 (dd, J=9.2, 1.7 Hz, 1H), 4.48 (dd, J=5.4, 3.3 Hz, 1H), 3.66 (s, 3H), 3.51-3.41 (m, 7H), 1.92 (td, J=7.4, 5.6 Hz, 2H), 1.20-1.16 (m, 6H). GC-MS (ES) for $C_{16}H_{22}BrFO_4$ $[M+1]^+$ 377.

Step c.

A solution of 29 (6.1 g, 16.3 mmol) in MeOH (6 mL) was added dropwise to a suspension of dichlorodicyanobenzoquinone (DDQ, 3.8 g, 16.7 mmol) in 80% aqueous $H_2SO_4$ (30 mL) at 0° C. After the addition was completed, the ice bath was removed and stirring was continued for 1 h. The mixture was poured in to ice water (100 mL), then the resulting brown precipitate was filtered, dissolved in ethyl acetate, and washed with $H_2O$ (100 mL). The organic layer was dried over anhydrous $Na_2SO_4$, filtered, concentrated rotary evaporation, and purified by column chromatography to give methyl 5-bromo-7-fluoro-2-naphthoate (30) (28%). $^1H$ NMR (600 MHz, Acetone-$d_6$) δ 8.67 (d, J=1.3 Hz, 1H), 8.31 (d, J=8.8 Hz, 1H), 8.18-8.14 (m, 1H), 7.95 (td, J=8.7, 8.2, 2.5 Hz, 2H), 3.97 (s, 3H). GC-MS (ES) for $C_{12}H_8BrFO_2$ $[M+1]^+$ 283.

Step d.

1.0 M diisobutylaluminium hydride in toluene (11.5 mL) was slowly added to a solution of 30 (1.3 g, 4.6 mmol) in THF (15 mL) at −78° C. After the addition was completed, the mixture was allowed to warm to room temperature and continuously stirred for 18 h. The mixture was poured in to HCl aqueous solution (0.5 N, 50 mL) and extracted in ethyl acetate (2×100 mL). The combined organic layer was dried over anhydrous $Na_2SO_4$, filtered, concentrated rotary evaporation, and purified by column chromatography to give (5-bromo-7-fluoronaphthalen-2-yl)methanol (31) (98%). $^1H$ NMR (400 MHz, $CDCl_3$) δ 8.19 (d, J=8.8 Hz, 1H), 7.77 (s, 1H), 7.59 (d, J=8.2 Hz, 1H), 7.53 (d, J=9.0 Hz, 1H), 7.45 (d, J=11.4 Hz, 1H), 4.90 (s, 2H). GC-MS (ES) for $C_{11}H_8BrFO$ $[M+1]^+$ 255.

Step e.

Pyridinium chlorochromate (PCC, 1.9 g, 9.0 mmol) was added to a solution of 31 (1.1 g, 4.5 mmol) in DCM (15 mL), and the mixture was stirred for 2 h prior to filtration through a short pad of silica gel. The filtrate was then concentrated rotary evaporation, and purified by column chromatography to give 5-bromo-7-fluoro-2-naphthaldehyde (32) (88%). $^1H$ NMR (400 MHz, $CDCl_3$) δ 10.20 (s, 1H), 8.34 (d, J=8.8 Hz, 1H), 8.29 (s, 1H), 8.01 (d, J=8.8 Hz, 1H), 7.77 (dd, J=8.0, 2.3 Hz, 1H), 7.64 (d, J=8.6 Hz, 1H). GC-MS (ES) for $C_{11}H_6BrFO$ $[M+1]^+$ 253.

Step f.

Hydroxylamine hydrochloride (0.5 g, 7.9 mmol) was added to a solution of 32 (1.0 g, 4.0 mmol) in DMSO (5.0 mL), and the mixture was stirred for 16 h at 100° C. After cooling to room temperature, the mixture was diluted with ethyl acetate (100 mL), and washed with saturated $NaHCO_3$ aqueous solution (2×50 mL). The organic was dried over anhydrous $Na_2SO_4$, filtered, concentrated by rotary evaporation, and purified by column chromatography to give 5-bromo-7-fluoro-2-naphthonitrile (33) (28%). $^1H$ NMR (400 MHz, $CDCl_3$) δ 10.20 (s, 1H), 8.34 (d, J=8.8 Hz, 1H), 8.29 (s, 1H), 8.01 (d, J=8.8 Hz, 1H), 7.77 (dd, J=8.0, 2.3 Hz, 1H), 7.64 (d, J=8.6 Hz, 1H). GC-MS (ES) for $C_{11}H_5BrFN$ $[M+1]^+$ 250.

Step g

A suspension of 33 (1.0 equiv), the corresponding phenol (2.0 equiv), $Cs_2CO_3$ (2.0 equiv), CuI (0.2 equiv) and 2,2,6,6-tetramethyl-3,5-heptanedione (0.4 equiv) in anhydrous dioxane (5.0 mL per 1.0 mmol of naphthalenol) was stirred at 115° C. under. $N_2$ atmosphere in a sealed tube for 24 h. The mixture was cooled down, quenched with brine, and extracted with ethyl acetate (3×10 mL). The combined organic layer was dried over anhydrous $Na_2SO_4$, filtered, concentrated by rotary evaporation, and purified by column chromatography to give 34a-c.

7-fluoro-5-(2-methoxyphenoxy)-2-naphthonitrile (34a)

(92%) $^1H$ NMR (400 MHz, Acetone-$d_6$) δ 8.53 (d, J=8.7 Hz, 1H), 8.46 (s, 1H), 7.78 (dd, J=8.7, 1.3 Hz, 1H), 7.44 (dd, J=9.4, 2.2 Hz, 1H), 7.39-7.33 (m, 1H), 7.27 (td, J=8.3, 1.5 Hz, 2H), 7.09 (td, J=7.7, 1.5 Hz, 1H), 6.51 (dd, J=10.5, 2.3 Hz, 1H), 3.78 (s, 3H). LC-MS (ES) for $C_{18}H_{12}FNO_2$ [M+1]$^+$ 294.12.

7-fluoro-5-(4-fluoro-2-methoxyphenoxy)-2-naphthonitrile (34b)

(61%) $^1$H NMR (400 MHz, Acetone-d$_6$) δ 8.51 (d, J=8.7 Hz, 1H), 8.45 (s, 1H), 7.77 (dd, J=8.7, 1.4 Hz, 1H), 7.43 (dd, J=9.3, 2.2 Hz, 1H), 7.33 (dd, J=8.8, 5.8 Hz, 1H), 7.10 (dd, J=10.6, 2.9 Hz, 1H), 6.86 (td, J=8.4, 2.9 Hz, 1H), 6.55 (dd, J=10.5, 2.3 Hz, 1H), 3.81 (s, 3H). LC-MS (ES) for $C_{18}H_{11}F_2NO_2$ [M+1]$^+$ 312.30.

5-(4-chloro-2-methoxyphenoxy)-7-fluoro-2-naphthonitrile (34c)

(67%) $^1$H NMR (400 MHz, Acetone-d$_6$) δ 8.49 (d, J=8.7 Hz, 1H), 8.45 (s, 1H), 8.15 (d, J=8.4 Hz, 1H), 7.77 (dd, J=8.7, 1.4 Hz, 1H), 7.45 (dd, J=9.3, 2.2 Hz, 1H), 7.26 (dd, J=5.2, 2.7 Hz, 1H), 7.13-7.08 (m, 1H), 6.62 (dd, J=10.4, 2.3 Hz, 1H), 3.83 (s, 3H). LC-MS (ES) for $C_{18}H_{11}ClFNO_2$ [M+1]$^+$ 328.11.

REFERENCES

Examples 12-17

1. Bollini, M.; Domaoal, R. A.; Thakur, V. V.; Gallardo-Macias, R.; Spasov, K. A.; Anderson, K. S.; Jorgensen, W. L. *J. Med. Chem.* 2011, 54, 8582-8591
2. Lee, W.-G.; Gallardo-Macias, R.; Frey, K. M.; Spasov, K. A.; Bollini, M.; Anderson, K. S.; Jorgensen, W. L. *J. Am. Chem. Soc.* 2013, 135, 16705-16713.
3. Liu, X.; Zhang, S. *Synlett.* 2011, 2, 268-272.
4. PCT Int. Appl. 2004071389.
5. Niculescu-Duvaz, D.; Niculescu-Duvaz, I.; Suijkerbuijk, B. M. J. M.; Menard, D.; Zambon, A.; Davies, L.; Pons, J.-F.; Whittaker, S.; Marais, R.; Springer, C. J. *Bioorg. Med. Chem.* 2013, 21, 1284-1304.
6. Uraguchi, D.; Koshimoto, K.; Ooi, T. *Chem. Comm.* 2010, 46, 300-302.
7. Linghu, X.; Mclaughlin, M.; Chen, C.-Y.; Reamer, R. A.; Dimichele, L.; Davies, I. W. *Tetrahedron Lett.* 2012, 53, 1550-1552.
8. Hartmann, R. W.; Palusczak, A.; Lacan, F.; Ricci, G.; Ruzziconi, R. *J. Enzyme Inhib. Med. Chem.* 2004, 19, 145-155
9. Gourvès, J.-P.; Ruzziconi, R.; Vilarroig, L. *J. Org. Chem.* 2001, 66, 617-619.

Example 18

Protein Crystallography

Materials and Methods

Recombinant RT52A enzyme was expressed and purified to homogeneity using methods described previously.[1,2] Crystals of RT52A in complex with 10b (aka JLJ555) were prepared using similar methods as the catechol diether complexes.[1] The final optimized condition for crystal growth consisted of 12.5% (w/v) PEG 8,000, 100 mM ammonium sulfate, 15 mM magnesium sulfate, 5 mM spermine, and 50 mM MES pH 6.0. Crystals were transferred to a cryo-solution containing 27% (v/v) ethylene glycol and flash cooled with liquid nitrogen.

Diffraction data for the best crystals were collected at Brookhaven NSLS on beam line X29A. High-resolution data sets for the best diffracting crystals were collected, indexed, integrated, and scaled into the C2 space group using HKL2000.[3] In order to obtain phases, molecular replacement was performed with Phaser[4] using a previously determined RT:3 (PDB code: 4H4M) as the search model.[2] The program Coot[5] was used for model building into the electron density. Maximum-likelihood restrained refinement in Phenix[6] was used to refine the structure after each cycle of model building until acceptable R-factors, geometry statistics (ideal rmsd for bonds and angles), and Ramachandran statistics were achieved. Iterative build, composite omit electron density maps were generated using Phenix Autobuild.[7]

TABLE 4

Data Collection and Refinement Statistics

| Complex | RT: 10b (JLJ555) |
|---|---|
| PDB Code | 4MFB |
| Resolution Limit, Å | 2.88 |
| X-Ray Source | NSLS X29A |
| Wavelength, Å | 1.075 |
| Space group | C2 |
| No. molecules in asymmetric unit | 1 |
| Unit cell, a, b, c in Å (α, β, γ, in °) | a = 223.56, b = 69.39, c = 104.79 (α = 90, β = 106.04, γ = 90) |
| Resolution range, Å | 36.6-3.10 |
| Last Shell, Å | 2.93-2.88 |
| R-sym (last shell) | 0.067 (0.479) |
| Completeness, % (last shell, %) | 99.0 (91.2) |
| No. of Reflections (Unique Reflections) | 130654 (35128) |
| Redundancy (last shell) | 3.7 (3.4) |
| Avg. I/σ (last shell) | 28.3 (2.2) |
| Total Number of Atoms (Protein/Inhibitor/Solvent) | 7877 (7831/29/17) |
| R-free, R-factor | 0.2694, 0.2368 |
| RMS deviation bond lengths, Å (angles, °) | 0.003 (0.770) |
| Avg. B-factor, Å$^2$ (Total/Protein/Inhibitor/Solvent, Å$^2$) | 63.46 (76.0/53.08/48.82) |
| Ramachandran Favored, Allowed, Outliers, % | 97, 2.7, 0.3 |

REFERENCES

Example 18

Protein Crystallography (1) Frey, K. M.; Bollini, M.; Mislak, A. C.; Cisneros, J. A.; Gallardo-Macias, R.; Jorgensen, W. L.; Anderson, K. S. *J. Am. Chem. Soc.* 2012, 134, 19501-19503.

(2) Das, K.; Bauman, J. D.; Clark, A. D., Jr.; Frenkel, Y. V.; Lewi, P. J.; Shatkin, A. J.; Hughes, S. H.; Arnold, E. *Proc. Nat. Acad. Sci. USA* 2008, 105, 1466-1471.

(3) Otwinowski, Z.; Minor, W. *Method Enzymol.* 1997, 276, 307-326.

(4) Mccoy, A. J.; Grosse-Kunstleve, R. W.; Adams, P. D.; Winn, M. D.; Storoni, L. C.; Read, R. J. *J. Appl. Crystallogr.* 2007, 40, 658-674.

(5) Emsley, P.; Lohkamp, B.; Scott, W. G.; Cowtan, K. *Acta Cryst. Sect. D* 2010, 66, 486-501.

(6) Adams, P. D.; Afonine, P. V.; Bunkoczi, G.; Chen, V. B.; Davis, I. W.; Echols, N.; Headd, J. J.; Hung, L. W.; Kapral, G. J.; Grosse-Kunstleve, R. W.; McCoy, A. J.; Moriarty, N. W.; Oeffner, R.; Read, R. J.; Richardson, D. C.; Richardson, J. S.; Terwilliger, T. C.; Zwart, P. H. *Acta Cryst. Sect. D* 2010, 66, 213-221.

(7) Terwilliger, T. C.; Grosse-Kunstleve, R. W.; Afonine, P. V.; Moriarty, N. W.; Adams, P. D.; Read, R. J.; Zwart, P. H.; Hung, L. W. *Acta Cryst. Sect. D* 2008, 64, 515-524.

REFERENCES FOR BACKGROUND, SUMMARY AND DETAILED DESCRIPTION OF THE INVENTION (1) Asahchop, E. L.; Wainberg, M. A.; Sloan, R. D.; Tremblay, C. L. *Antimicrob. Agents Chemother.* 2012, 56, 5000-5008.
(2) Zhan, P.; Chen, X.; Li, D.; Fang, Z.; De Clercq, E.; Liu, X. *Med. Res. Rev.* 2013, 33(S1), E1-E72.
(3) Permpalung, N.; Putcharoen, O.; Avihingsanon, A.; Ruxrungtham, K. *Expert Opin. Pharmacother.* 2012, 13, 2301-2317.
(4) James, C.; Preininger, L.; Sweet, M. *Am. J. Health-Syst. Pharm.* 2012, 69, 857-861.
(5) Janssen, P. A. J.; Lewi, P. J.; Arnold, E.; Daeyaert, F.; de Jonge, M.; Heeres, J.; Koymans, L.; Vinkers, M.; Guillemont, J.; Pasquier, E.; Kukla, M.; Ludovici, D.; Andries, K.; de Bethune, M.-P.; Pauwels, R.; Das, K.; Clark, A. D., Jr.; Frenkel, Y. V.; Hughes, S. H.; Medaer, B.; De Knaep, F.; Bohets, H.; De Clerck, F.; Lampo, A.; Williams, P.; Stoffels, P. *J. Med. Chem.* 2005, 48, 1901-1919.
(6) Bollini, M.; Cisneros, J. A.; Spasov, K. A.; Anderson, K. S.; Jorgensen, W. L. *Bioorg. Med. Chem. Lett.* 2013, 23, 5213-5216.
(7) Jorgensen, W. L. *Acc. Chem. Res.* 2009, 42, 724-733.
(8) Stepan, A. F.; Walker, D. P.; Bauman, J.; Price, D. A.; Baillie, T. A.; Kalgutkar, A. S.; Aleo, M. D. *Chem. Res. Toxicol.* 2011, 24, 1345-1410.
(9) Bollini, M.; Domaoal, R. A.; Thakur, V. V.; Gallardo-Macias, R.; Spasov, K. A.; Anderson, K. A.; Jorgensen, W. L. *J. Med. Chem.* 2011, 54, 8582-8591.
(10) Frey, K. M.; Bollini, M.; Mislak, A. C.; Cisneros, J. A.; Gallardo-Macias, R.; Jorgensen, W. L.; Anderson, K. A. *J. Am. Chem. Soc.* 2012, 134, 19501-19503.
(11) Fleming, F. F.; Wang, Q. *Chem. Rev.* 2003, 103, 2035-2077.
(12) Dahlgren, M. K.; Schyman, P.; Tirado-Rives, J.; Jorgensen, W. L. *J. Chem. Inf. Model.* 2013, 53, 1191-1199.
(13) Fleming, F. F.; Yao, L.; Ravikumar, P. C.; Funk, L.; Shook, B. C. *J. Med. Chem.* 2010, 53, 7902-7917.
(14) Jorgensen, W. L.; Bollini, M.; Thakur, V. V.; Domaoal, R. A.; Spasov, K.; Anderson, K. S. *J. Am. Chem. Soc.* 2011, 133, 15686-15696.
(15) Jorgensen, W. L.; Tirado-Rives, J. *J. Comput. Chem.* 2005, 26, 1689-1700.
(16) Jorgensen, W. L.; Maxwell, D. S.; Tirado-Rives, J. *J. Am. Chem. Soc.* 1996, 118, 11225-11236.
(17) Jorgensen, W. L.; Tirado-Rives, J. *Proc. Natl. Acad. Sci. U.S.A.* 2005, 102, 6665-6670.
(18) Jorgensen, W. L.; Chandrasekhar, J.; Madura, J. D.; Impey, R. W.; Klein, M. L. *J. Chem. Phys.* 1983, 79, 926-935.
(19) For a review, see: Jorgensen, W. L.; Thomas, L. T. *J. Chem. Theory Comput.* 2008, 4, 869-876.
(20) Heugebaert, T. S. A.; Roman, B. I.; Sevens, C. V. *Chem Soc. Rev.* 2012, 41, 5626-5640.
(21) Kim, J. T.; Hamilton, A. D.; Bailey, C. M.; Domaoal, R. A.; Wang, L.; Anderson, K. S.; Jorgensen, W. L. *J. Am. Chem. Soc.* 2006, 128, 15372-15373.
(22) Frisch, M. J.; Gaussian 09, Revision A. 02; Gaussian, Inc.: Wallingford, Conn., 2009. [Full reference is given in the Supporting Information.]
(23) Whitlock, G. A; Blagg, J; Fish, P V. *Bioorg. Med. Chem. Lett.* 2008, 18, 596-599.
(24) Bamberg, J. T.; O'Yang, C.; Sui, M.; Zhao, S.-H. PCT Int. Appl. 2008055808.
(25) Zheng, C.; Lu, Y.; Zhang, J.; Chen, X.; Chai, Z.; Ma, W.; Zhao, G. *Chem. Eur. J.* 2010, 16, 5853-5857.
(26) (a) Ryabova, S. Y.; Alekseeva, L. M.; Lisitsa, E. A.; Granik, V. G. *Russ. Chem. Bull., Int. Ed.,* 2006, 55, 1248-1254. (b) Attanasi, O.; Palma, P.; Serra-Zanetti, F. *Synthesis,* 1983, 9, 741-742.
(27) Bode, M. L.; Kaye, P. T. *J. Chem. Soc. Perkin Trans.* 1 1993, 1809-1813.
(28) (a) Newman, S. G.; Aureggi, V.; Bryan, C. S.; Lautens, M. *Chem. Commun.* 2009, 5236-5238. (b) Zhou, W.; Chen, W.; Wang, L. *Org. Biomol. Chem.* 2012, 10, 4172-4178.
(29) Lin, T. S.; Luo, M. Z.; Liu, M. C.; Pai, S. B.; Dutschman, G. E.; Cheng, Y. C. *Biochem. Pharmacol.* 1994, 47, 171-174.
(30) Ray, A. S.; Yang, Z.; Chu, C. K.; Anderson, K. S. *Antimicrob. Agents Chemother.* 2002, 46, 887-891.
(31) de Bethune, M.-P. *Antiviral Res.* 2010, 85, 75-90.
(32) Lipinski, C. A.; Lombardo, F.; Dominy, B. W.; Feeney, P. J. *Adv. Drug Deliv. Rev.* 2001, 46, 3-26.
(33) Jorgensen, W. L.; Duffy, E. M. *Adv. Drug Deliv. Rev.* 2002, 54, 355-366.
(34) Baka, E.; Comer, J. E. A; Takács-Novák, K. *J. Pharm. Biomed. Anal.* 2008, 46, 335-341.
(35) Morelock, M. M.; Choi, L. L.; Bell, G. L.; Wright, J. L. *J. Pharm. Sci.* 1994, 83, 948-952.
(36) Weuts, I.; Van Dycke, F.; Voorspoels, J.; de Cort, S.; Stokbroekx, S.; Leemans, R.; Brewster, M. E.; Xu, D.; Segmuller, B.; Turner, Y. T. A.; Roberts, C. J.; Davies, M. C.; Qi, S.; Craig, D. Q. M.; Reading, M. *J. Pharm. Sci.* 2011, 100, 260-274.
(37) Sun, L.-Q.; Qin, B.; Huang, L.; Qian, K.; Chen, C.-H.; Lee, K.-H.; Xie, L. *Bioorg. Med. Chem. Lett.* 2012, 22, 2376-2379.
(38) ChemDraw, CambridgeSoft Inc., Cambridge, Mass., 2013.

REFERENCES FOR DISCUSSION OF NAPHTHYLPHENYL ETHERS (1) De Clercq, E. The Nucleoside Reverse Transcriptase Inhibitors, Nonnucleoside Reverse Transcriptase Inhibitors, and Protease Inhibitors in the Treatment of HIV Infections (AIDS). *Adv. Pharmacol.* 2013, 67, 317-358.
(2) Reynolds, C.; de Koning, C. B.; Pelly, S. C.; van Otterlo, W. A. L.; Bode, M. L. In search of a treatment for HIV—current therapies and the role of non-nucleoside reverse transcriptase inhibitors (NNRTIs). *Chem. Soc. Rev.* 2012, 41, 4657-4670.
(3) Zhan, P.; Chen, X.; Li, D.; Fang, Z.; De Clercq, E.; Liu, X. HIV-1 NNRTIs: Structural Diversity, Pharmacophore Similarity, and Implications for Drug Design. *Med. Res. Rev.* 2013, 33, E1-E72.
(4) Bollini, M.; Domaoal, R. A.; Thakur, V. V.; Gallardo-Macias, R.; Spasov, K. A.; Anderson, K. S.; Jorgensen, W. L. Computationally-Guided Optimization of a Docking Hit to Yield Catechol Diethers as Potent Ani-HIV Agents. *J. Med. Chem.* 2011, 54, 8582-8591.
(5) Lee, W.-G; Gallardo-Macias, R.; Frey, K. M.; Spasov, K. A.; Bollini, M.; Anderson, K. S.; Jorgensen, W. L. Picomolar Inhibitors of HIV Reverse Transcriptase Featuring Bicyclic Replacement of a Cyanovinylphenyl Group. *J. Am. Chem. Soc.* 2013, 135, 16705-16713.
(6) de Béthune, M.-P. Non-nucleoside reverse transcriptase inhibitors (NNRTIs), their discovery, development, and use in the treatment of HIV-1 infection: A review of the last 20 years (1989-2009). *Antiviral Res.* 2010, 85, 75-90.

(7)) Frey, K. M.; Bollini, M.; Mislak, A. C.; Cisneros, J. A.; Gallardo-Macias, R.; Jorgensen, W. L.; Anderson, K. S. Crystal Structures of HIV-1 Reverse Transcriptase with Picomolar Inhibitors Reveal Key Interactions for Drug Design. *J. Am. Chem. Soc.* 2012, 134, 19501-19503.

(8) Frey, K. M.; Gray, W. T.; Spasov, K. A.; Bollini, M.; Gallardo-Macias, R.; Jorgensen, W. L.; Anderson, K. S. Structure-Based Evaluation of C5 Derivatives in the Catechol Diether Series Targeting HIV-I Reverse Transcriptase. *Chem. Biol. Drug Des.* 2014, 83, 541-549.

(9) Baka, E.; Comer, J. E. A; Takács-Novák, K. Study of equilibrium solubility measurement by saturation shake-flask method using hydrochlorothiaide as model compound. *J. Pharm. Biomed. Anal.* 2008, 46, 335-341.

(10) Lin, T. S.; Luo, M. Z.; Liu, M. C.; Pai, S. B.; Dutschman, G. E.; Cheng, Y. C. Antiviral activity of 2',3'-dideoxy-β-L-5-fluorocytidine (β-L-EddC) and 2',3'-dideoxy-β-L-cytidine (β-L-ddC) against hepatitis B virus and human immunodeficiency virus type 1 in vitro. *Biochem. Pharmacol.* 1994, 47, 171-174.

(11) Ray, A. S.; Yang, Z.; Chu, C. K.; Anderson, K. S. Novel use of a guanosine prodrug approach to convert 2',3'-didehydro-2',3'-dideoxyguanosine into a viable antiviral agent. *Antimicrob. Agents Chemother* 2002, 46, 887-891.

(12) Morelock, M. M.; Choi, L. L.; Bell, G. L.; Wright, J. L. Estimation and correlation of drug water solubility with pharmacological parameters required for biological activity. *J. Pharm. Sci.* 1994, 83, 948-952.

(13) Weuts, I.; Van Dycke, F.; Voorspoels, J.; de Cort, S.; Stokbroekx, S.; Leemans, R.; Brewster, M. E.; Xu, D.; Segmuller, B.; Turner, Y. T. A.; Roberts, C. J.; Davies, M. C.; Qi, S.; Craig, D. Q. M.; Reading, M. Physicochemical Properties of the Amorphous Drug, Cast Films, and Spray Dried Powders to Predict Formulation Probability of Success for Solid Dispersions: Etravirine. *J. Pharm. Sci.* 2011, 100, 260-274.

(14) Janssen, P. A. J.; Lewi, P. J.; Arnold, E.; Daeyaert, F.; de Jonge, M.; Heeres, J.; Koymans, L.; Vinkers, M.; Guillemont, J.; Pasquier, E.; Kukla, M.; Ludovici, D.; Andries, K.; de Bethune, M.-P.; Pauwels, R.; Das, K.; Clark, A. D., Jr.; Frenkel, Y. V.; Hughes, S. H.; Medaer, B.; De Knaep, F.; Bohets, H.; De Clerck, F.; Lampo, A.; Williams, P.; Stoffels, P. In search of a novel anti-HIV drug: multidisciplinary coordination in the discovery of 4-[[4-[[4-[(1E)-2-cyanoethenyl]-2,6-dimethylphenyl]amino]-2-pyrimidinyl]amino]benzonitrile (R278474, rilpivirine). *J. Med. Chem.* 2005, 48, 1901-1919.

(15) Sun, L.-Q.; Qin, B.; Huang, L.; Qian, K.; Chen, C.-H.; Lee, K.-H.; Xie, L. Optimization of 2,4-diarylanilines as non-nucleoside HIV-1 reverse transcriptase inhibitors. *Bioorg. Med. Chem. Lett.* 2012, 22, 2376-2379.

(16) Jorgensen, W. L.; Duffy, E. M. Prediction of drug solubility from structure. *Adv. Drug Deliv. Rev.* 2002, 54, 355-366.

(17) Bollini, M.; Cisneros, J. A.; Spasov, K. A.; Anderson, K. S.; Jorgensen, W. L. Optimization of diarylazines as anti-HIV agents with dramatically enhanced solubility. *Bioorg. Med. Chem. Lett.* 2013, 23, 5213-5216.

(18) Jorgensen, W. L. Efficient Drug Lead Discovery and Optimization. *Acc. Chem. Res.* 2009, 42, 724-733.

What is claimed is:

1. A compound of the formula (IIA):

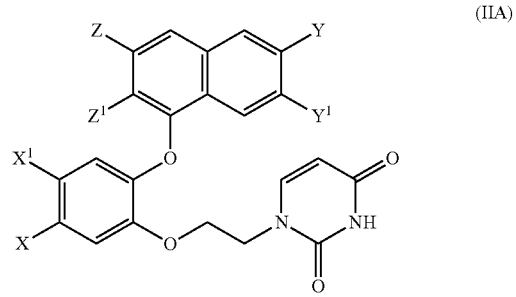

(IIA)

wherein:

X and $X^1$ are independently H, a halogen (F, Cl, Br, I), CN, $NO_2$ or an optionally substituted alkyl group;

Y and $Y^1$ are independently H, a $C_1$-$C_6$ alkyl optionally substituted with up to three fluorines, CN, halogen (F, Br, Cl, I), $C_1$-$C_6$ alkoxy, $C_1$-$C_6$ hydroxyalkyl, $C_1$-$C_6$ alkoxyalkyl, or $C_1$-$C_6$ polyoxyalkyl;

Z and $Z^1$ are independently H, OH, a $C_1$-$C_3$ alkyl group which is optionally substituted with up to 3 halogens, a halogen, $NO_2$ or CN;

and the pharmaceutically acceptable salts, solvates and polymorphs thereof.

2. The compound of claim 1, and the pharmaceutically acceptable salts, enantiomers, stereoisomers, solvates and polymorphs thereof, wherein $X^1$, $Y^1$ and $Z^1$ are H and X is H, F, Cl or Br, Y is CN and Z is H, F, Cl or Br.

3. The compound of claim 1, and the pharmaceutically acceptable salts, enantiomers, stereoisomers, solvates and polymorphs thereof, wherein $X^1$, $Y^1$ and $Z^1$ are H and X is H or F, Y is CN and Z is H or F.

4. A compound of the formula (II):

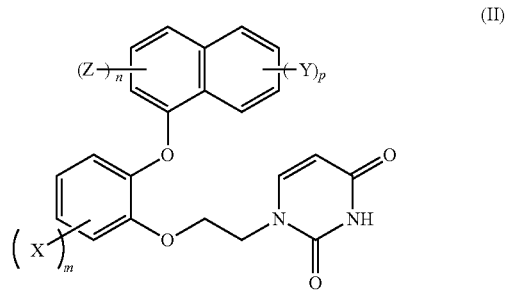

(II)

wherein:

X is H, a halogen (F, Cl, Br, I), CN, $NO_2$, or an optionally substituted alkyl group;

Y is H, a $C_1$-$C_6$ alkyl optionally substituted with up to three fluorines, CN or halogen (F, Br, Cl, I), $C_1$-$C_6$ alkoxy; $C_1$-$C_6$ hydroxyalkyl, $C_1$-$C_6$ alkoxyalkyl, $C_1$-$C_6$ polyoxyalkyl;

Z is H, OH, a $C_1$-$C_3$ alkyl group which is optionally substituted with up to 3 halogens, a halogen, $NO_2$ or CN; and m and p are independently 0, 1, 2, 3 or 4 and n is 0, 1, 2 or 3;

and the pharmaceutically acceptable salts, solvates and polymorphs thereof.

5. The compound of claim 4, and the pharmaceutically acceptable salts, solvates and polymorphs thereof, wherein m, n and p are 1.

6. A compound according to the chemical structure:

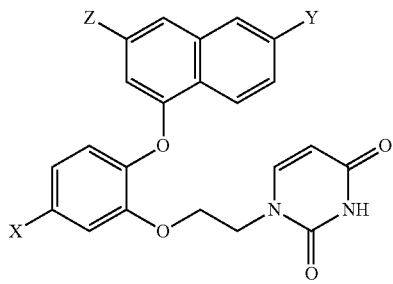

where X is H, Cl or F;
Y is H, CH$_3$, Cl, F or CN; and
Z is H, CH$_3$, Cl or F, or
a pharmaceutically acceptable salt, solvate or polymorph thereof.

7. The compound according to claim 6 wherein X is H or F, Y is CN and Z is H, F or Cl, often H or F.

8. A compound according to claim 6 according to the chemical structure:

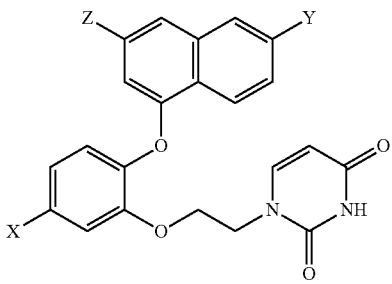

IIB where X is H, Y is H and Z is H; or
X is H, Y is CH$_3$ and Z is H; or
X is H, Y is Cl and Z is H; or
X is H, Y is Cl and Z is Cl; or
X is H, Y is CN and Z is H; or
X is H, Y is CN and Z is Cl; or
X is F, Y is CN and Z is Cl; or
X is Cl, Y is CN and Z is Cl; or
X is F, Y is CN and Z is H; or
X is Cl, Y is CN and Z is H; or
X is H, Y is CN and Z is F; or
X is F, Y is CN and Z is F; or
X is Cl, Y is CN and Z is F; or
a pharmaceutically acceptable salt, solvate or polymorph thereof.

9. A compound according to claim 8, wherein
X is H, Y is CN and Z is H; or
X is F, Y is CN and Z is H; or
X is H, Y is CN and Z is F; or
X is F, Y is CN and Z is F; or
a pharmaceutically acceptable salt, solvate or polymorph thereof.

10. A pharmaceutical composition comprising an effective amount of a compound of claim 1 and a pharmaceutically acceptable carrier, additive and/or excipient, optionally in combination with at least one additional anti-HIV agent.

11. The composition according to claim 10, wherein said compound is combined with an additional anti-HIV agent.

12. The composition according to claim 11, wherein said anti-HIV agent is selected from the group consisting of nucleoside reverse transcriptase inhibitors (NRTI), other non-nucleoside reverse transcriptase inhibitors protease inhibitors, fusion inhibitors and mixtures thereof.

13. The composition according to claim 11, wherein said anti-HIV agent is selected from the group consisting of, a fusion inhibitor or a mixture thereof.

14. The composition according to claim 11, wherein said anti-HIV agent is nevirapine or a mixture thereof.

15. A method of treating a patient suffering from an HIV infection comprising administering an effective amount of a composition according to claim 10 to the patient.

16. A method of inhibiting HIV reverse transcriptase in a subject, said method comprising administering to said subject a therapeutically effective amount of a composition according to claim 10.

17. The method according to claim 15, wherein said patient or subject is a human.

18. The method according to claim 15 wherein said HIV infection is an HIV infection of HIV-1 and/or HIV-2.

19. The method according to claim 18 wherein said HIV-1 and/or HIV-2 is a wild-type or mutant strain of HIV.

* * * * *